US011433022B2

(12) United States Patent
Yoo et al.

(10) Patent No.: US 11,433,022 B2
(45) Date of Patent: Sep. 6, 2022

(54) RAPIDLY-ORODISPERSIBLE TABLETS HAVING AN IN INTERIOR CAVITY

(71) Applicant: APRECIA PHARMACEUTICALS LLC, Blue Ash, OH (US)

(72) Inventors: Jaedeok Yoo, Princeton, NJ (US); Aleece M. Phillips, Yardley, PA (US); Thomas J. Bradbury, Yardley, PA (US); Thomas G. West, Lawrenceville, NJ (US)

(73) Assignee: APRECIA PHARMACEUTICALS LLC, Blue Ash, OH (US)

( * ) Notice: Subject to any disclaimer, the term of this patent is extended or adjusted under 35 U.S.C. 154(b) by 0 days.

(21) Appl. No.: 17/513,307

(22) Filed: Oct. 28, 2021

(65) Prior Publication Data

US 2022/0054409 A1    Feb. 24, 2022

Related U.S. Application Data

(63) Continuation of application No. PCT/US2021/039137, filed on Jun. 25, 2021.

(60) Provisional application No. 63/214,343, filed on Jun. 24, 2021, provisional application No. 63/044,740, filed on Jun. 26, 2020.

(51) Int. Cl.
*A61K 9/56* (2006.01)
*A61K 9/00* (2006.01)
*A61K 9/20* (2006.01)

(52) U.S. Cl.
CPC .......... *A61K 9/0056* (2013.01); *A61K 9/2077* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 4,371,516 A | 2/1983 | Gregory et al. |
| 4,631,837 A | 12/1986 | Magoon |
| 4,642,903 A | 2/1987 | Davies |
| 4,855,326 A | 8/1989 | Fuisz |
| 5,178,878 A | 1/1993 | Wehling et al. |
| 5,380,473 A | 1/1995 | Bogue et al. |
| 5,518,730 A | 5/1996 | Fuisz |
| 5,578,322 A | 11/1996 | Shiozawa et al. |
| 5,607,697 A | 3/1997 | Alkire et al. |
| 5,631,023 A | 5/1997 | Kearney et al. |
| 5,738,875 A | 4/1998 | Yarwood et al. |
| 6,047,484 A | 4/2000 | Bolland et al. |
| 6,280,771 B1 | 8/2001 | Monkhouse et al. |
| 6,471,992 B1 | 10/2002 | Yoo et al. |
| 6,945,638 B2 | 9/2005 | Teung et al. |
| 6,990,748 B2 | 1/2006 | Magoon et al. |
| 7,300,668 B2 | 11/2007 | Pryce Lewis et al. |
| 7,749,533 B2 | 7/2010 | Fu et al. |
| 7,875,290 B2 | 1/2011 | Payumo et al. |
| 8,088,415 B2 | 1/2012 | Wang et al. |
| 8,888,480 B2 | 11/2014 | Yoo et al. |
| 9,050,254 B2 | 6/2015 | Jacob et al. |
| 9,114,072 B2 | 8/2015 | Yoo et al. |
| 9,314,429 B2 | 4/2016 | Jacob et al. |
| 9,339,489 B2 | 5/2016 | Jacob et al. |
| 9,409,699 B2 | 8/2016 | Weigel |
| 9,427,399 B2 | 8/2016 | Adams et al. |
| 9,463,160 B2 | 10/2016 | Yoo et al. |
| 9,492,380 B2 | 11/2016 | Jacob et al. |
| 9,517,591 B2 | 12/2016 | Yoo et al. |
| 9,517,592 B2 | 12/2016 | Yoo et al. |
| 9,610,735 B2 | 4/2017 | Yoo et al. |
| 9,616,018 B2 | 4/2017 | Jacob et al. |
| 9,668,968 B2 | 6/2017 | Adams et al. |
| 9,669,009 B2 | 6/2017 | Jacob et al. |
| 9,828,119 B2 | 11/2017 | Wolf |
| 9,844,930 B2 | 12/2017 | Hoover et al. |
| 9,908,293 B2 | 3/2018 | Yoo et al. |
| 10,028,909 B2 | 7/2018 | Jacob et al. |

(Continued)

FOREIGN PATENT DOCUMENTS

| WO | 2014143935 | 9/2014 |
|---|---|---|
| WO | 2020081561 | 4/2020 |

OTHER PUBLICATIONS

Cheng et al., "Creating Tablets with Structures for Controlled Release using 3D Printing Technology", Oct. 29, 2017, ISPE 2017 Annual Meeting & Expo, presentation (24 pages).
Smith et al., "Pharmaceutical 3D printing: Design and qualification of a single step print and fill capsule", Mar. 29, 2018, International Journal of Pharmaceutics, vol. 544, p. 21-30 (10 pages).
Smith et al., "3D printed capsules for quantitative regional absorption studies in the GI tract", Aug. 30, 2018, International Journal of Pharmaceutics, vol. 550, p. 418-428 (11 pages).
Robles-Martinez et al., "3D Printing of a Multi-Layered Polypill Containing Six Drugs Using a Novel Stereolithographic Method", Jun. 11, 2019, MDPI Pharmaceutics, vol. 11 No. 274 (16 pages).
International Preliminary Report on Patentability (Chapter II), dated Feb. 25, 2022, in corresponding International Application No. PCT/US2021/039137 filed Jun. 25, 2021 (18 pages).

(Continued)

*Primary Examiner* — David J Blanchard
*Assistant Examiner* — Daniel F Coughlin
(74) *Attorney, Agent, or Firm* — Daniel F. Nesbitt; Nesbitt IP LLC

(57) ABSTRACT

A rapidly-orodispersible dosage form comprising a porous, bound-powder matrix and one or more internal cavities is provided, as well as three-dimensional printing methods for making the same. Each internal cavity is configured to contain one or more payloads, particularly pharmaceutical medicaments, while isolating the payloads from the external environment outside of the dosage form. Each payload can be contained within its cavity in its native form without having to be combined with the bound-powder matrix or binding liquid. Dosage forms can disintegrate in water or saliva in less than two minutes, independently of the payload(s) or medicament(s) contained within. The dosage forms can be formed as unitary tablets, or as two-piece tablets comprising a container body and a lidding body that are secured together to isolate the one or more cavities and their payloads inside.

17 Claims, 18 Drawing Sheets

(56) References Cited

U.S. PATENT DOCUMENTS

| | | |
|---|---|---|
| 10,064,945 B2 | 9/2018 | Barnscheid et al. |
| 10,071,372 B2 | 9/2018 | Nitsch |
| 10,118,335 B2 | 11/2018 | Yoo et al. |
| 10,132,565 B2 | 11/2018 | Jacob et al. |
| 10,420,785 B2 | 9/2019 | Jacob et al. |
| 10,449,712 B2 | 10/2019 | Yoo et al. |
| 2003/0133975 A1 | 7/2003 | Yoo et al. |
| 2007/0218129 A1 | 9/2007 | Besse |
| 2009/0060983 A1 | 3/2009 | Bunick et al. |
| 2010/0016348 A1 | 1/2010 | Bunick et al. |
| 2011/0014295 A1 | 1/2011 | Rubino et al. |
| 2012/0207929 A1 | 8/2012 | Yoo et al. |
| 2017/0202807 A1 | 7/2017 | Jacob et al. |
| 2017/0258763 A1 | 9/2017 | Jacob et al. |
| 2017/0312179 A1 | 11/2017 | Gamberini |
| 2017/0322068 A1 | 11/2017 | Gueller et al. |
| 2018/0031410 A1 | 2/2018 | Lux et al. |
| 2018/0141275 A1 | 5/2018 | Patel et al. |
| 2018/0241404 A1 | 8/2018 | Bu et al. |
| 2019/0209468 A1 | 7/2019 | Deng et al. |
| 2019/0240902 A1 | 8/2019 | Bedoret et al. |
| 2019/0321299 A1 | 10/2019 | Li |
| 2019/0374471 A1 | 12/2019 | Basit et al. |
| 2020/0001521 A1 | 1/2020 | Yoo et al. |
| 2021/0038520 A1 | 2/2021 | Nowak et al. |

OTHER PUBLICATIONS

"Waiver of In Vivo Bioavailability and Bioequivalence Studies for Immediate-Release Solid Oral Dosage Forms Based on a Biopharmaceutics Classification System", Aug. 2000, U.S. Department of Health and Human Services, Food & Drug Administration, CDER (16 pages).

"Lutrol® F 68 NF", 2001, BASF Pharma Ingredients (1 page).

United States Pharmacopeia, Chapters <701>, <1216>, <1217>, May 2012 edition, p. 293-295 and 867-870 (7 pages).

United States Pharmacopeia, Chapter <711>, Dec. 2012 edition, p. 5642-5648 (7 pages).

Chianrabutra et al., "A Dry Powder Material Delivery Device for Multiple Material Additive Manufacturing", Aug. 2014, University of Southampton, 2014 International Solid Freeform Fabrication Symposium (13 pages).

"Flex PowderDose", Jan. 17, 2018 according to Wayback Machine, Chemspeed Technologies, https://www.chemspeed.com/flex-powderdose/ (2 pages).

"Approved Drug Products with Therapeutic Equivalence Evaluations", 40$^{th}$ ed., Mar. 2020, U.S. Department of Health and Human Services, Food & Drug Administration, CDER (1,631 pages).

International Search Report and Written Opinion dated Oct. 8, 2021 by the European Patent Office (as International Search Authority) for related International Application No. PCT/US2021/039137 filed Jun. 25, 2021 (11 pages).

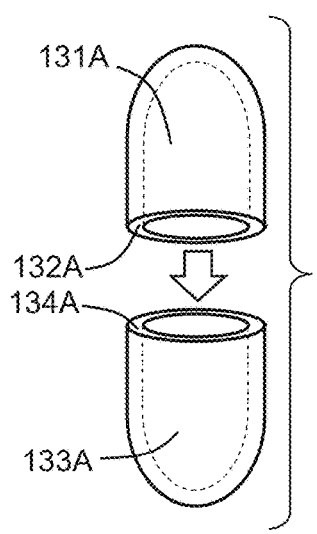
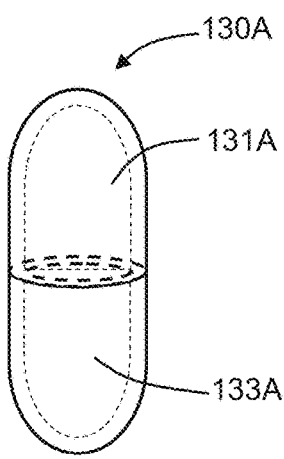
Fig. 22    Fig. 23
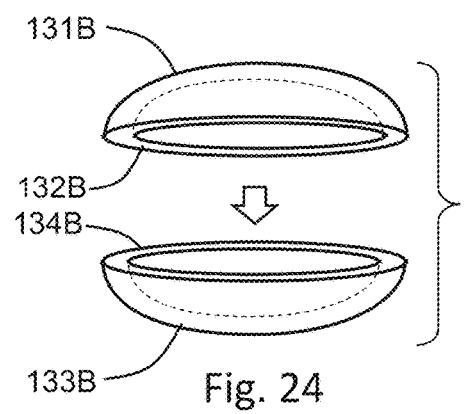
Fig. 24
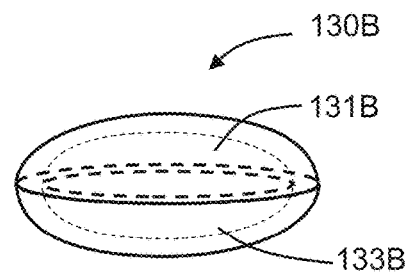
Fig. 25
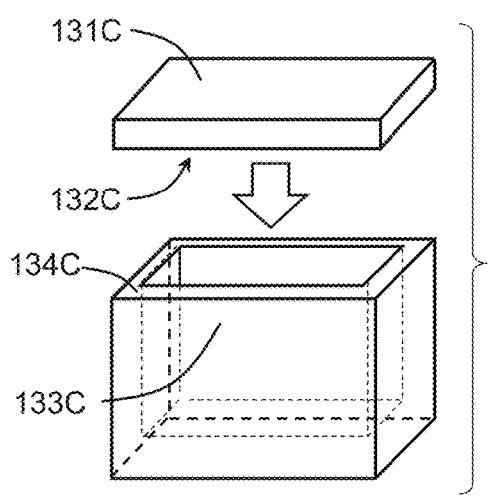
Fig. 26
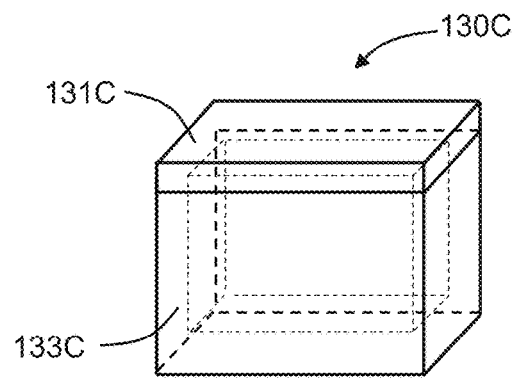
Fig. 27

RAPIDLY-ORODISPERSIBLE TABLETS HAVING AN IN INTERIOR CAVITY

CROSS-REFERENCE TO EARLIER FILED APPLICATIONS

The present application is a continuation of International Application No. PCT/US2021/039137 filed Jun. 25, 2021, which claims the benefit of U.S. Provisional Application No. 63/044,740 filed Jun. 26, 2020, and U.S. Provisional Application No. 63/214,343 filed Jun. 24, 2021, the entire disclosures of which are hereby incorporated by reference.

FIELD OF THE INVENTION

This invention is related to the field of manufacturing dosage or tablet forms for containing medicaments, pharmaceutical excipients, and other payloads.

BACKGROUND OF THE INVENTION

Solid oral dosage forms, particularly tablets and capsules, have long been a common administration route for a subject taking both prescription and non-prescription medications. Active pharmaceutical ingredients (API) that can be synthesized and/or formed into solid powders, particles, or agglomerates can conveniently be manufactured into tablets or capsules, and most people can swallow such dosage forms whole with a minimum volume of liquid, typically water.

However, a significant number of patients, including young and elderly people, have difficulties swallowing solid dosage forms, particularly dosage forms containing high dosages of API and/or excipients necessary to support the API within the dosage form itself. Difficulty in swallowing leads to poor patient compliance. Some attempts to solve this problem have led to the development of oral liquid and injectable formulations, but stability, contamination, and inaccurate dosing have all been drawbacks to using such dosage forms.

The production of rapidly dispersible solid oral dosage forms has been another potential solution for providing medication to those with difficulties swallowing medication. Rapidly-orodispersible dosage forms can disperse or disintegrate in the mouth in a minimal amount of saliva or water. Such dosage forms can be easier to swallow and accurately dose, and in some instances can provide a more rapid therapeutic action. U.S. Pat. No. 7,749,533 discloses a dosage form containing granules containing a drug, porous plastic substance, water penetration enhancer, binder and drug. The granules must be compressed in order to create the dosage form. U.S. Pat. No. 4,371,516 and U.S. Pat. No. 5,738,875 disclose freeze-dried dosage forms, and U.S. Pat. No. 5,178,878 discloses a soft-compressed orodispersible dosage form. Effervescent dosage forms and quick-release coatings of insoluble microparticles are described in U.S. Pat. Nos. 5,578,322 and 5,607,697. Freeze dried foams and liquids are described in U.S. Pat. Nos. 4,642,903 and 5,631,023. Melt-spun dosage forms are described in U.S. Pat. Nos. 4,855,326, 5,380,473 and 5,518,730. U.S. Patent Publication No. 2007/0218129 discloses an immediate release dispersible and orodispersible solid pharmaceutical composition having the form of particles with a size lower than 710 μm upon dispersion into water, wherein the formulation is made by wet granulation, and with disintegration times ranging from 53 to 60 sec. The disclosures of each of the patents and patent publications listed above are incorporated by reference in their entireties.

Rapidly-orodispersible dosage forms have also been produced using additive manufacturing, including three-dimensional printing (3DP) platforms utilizing 3DP equipment assemblies and systems (see U.S. Pat. Nos. 6,471,992, 9,114,072, 9,314,429, 9,339,489, 9,463,160, 9,492,380, 9,616,018, 9,669,009, 10,029,909, and 10,420,785, as well as U.S. Patent Publication Nos. 2003/0133975, 2012/0207929, 2017/0202807, and 2017/0258763, the descriptions of which are incorporated by reference in their entireties). 3DP platforms in particular can generally include solid freeform fabrication and/or rapid-prototyping techniques in which thin layers of powder are spread onto a surface and selected region of the powder are bound together by the controlled deposition ("printing") of a liquid. This basic operation is repeated layer-by-layer, with each new layer formed on top of and adhered to the previously printed layer, to eventually make three-dimensional objects. When the printed objects have sufficient cohesion, they may be separated from unbound powder within or surrounding the object.

Several systems and equipment assemblies for additively manufactured or 3DP articles are commercially available or in use by others, for example: Massachusetts Institute of Technology Three-Dimensional Printing Laboratory (Cambridge, Mass.), Z Corporation's (now part of 3D Systems) 3DP and HD3DP™ systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc.'s Dimension™ system (Eden Prairie, Minn.), Objet Geometries (Billerica, Mass. or Rehovot, Israel), Xpress3D (Minneapolis, Minn.), and 3D Systems' Invision™ system (Valencia, Calif.). Non-limiting examples of 3DP systems capable of forming rapidly-orodispersible tablets have been described in U.S. Pat. Nos. 8,888,480, 9,517,591, 9,517,592, 9,610,735, 9,908,293, 10,118,335, and 10,449,712, as well as U.S. Patent Publication Nos. 2018/0141275 and 2020/0001521, the disclosures of which are incorporated by reference in their entireties.

Nonetheless, some API compounds are incompatible with the powder, the binder material, or manufacturing conditions necessary to construct orodispersible dosage forms with sufficient hardness and friability to withstand storage and handling while also exhibiting a rapid disintegration rate. Further, many additive manufacturing and 3DP systems and techniques used to make dosage forms, including rapidly-orodispersible forms, that include API compounds result in excess API waste that often cannot be recovered. Therefore, there remains a need for improved and more convenient rapidly-orodispersible dosage forms that can accommodate a larger assortment of API compounds, while also minimizing the waste of the API compounds themselves.

SUMMARY OF THE INVENTION

The present invention describes a porous article having one or more internal cavities disposed inside, each article comprising a bound-powder material. The bound powder material can comprise an interconnected matrix of particles of a powder material and a binder material. Each of the cavities are isolated within a portion of the interconnected matrix of the article. In articles with more than one cavity, each cavity can also be isolated from other cavities within the article. Any one or more of the internal cavities can contain one or more payload materials. The payload material can be a different composition than the composition of the bound-powder materials comprising the interconnected matrix. The description that follows pertains and is according to the present invention.

According to the present invention, the article can be a rapidly-orodispersible dosage form, such as a tablet or capsule. The bound-powder material, as well as the powder material and the binder material, can be ingestible. The payload material contained within the one or more internal cavities can comprise one or more solid medicaments, particularly powdered, particulate, crystalline or co-crystalline, hot melt extrusions, or agglomerated medicaments. The payload material contained can also comprise one or more liquid, semi-solid, paste, gel or flowable materials, any of which can be a medicament. Either or both of the matrix of the rapidly-orodispersible dosage form or the payload material within the one or more cavities can further comprise one or more pharmaceutically-acceptable excipients, non-limiting examples of which can include binders, disintegration agents, dispersants, sweeteners, glidants, flavoring agents, surfactants, humectants, preservatives, antioxidants and diluents. Further, some materials comprised within the powder material and/or binder material can have the characteristic of more than one type of excipient. As a non-limiting example, within dosage forms that comprise glycerin, the glycerin can exhibit characteristics similar to a humectant, sweetener, preservative, lubricant, saponifier, or a solvent.

Any of the rapidly-orodispersible dosage forms described herein can be formed using additive manufacturing systems, particularly three-dimensional printing (3DP) systems, using high-throughput continuous, semi-continuous, or batch manufacturing techniques, with minimal product loss, high efficiency, and high product reproducibility. Accordingly, the embodiments and features described herein provide additive manufacturing and 3DP-based methods for forming rapidly-orodispersible dosage forms having one or more internal cavities configured to contain one or more pharmaceutical medicaments and/or payloads within the dosage form.

The rapidly-orodispersible dosage forms can be formed using any conventional additive manufacturing or 3DP freeform fabrication system and/or equipment assembly that utilizes a build platform configured to build objects from a bed or other supply of powder material, particularly any of the systems or assemblies described in U.S. Pat. Nos. 6,471,992 and 8,888,480, the disclosures of which are incorporated by reference in their entireties. Upon the completion of printing, each dosage form can be separated from the unbound powder, and optionally at least a portion of the unbound powder can subsequently be recycled to form additional dosage forms or additively manufactured objects.

The rapidly-orodispersible dosage forms can be formed using any additive manufacturing or 3DP manufacturing systems and/or equipment assembles configured for the preparation of objects within a depression in a build platform, particularly any of the systems or assemblies described in U.S. Patent Pub. No. 2018/0141275, the disclosure of which is incorporated by reference in its entirety. Dosage forms can be formed by a succession of a plurality of incremental layers formed independently within each depression in the build platform, rather than in an open powder bed. Following the completion of printing, the article can be discharged from the depression, and can subsequently optionally be dried, separated from unbound powder, dedusted, and/or packaged.

The rapidly-orodispersible dosage forms can be formed using additive manufacturing or 3DP manufacturing systems and/or equipment assembles configured for forming of objects in situ within the depression of a packaging material, particularly any of the systems or assemblies described in International Patent Publication WO2020/081561, the disclosure of which is incorporated by reference in its entirety. The packaging can comprise one or more depressions, and in some embodiments, a pattern of a plurality of depressions. Non-limiting examples of such packaging are a blister pack and a disposable single-dose blister pack.

Any one of the rapidly-orodispersible dosage forms described herein can comprise a porous, durable body comprising a bound-powder material, having one or more interior cavities. The bound-powder material can comprise an interconnected matrix of at least one ingestible powder material and at least one ingestible binder material. The matrix can have a defined overall bulk density, disintegration (dispersion) time in aqueous fluid, dissolution time in aqueous fluid, and moisture content, which can be collectively tailored to provide a balance of improved chemical stability, sufficient hardness, low friability and extremely rapid dispersion time in a small volume of aqueous liquid.

The rapidly-orodispersible dosage forms are useful because they can be formed to withstand physical storage and handling, but undergo rapid dispersion/disintegration of its bound-powder matrix in the presence of a small volume of liquid. The orodispersibility of any one of the dosage forms described herein can be characterized by how quickly the dosage form disintegrates in a small amount of aqueous fluid, typically in a subject's mouth, such as water, saliva, juice, milk, beverage, body fluid, soda or a combination thereof. The dosage form can disintegrate in a small amount of water in a time ranging within 90 seconds, and by non-limiting example, within 60 seconds, within 30 seconds, within 15 seconds, within 10 seconds, and within 5 seconds. The small amount of water can be, by non-limiting example, one of at least 1 ml, at least 5 ml, or at least 10 ml, and one of up to 50 ml, up to 20 ml, up to 15 ml, up to 10 ml, up to 5 ml, and up to 1 ml. In one embodiment, the small volume of water is a sip of water, having a volume of up to 50 ml, and as little as 1 ml or less.

An ingestible powder material as described herein can comprise one or more powdered, particulate, crystalline, or agglomerated pharmaceutically-acceptable excipients, including any of the excipients listed above. In some embodiments, the one or more excipients comprising the ingestible powder material can be selected from the group consisting of a disintegration agent, a solid binder material, a dispersing material, and a glidant, including combinations thereof. A non-limiting example of an ingestible powder material is a blend comprising mannitol, microcrystalline cellulose, povidone, and colloidal silicon dioxide. In various embodiments, a portion of the ingestible powder material can comprise a medicament compound, and in some embodiments, a particulate medicament compound.

An ingestible binder material as described herein can be provided within the ingestible binding liquid, as described above, and/or within a printing liquid. In some embodiments, the binding liquid can comprise a liquid component, non-limiting examples of which include an organic solvent or water, that can dissolve and/or activate solid binder material comprised within the ingestible powder material. When a binding liquid is dispensed from a printing head, as is utilized in some 3DP-based production methods, the binding liquid can alternatively be called "printing liquid" or "printing fluid". A binding liquid or printing liquid can also comprise one or more medicaments or excipients dissolved or suspended within the liquid. In some embodiments, the one or more excipients can be a pharmaceutically-acceptable excipient, and can be selected from the group consisting of a disintegration agent, an ingestible binder material, a humectant, a sweetener or flavoring agent, a preservative, a solvent, and a surfactant, including combinations thereof. A non-limiting example of a binding liquid, which optionally can be used as a printing liquid in 3DP-based production methods, is a liquid composition comprising: water, isopropanol, glycerin, polysorbate 20, and povidone.

The one or more interior cavities as described herein can each individually have a volume in a range of at least 1%, or by non-limiting example, at least 5%, at least 10%, at least 15%, or at least 20%, or at least 25%, of the volume of the dosage form, and up to 75%, or by non-limiting example, up to 60%, up to 55%, up to 50%, of the volume of the dosage form. In an embodiment of the invention, which may be used in combination with any other embodiment described herein, the dosage form can have a single interior cavity, two interior cavities, three interior cavities, or more. The volumetric size of an interior cavity can be selected based on the overall volume and dimensions of the rapidly-orodispersible dosage form, and the desired dosage amount of a payload material to be added into the interior cavity. The volumetric size of the interior cavity can be at least 10 microliters, or at least 25 milliliters, or at least 100 milliliters, and up to about 1 milliliter, or up to about 500 microliters, or up to about 100 microliters.

The one or more payload materials or payload medicaments, as described herein, within a cavity or cavities within a dosage form, can have any mass, so long as it can be contained within its cavity, and is based on the dosage requirements of the subject. As a non-limiting example, and in another embodiment, a dosage form configured for administration to a human or other mammal can comprise one or more medicaments or other payloads having a mass in a range from at least 1 about microgram, and up to at least about 5 grams. In another embodiment, a dosage form configured for administration of a larger mass amount, for example when being administered to a large animal, non-limiting examples of which can include farm animals, such as horses or cows, or zoo animals, such as elephants or giraffes, can comprise one or more medicaments or payloads having a mass of up to 5 grams, or up to 10 grams.

In another embodiment, a dosage form can be configured for administration of a medicament or other payload that may be difficult to dose accurately in minute quantities, for instance, from at least 1 microgram and up to 1 milligram. In one non-limiting example, a stock solution of a known concentration of a medicament known to soluble within a selected printing fluid can be formulated and subsequently diluted, either when forming the printing fluid directly or in one or more dilutions prior to forming the printing fluid, to arrive at a desired concentration of the medicament within the dosage form. Similarly, and in another non-limiting example, a medicament can be combined and blended to uniformity along with one or more excipients to form a particulate mixture, which can used to form the bulk powder material used to construct a rapidly orodispersible dosage form.

A rapidly-orodispersible dosage form, as described herein, can contain one payload material comprising a medicament in a single interior cavity, or two or more payload materials, either one or more comprising a medicament in a single interior cavity, particularly when the two or more payload medicaments are inert with respect to each other and can be stored in direct contact with one another within the same cavity of the dosage form. An embodiment of a rapidly-orodispersible dosage form, which may be used in combination with any other embodiment described herein, can contain two or more payload medicaments separately in two or more interior cavities, particularly when the two or more medicaments can be administered as a co-therapy, but when stored together can react with each other or cause one of the medicaments to degrade prior to being administered. Similarly, and in various embodiments, a dosage form can contain a medicament within an interior cavity, while also containing a medicament interspersed within the powder material. In various embodiments, a medicament can be interspersed within the powder material, while a solid excipient or other material, which may otherwise react prematurely with the medicament and/or be protected from environments outside the dosage form, is contained within the interior cavity. In some embodiments of a rapidly-orodispersible dosage form, which may be used in combination with any other embodiment described herein, instead of a medicament, the rapidly-orodispersible dosage form can contain a placebo material within one or more interior cavities, the placebo material intended to mimic the taste, texture, and overall experience of a rapidly-orodispersible dosage form containing a medicament, but without having a pharmacologic effect. The placebo material can be an unbound powder material having the same composition as the ingestible powder material in the bound-powder matrix.

In some embodiments, a rapidly-orodispersible, unitary, partially-enclosed dosage form is provided, having an internal cavity, comprising a container body with a unitary lid that encloses an internal cavity within the dosage form, and having a port opening within and through the container body (for example, through the base or the peripheral wall) or the unitary lid. The port opening is in fluid communication with the one or more internal cavities formed within the container body. The port opening is typically that a portion of the lid, or that portion of the container body, when being formed from build powder material, where the particulate build powder material was left unbound (for example, not contacted with printing or binding liquid) during the forming of the bound powder matrix of the lid or the container body. Once the lid and container body have been formed, the unbound build powder in the portion of the lid or the container body is removed to form the port opening. Any unbound powder material contained within the one or more interior cavity(ies) of the container body can be evacuated through the port opening.

The effective size or diameter of the port opening can be as large as needed to evacuate unbound build powder than might be trapped inside the cavity of the partially-enclosed dosage form, following its manufacture, and can be as minimal in size or diameter as possible to simplify or improve the subsequent closing and/or sealing of the port opening, once most or all of the unbound powder material has been evacuated, and the payload material deposited into the internal cavity of the dosage form. The cross-sectional size of the port opening is typically sufficient in effective size or diameter to evacuate the unbound powder material from the interior cavity by air fluidizing, vacuuming, or pouring the unbound powder material out through the port opening, and sufficient in size to permit filling the evacuated interior cavity with a payload material. The partially-enclosed dosage form with the payload material deposited within the cavity can then be closed and sealed, by inserting or depositing within the port opening a suitable water-soluble or ingestible material. A rapidly-orodispersible, unitary, partially-enclosed dosage form can be prepared in an open print bed of a 3DP assembly, or within a depression of a dosage form package, such as a blister package, or within a fixed-volume or variable-volume mold cavity.

In some embodiments of a rapidly-orodispersible dosage form, which may be used in combination with any other embodiment described herein, a rapidly-orodispersible dosage form can additionally comprise a dissolvable barrier material, applied or coated onto at least a portion of an interior surface of the dosage form that forms a boundary for the one or more interior cavities. The dissolvable barrier material can be disposed between the contents of an interior cavity and the bound-powder material comprising the matrix, to inhibit or prevent the contents of the interior cavity from migrating into the bound-powder material, and potentially out of the dosage form altogether. The dissolvable barrier material is selected from the group consisting of water-soluble diluents, water-soluble binders, water-soluble film-formers, and water-soluble gelling agents, and combinations thereof. The dissolvable barrier material can comprise mannitol, sorbitol, xylitol, lactitol, erythritol, isomalt, povidone, copovidone, hydroxypropylcellulose, hydroxypropylmethylcellulose, carboxymethylcellulose, gelatin, casein, agar, guar gum, gellan gum, xanthan gum, locust bean gum, alginate, carrageenan, hydroxypropyl starch, pregelatinized starch, poloxamer, polyethylene glycol, polydextrose, or polyvinyl alcohol, including derivatives and/or combinations thereof.

In some embodiments of a rapidly-orodispersible dosage form, which may be used in combination with any other embodiment described herein, the rapidly-orodispersible dosage form can be formed into any three-dimensional geometric shape. In some embodiments, the dosage form can be in the shape of an irregular or regular polyhedron, a prism having an "n" number of regular faces; for example, 3, 4, 5, 6, or 8 regular faces, a prismatoid, a prismoid, a scutoid, a frustum, such as a pyramidal frustum, a conical frustum, a spherical frustum, and frustoconical sections. Non-limiting examples of dosage form shapes can include square, circular and elliptical cylinders. In other embodiments, a rapidly-orodispersible dosage form can have one or more rounded surfaces, such as, as non-limiting examples, top and/or bottom rounded surfaces, including spherical, ellipsoidal, and/or spherocylindrical (capsular) shaped surfaces. In particular, rapidly-orodispersible dosage forms formed with rounded surfaces, particularly spherocylindrical dosage forms, can be formed to mimic the capsular and ellipsoidal shapes of other common prescribed and over-the-counter medications. Those skilled in the art would appreciate that the above examples are non-limiting, and that there are an infinite number of shapes into which each dosage form can be constructed.

In some embodiments, which may be used in combination with any one or more of the embodiments described above and herein, the rapidly-orodispersible dosage form can be formed into a unitary dosage form, comprising a single bound-powder matrix that envelops and isolates one or more interior cavities. The unitary dosage form can have one, two, three, or more internal cavities. A unitary dosage form or tablet has a matrix that is formed completely from a plurality of bound powder layers, each bound powder layer formed by placing a layer of a powder material over a previously-formed bound powder layer, and selectively binding the powder material together and to the previously-formed bound powder layer, to form a next bound powder layer.

In some embodiments, which may be used in combination with any one or more of the embodiments described above and herein, the rapidly-orodispersible dosage form can comprise two separate bodies, including a container body and a lidding body, that are secured together to form a two-piece tablet having one or more internal cavities. The container body can comprise and be formed using a first bound-powder material, and the lidding body can comprise and be formed using a second bound-powder material. The first bound-powder material can comprise an interconnected matrix of a first powder material and a first binder material, and the second bound-powder material can comprise a second powder material and second binder material. The first powder material and the second powder material, and the first binder material and the second binder material, can be selected from the group consisting of any of the powder materials and binder materials, respectively, described above. In some embodiments, the first bound-powder material and the second bound-powder material can comprise the same composition.

According to the present invention, a container body can have one or more cavities, and include a base and a peripheral wall extending from the base and having an inner surface, an upper surface, and an external surface. The one or more cavities within the container body are bounded by the base and the inner surface of the peripheral wall.

According to the present invention, a lidding body can have an undersurface configured to be positioned over the upper surface of the peripheral wall, covering the one or more cavities to form internal cavities. In some embodiments, which may be used in combination with any one or more of the embodiments described above and herein, the undersurface of the lidding body can comprise a peripheral portion and an interior portion, the interior portion including a projection portion. The projection portion can extend below the peripheral portion and have an annular outer surface that is frictionally engaged with a portion of the inner surface of the peripheral wall. The lidding body can have a perimeter wall extending from the peripheral portion of the undersurface, the perimeter wall having a bottom surface and an inner surface, wherein the inner surface of the perimeter wall of the lidding body is frictionally engaged with at least a portion of the external surface of the peripheral wall of the container body. In a further embodiment, the perimeter wall of the lidding body can extend along and frictionally engage with the entire length of the peripheral wall of the container body, giving the dosage form a planar bottom surface defined by the base of the container body and the bottom surface of the perimeter wall of the lidding body.

In some embodiments, which may be used in combination with any one or more of the embodiments described above and herein, the means for securing the lidding body to the container body can comprise an adhesive material disposed between at least a portion of the undersurface of the lidding body and the upper surface of the peripheral wall of the container body. The adhesive material can be disposed between at least a portion of the annular outer surface of the projection portion of the lidding body and the inner surface of the peripheral wall of the container body. The adhesive material can be disposed between the external surface of the peripheral wall of the container body and the inner surface of the perimeter wall of the lidding body that overlaps the container body. In some embodiments, which may be used in combination with any one or more of the embodiments described above and herein, the adhesive material can be disposed between one or more localized or selected portions of any of the surfaces above. In one non-limiting example, the adhesive material can be applied intermittently and non-contiguously across one or more of the surfaces, in an amount sufficient to secure the lidding body and the container body together. In another non-limiting example, the adhesive material can be applied continuously along the circumference of the undersurface of the lidding body and/or the upper surface of the peripheral wall of the container body, in order to form a seal between the lidding body and the container body in the assembled dosage form.

An adhesive material can be selected from the group consisting of water-soluble diluents, water-soluble binders, water-soluble film-formers, and water-soluble gelling agents, including combinations thereof. Non-limiting examples of adhesive materials include mannitol, sorbitol, xylitol, lactitol, erythritol, isomalt, povidone, copovidone, hydroxypropylcellulose, hydroxypropylmethylcellulose, carboxymethylcellulose, gelatin, casein, agar, guar gum, gellan gum, xanthan gum, locust bean gum, alginate, carrageenan, hydroxypropyl starch, pre-gelatinized starch, poloxamer, polyethylene glycol, polydextrose, or polyvinyl alcohol, or derivatives thereof, and combinations thereof. In some embodiments, which may be used in combination with any one or more of the embodiments described above and herein, the adhesive is moisture-activated and is applied as a solution, dispersion, or gel. In some embodiments, which may be used in combination with any one or more of the embodiments described above and herein, the adhesive is moisture-activated and is applied as a solution, dispersion, or gel via inkjet printhead.

In some embodiments, which may be used in combination with any one or more of the embodiments described above and herein, the adhesive material can be a thermally-activated adhesive material, in which the adhesive material is disposed one or both of the undersurface of the lidding body and the upper surface of the peripheral wall, but the lidding body and the container body are not adhered to each other until the two bodies are heated and/or activated by a wavelength of light, particularly infrared light. In some embodiments, which may be used in combination with any one or more of the embodiments described above and herein, the adhesive material can be applied as a melt (or thermally softened material) to one or both of the undersurface of the lidding body and the upper surface of the peripheral wall of the container body, or otherwise to a seam defined by the intersection of the lidding body and container body.

The thermally-activated adhesive material can be selected from the group consisting of water-soluble diluents, water-soluble binders, water-soluble film-formers, and water-soluble gelling agents, including combinations thereof, that exhibit sufficient chemical stability during melt application or thermally-softened application. Non-limiting examples of thermally-activated adhesive materials include mannitol, sorbitol, xylitol, lactitol, erythritol, isomalt, povidone, copovidone, hydroxypropylcellulose, a poloxamer, polyethylene glycol, or polyvinyl alcohol, or derivatives thereof, and combinations thereof.

In some embodiments, which may be used in combination with any one or more of the embodiments described above and herein, the lidding body is secured to the container body via application of a laser to selectively melt, soften, sinter, and/or fuse the material along a seam defined by the intersection of the lidding body and container body.

In some embodiments, which may be used in combination with any one or more of the embodiments described above and herein, the means for securing the lidding body to the container body can comprise a first mechanical securement on the upper surface of the peripheral wall and a second mechanical securement on the lidding body, which are mated with each other to mechanically secure the lidding body to the container body. The second mechanical securement can be disposed on the undersurface of the lidding body. The first mechanical securement and the second mechanical securement can be configured to increase the surface area of the contact surface between the lidding body and the container body, providing an enhanced frictional engagement and/or additional surfaces upon which to apply an adhesive material. The first mechanical securement can comprise one or more valleys formed into the peripheral portion of the upper surface of the peripheral wall, the second mechanical securement can comprise one or more peaks formed upon the peripheral portion of the undersurface of the lidding body, and the one or more peaks of the lidding body are in register with and secured to the one or more valleys of the container body. Alternatively, the first mechanical securement can comprise one or more peaks formed upon the peripheral portion of the upper surface of the peripheral wall, the second mechanical securement can comprise one or more valleys formed into the peripheral portion of the undersurface of the lidding body, and the one or more peaks of the container body are in register with and secured to the one or more valleys of the lidding body. In some embodiments, which may be used in combination with any one or more of the embodiments described above and herein, an adhesive material can also be disposed between a portion of the first mechanical securement and the second mechanical securement, as well as between other contact surfaces between the container body and the lidding body.

The present invention also provides a method for forming a rapidly-orodispersible container, which can be utilized to form any of the unitary and two-piece dosage forms described above. A method for forming a rapidly-orodispersible container having a cavity for containing a medicament or other payload can comprise the steps of: forming a rapidly-orodispersible container base; forming a rapidly-orodispersible peripheral wall; and removing the unbound powder material from the filled container, thereby forming the rapidly-orodispersible container having a cavity. The method for forming the container base can comprise the steps of: a) dispensing a powder material into a base powder layer; b) dispensing a binding liquid onto the base powder layer to form a bound base-matrix layer; and c) optionally repeating steps a) and b) one or more times.

In some embodiments, which may be used in combination with any one or more of the embodiments described above and herein, the method for forming the peripheral wall can comprise the steps of: d) dispersing the powder material into an intermediate powder layer atop the container base; e) dispensing the binding liquid onto a peripheral portion of the intermediate powder layer, without dispersing the binding liquid onto an interior portion of the intermediate powder layer, to form a filled container consisting of a bound wall-matrix layer that is bound to the container base, and an interior portion consisting of unbound powder material; and f) optionally repeating steps d) and e) one or more times.

In some embodiments, which may be used in combination with any one or more of the embodiments described above and herein, the step of removing the unbound powder material comprises the sub-steps of: providing a vacuum system comprising an air inlet and an air drawing means for drawing an ambient air into the air inlet; positioning the air inlet over the filled container; drawing ambient air into the positioned air inlet to fluidize the unbound powder material within the filled container; and drawing the unbound powder into the air inlet with the ambient air. The step of removing the unbound powder material comprises the sub-steps of inverting the filled container and decanting the unbound powder material from the filled container. The method for forming the container body can further comprise the steps of: recovering the removed unbound powder material using a powder recovery system, and returning the unbound powder material to a powder reservoir. The rapidly-orodispersible container can be formed into any open three-dimensional shape with a cavity formed into the shape's top surface. The rapidly-orodispersible container is in the shape of either an open cylinder or an open frustoconical section.

In some embodiments, which may be used in combination with any one or more of the embodiments described above and herein, a rapidly-orodispersible unitary dosage form can be formed from any of the rapidly-orodispersible containers described above. A method for forming a unitary rapidly-orodispersible dosage form can comprise the steps of: i) forming any of the rapidly-orodispersible containers described above; ii) dispersing one or more payload materials into the cavity; iii) forming an upper layer of powder material over the cavity and the one or more particulate materials within the cavity, and over the upper surface of the container peripheral wall; iv) dispensing a binding liquid onto a portion of the upper layer of powder material, to form a bound-powder upper layer atop the cavity, forming or enclosing the interior cavity; and v) optionally performing steps iii) and iv) one or more times, thereby forming the rapidly-orodispersible dosage form containing a payload material within the cavity. In various embodiments, the payload material contained within the unitary dosage form comprises one or more medicaments, and in various embodiments, a solid or particulate medicament. In various embodiments, the payload material contained within the unitary dosage form comprises one or more placebo materials, such as unbound powder material as a non-limiting example. In various embodiments, the payload material contained within the unitary dosage form comprises one or more solid excipients.

According to the present invention, a one or more solid or particulate payload material comprises, or consists essentially of, or consists of, a medicament. In some embodiments, which may be used in combination with any one or more of the embodiments described above and herein, the one or more particulate payload material comprises the medicament and one or more of any of the excipients described above. The one or more excipients can comprise a powder material having the same composition as the powder material in the bound-powder matrix. In another embodiment, the one or more excipients can consist of a powder material having the same composition as the powder material in the bound-powder matrix. In another embodiment, the payload comprising a medicament can be provided in the form of engineered particles made via spray drying, coating, granulation, chemical complexation, co-crystallization, or combinations thereof. In some embodiments, which may be used in combination with any one or more of the embodiments described above and herein, the one or more particulate payload material can be dispensed into the cavity until the cavity is completely filled. In another embodiment, the one or more particulate payload material dispensed into the cavity can partially fill the cavity. Upon partially filling the cavity with the one or more particulate payload material, one or more filler materials can be dispensed into the cavity and atop the payload material until the cavity is filled or completely filled. In an embodiment, the one or more filler materials can provide a physical and/or chemical barrier between the medicament or other payload material and the upper layer of powder material that encloses the cavity. The one or more filler materials can be selected from the group consisting of: calcium carbonate, calcium lactate, calcium phosphate, calcium silicate, calcium sulfate, cellulose, dextrose, erythritol, isomalt, lactitol, lactose, magnesium carbonate, magnesium oxide, maltodextrin, maltose, mannitol, microcrystalline cellulose, polyethylene glycol, sodium bicarbonate, sodium carbonate, sodium chloride, sorbitol, starch, sucrose, talc trehalose, and xylitol, including combinations thereof. In another embodiment, the filler material can be a superdisintegrant, which can be utilized to enhance the orodispersibility of the dosage form. A superdisintegrant can be selected from the group consisting of carboxymethylcellulose sodium, croscarmellose sodium, sodium starch glycolate, and crospovidone, including combinations thereof. In a non-limiting example, a cavity partially-filled with a particulate composition consisting of, or consisting essentially of, a medicament, can be filled by dispensing a quantity of an unbound powder material, the unbound powder material having the same composition as the powder material in the bound-powder matrix, prior to forming the upper layer of powder material over the filled cavity and upper surface of the container peripheral wall.

According to the present invention, a rapidly-orodispersible two-piece dosage form comprising a container body and a lidding body can be formed from any of the rapidly-orodispersible containers described above, using a method comprising the following steps: (a) providing a porous, durable container body made of a first bound-powder material, the container body having a base, a peripheral wall extending from the base and having an inner surface, an upper surface, and an external surface, the container body having one or more cavities bounded by the base and the inner surface of the peripheral wall; (b) providing a porous, durable lidding body comprising a second bound-powder material; (c) dispensing a solid medicament or other payload material into the cavity; (d) placing the lidding body onto the upper surface of the peripheral wall, to form an internal cavity containing the solid medicament or other payload material; and (e) securing the lidding body to the container body, thereby forming the rapidly-orodispersible dosage form. In various embodiments, the particulate material contained within the two-piece dosage form comprises one or more medicaments. In various embodiments, the particulate material contained within the two-piece dosage form comprises one or more placebo materials, such as unbound powder material as a non-limiting example. In various embodiments, the particulate material contained within the two-piece dosage form comprises one or more solid excipients.

According to the present invention, a method for forming the lidding body can utilize similar steps as described above for forming a container base, namely: dispersing a powder material into a powder layer; dispensing a binding liquid onto the powder layer to form a bound-matrix layer; and optionally repeating the above steps one or more times to form the lidding body. The undersurface of the lidding body can comprise a peripheral portion and an interior portion, the interior portion including a projection portion, wherein the projection portion extends below the peripheral portion and has an annular outer surface, and when the lidding body is placed onto the upper surface of the peripheral wall, the projection portion extends into a portion of the interior cavity and the annular outer surface of the projection portion frictionally engages with a portion of the inner surface of the peripheral wall. The lidding body can have a perimeter wall extending from the peripheral portion of the undersurface, the perimeter wall having a bottom surface and an inner surface, wherein when the lidding body is secured to the container body, the inner surface of the perimeter wall of the lidding body is frictionally engaged with at least a portion of the external surface of the peripheral wall of the container body. As described above, the inner surface of the perimeter wall of the lidding body can frictionally engaged with the entire external surface of the peripheral wall of the container body, in order to form a planar bottom surface of the rapidly-orodispersible dosage form.

According to the present invention, at least one of the container body and the lidding body further comprises an adhesive material, the adhesive material applied to at least a portion of a surface selected from the group consisting of: the upper surface of the peripheral wall; the inner surface of the peripheral wall; the peripheral portion of the undersurface of the lidding body; the annular outer surface of the projection portion; the external surface of the peripheral wall of the container body; and the inner surface of the perimeter wall, including combinations thereof. The step of securing the lidding body comprises adhering the lidding body to the container body. The adhesive compound can be any of the adhesive compounds described above, including combinations thereof.

In another embodiment, the step of securing the lidding body to the container body comprises the following sub-steps: forming a first mechanical securement on the upper surface of the peripheral wall of the container body; and forming a second mechanical securement on the lidding body, wherein the first mechanical securement is configured to mate and frictionally engage with the second mechanical securement to secure the lidding body mechanically to the container body. The first mechanical securement and the second mechanical securement can comprise any set of complementary structures that can mate together to mechanically secure the lidding body to the container body. The first mechanical securement and the second mechanical securement can comprise any combination of peaks and valleys on the underside of the lidding body and the upper surface of the peripheral wall as described above. The first mechanical securement comprises one or more valleys formed into the upper surface of the peripheral wall of the container body, the second mechanical securement comprises one or more peaks formed into the peripheral portion of the undersurface of the lidding body, at least one of the one or more valleys and the one or more peaks further comprise an adhesive material applied thereto; and the step of securing the lidding body to the container body comprises the sub-steps of: mating the one or more peaks of the lidding body with the one or more valleys of the container body, and adhering the lidding body to the container body.

Thermally-Formed Dosage Forms

In various embodiments, the matrix of in various embodiments of a porous article, and in the matrix of other various embodiments, a unitary dosage form or the container body and/or the lidding body of a two-piece dosage form, can substantially be formed without the use or with the minimal use of printing liquids or other solvents, using a thermal means. The thermal means can include selective or targeted application of heat energy (in a non-limiting example, a directed laser, using techniques used in processes such as selective laser sintering or selective laser melting), or bulk techniques such as heating in a mold. In various embodiments, the matrix can be formed by depositing and/or forming a layer of a thermofusable powder material, and to activate the thermofusable powder material into a bound matrix. In some embodiments, the bound matrix can also be described as a granular agglomerate. Methods and apparatuses that utilize a thermofusable powder material to form abound matrix can involve the spreading of the thermofusable powder material into a layer, including over a previous layer or layers, and the matrices can be formed matrix directly within a dosage form package, such as a blister package, or within a fixed-volume or variable-volume mold cavity.

Where the present description teaches and describes depositing and/or forming a layer of powder material, and subsequently selectively wetting and binding the powder material using a binding liquid, alternatively such methods and techniques, and any apparatus and system to deposit and/or form the layer of powder material, can be used for forming or depositing a layer of the thermofusable powder material, and selectively activate the thermofusable powder material to forming a selected portion or portions, or all, of the layer of thermofusable powder material into one or more portions, or all, of a bound matrix or granular agglomerate.

In one non-limiting example, a method for thermally forming a rapidly-orodispersible container having a cavity for containing a medicament or other payload material can comprise the steps of: thermally forming a rapidly-orodispersible container base; thermally forming a rapidly-orodispersible peripheral wall; and removing the unbound powder material from the formed container, thereby forming the rapidly-orodispersible container having a cavity. The method for thermally forming the container base can comprise the steps of: a) dispensing a thermofusable powder material into a base powder layer, the thermofusable powder material comprising a thermal binder; b) applying a directed heat energy onto the base powder layer to thermally activate the thermal binder, forming a bound base-matrix layer; and c) optionally repeating steps a) and b) one or more times on top of the bound base-matrix layer. In some embodiments, which may be used in combination with any one or more of the embodiments described above and herein, the method for thermally forming the peripheral wall can comprise the steps of: d) dispersing the thermofusable powder material into an intermediate powder layer atop the container base; e) applying a directed heat energy onto a peripheral portion of the intermediate powder layer to activate the thermal binder in the peripheral portion, without applying a heat energy onto an interior portion of the intermediate powder layer; and f) optionally repeating steps d) and e) one or more times on top of the bound wall-matrix layer, to form a powder-filled container consisting of a bound wall-matrix layer that is bound to the container base, and an interior portion containing unbound powder material.

In various embodiments, the thermofusable powder material comprises a thermal binder in particle or fibrous form. Once the thermofusable powder material is disposed within a layer, typically having a uniform thickness, the layer can be heated across its entire surface area, or at preselected portions of the surface area, in order to soften or melt the particles of the thermal binder. The heated portion(s) of the thermofusable powder material can form a bound matrix both within and below the pre-selected portions of the surface area, while leaving unbound any remaining inactivated thermofusable powder material in a portion or portions of the layer that were not heated.

In various embodiments, particles comprised within a layer of thermofusable powder material can be selectively joined by exposure to laser radiation. Laser radiation exposed to pre-determined and selected areal portions of the layer can melt or liquify (fully or partially) the thermal binder within the thermofusable powder material, binding together the thermofusable powder in such selected portion(s) into a bound powder portion of particulate agglomerate. Other areal portions of the thermofusable powder that are not exposed to laser radiation can be left unbound. Afterward, the exposed bound portion(s) are allowed to cool until the melted or softened thermal binder has hardened and/or solidified, leaving a processed layer of a material that comprises unbound thermofusable powder in some areal portions, and particulate agglomerate bound by the thermal binder in the remaining areal portions. Alternatively, the entire surface area of a thermofusable powder material layer can be formed into a particulate aggregate. Steps of spreading a further amount of the thermofusable powder material atop of a processed layer and exposing the thermofusable powder material to laser radiation are repeated, layer-by-layer, until the formation of the container body, lidding body, and/or dosage form is complete, the completed article consisting of a bound matrix of the particulate agglomerate. In particular, completed containers can consist of one or more interior cavities, with each interior cavity containing unbound thermofusable powder material.

In various embodiments, the thermofusable powder material comprises a mixture comprising one or more thermal binders, at least one carbohydrate or carbohydrate alcohol, and optionally one or more excipients, medicaments and/or payload materials.

In various embodiments, the thermal binder has a glass transition temperature at which the thermal binder, and at least the outer surface thereof, softens and can cohesively contact with adjacent particulate material of the thermofusable powder material. In various embodiments, the thermal binder can comprise two or more thermal binders, in which each thermal binder can have its own independent glass transition temperature, weight, and mean or average particle size distribution. The binding capacity for any thermal binder material within a thermofusable powder material can increase or decrease as a function of its weight content, particle size distribution, glass transition temperature, and the heated temperature to which it is activated. The thermal binder will typically have a glass transition temperature that is less than a glass transition temperature of the one or more other particulate components of the thermofusable powder material, such as the carbohydrate or carbohydrate alcohol and one or more excipients, medicaments and/or payload materials. Preferably the glass transition temperature of the thermal binder is at least 2° C., and more preferably at least 5° C., lower than that of the other particulate components within the thermofusable powder material. This allows the other particulate components of the thermofusable powder material to remain solid while the thermal binder material softens and/or melts, to contact and/or spread into contact with the remaining bulk powder.

In various embodiments, a portion or an entire layer of thermofusable powder material can be uniformly heated to a staging temperature that is below, though typically close to, the glass transition temperature of any thermal binder contained within the thermofusable powder material. At the staging temperature, the thermal binder material and the other particulate components remain solid and free-flowing. By raising the temperature of a layer of thermofusable powder material, or a portion thereof, to the staging temperature, the intensity and duration of heat applied by the heat source can be minimized when the heat source is directed at the pre-selected surface area of the layer of thermofusable powder material. As a result, the temperature of the thermofusable powder layer can more efficiently be raised only at pre-selected portions of the surface area to approach an activating temperature at or near the glass transition temperature of a thermal binder, while the portions that aren't selected remain at, or near to, the staging temperature. Upon reaching the activation temperature, the activated thermal binder can begin to soften, melt, and cohesively bind to adjacent particulate components in the thermofusable powder material that remain solid, in order to form a bound matrix.

In another embodiment, the thermal means can comprise a heat source that directs heat energy at the areas to be bonded, while shielding the delivery of the heat energy at or onto areas of the thermofusable powder layer that are to remain unbonded and un-agglomerated. Non-limiting examples of such directing heat energy can include a radiant source, convective heating, radiofrequency heating, sonic heating, or microwave heating, while a shielding means can include an areal template that is applied upon to cover the surface of the portion of the layer of thermofusable powder that is to remain unbound. Templates can be comprised of one or more materials can reflect away or absorb the heat energy, in order to prevent or greatly restrict its penetration therethrough to the powder material beneath.

In various embodiments, a suitable heat source can be directed to heat selected portions or specific planar surfaces of the thermofusable powder material layer, with high resolution, in order to avoid heating unintended portions of the powder layer which are to remain un-agglomerated. A non-limiting example of a suitable heat source can be a radiant heater, conductive heating, convective heating, radiofrequency heating, sonic heating, microwave heating, or laser heating. In various embodiments, the heat source includes a means for selectively directing the heat energy for increasing the temperature of the thermofusable powder material only upon and into the planar portion of the layer of powder that is to be thermally bonded, while limiting or preventing the heat energy upon or into the remaining planar portions of the layer of powder that are to remain unbonded and un-agglomerated.

In one embodiment, said means can comprise a targeting heat source that targets heat energy only at the areas of the thermofusable powder layer to be bonded. A non-limiting example of such targeting heat energy is a laser heat source.

BRIEF DESCRIPTION OF THE FIGURES

FIG. 17 shows a sectional view of a container body formed within a depression as shown in FIG. 6, on which one (or more) incremental layer of powder material is deposited.

FIG. 18 illustrates the forming, for example with a binding liquid, a lid for the container body having an area of unbound powder material to form a port opening, and the container body having an internal cavity filled with unbound powder material.

FIG. 19 shows a sectional view of the formed unitary, partially-enclosed dosage form of FIG. 18 with the unbound powder material being evacuated from the cavity through the port opening in the lid.

FIG. 20 shows a means for partially or completely filling the empty cavity of the container body of FIG. 18, through the port opening in the lid, with a payload material.

FIG. 21 shows the closing and sealing of port opening in the lid, to form the filled-and-sealed dosage form having a cavity containing the payload material.

FIG. 22 shows an exploded view of an elongated container body having a circular upper surface and an elongated lidding body having a circular undersurface that is the same size as the upper surface of the container body.

FIG. 23 shows a perspective view of a spherocylindrical, two-piece dosage form assembled from the container body and lidding body of FIG. 22.

FIG. 24 shows an exploded view of a container body having an elliptical upper surface and a lidding body having an elliptical undersurface that is the same size as the upper surface of the container body.

FIG. 25 shows a perspective view of an ovoid, two-piece dosage form assembled from the container body and lidding body of FIG. 24.

FIG. 26 shows an exploded view of a container body having a rectangular upper surface and a lidding body having a rectangular undersurface that is the same size as the upper surface of the container body.

FIG. 27 shows a perspective view of a cuboid, two-piece dosage form assembled from the container body and lidding body of FIG. 26.

FIG. 40 shows an open print bed apparatus, with a build plate superposed on a height-adjustable platform.

FIG. 41 shows the processing of dosage forms in a first series of steps, for forming a plurality of bases for the container bodies, by lowering the build plate to provide a cavity, placing a layer of powder within the cavity upon the upper surface of the build plate, and depositing a binding liquid onto selected portions of the powder layer to form a plurality of bases consisting of the bound powder matrix.

FIG. 42 shows the processing of dosage forms in a second series of steps, for forming a plurality of peripheral walls for the container bodies, by lowering the build plate to provide a cavity, placing a layer of powder within the cavity upon the previous layer of unbound powder and bound powder bases, depositing a binding liquid onto selected portions of the powder layer to form a plurality of peripheral walls consisting of the bound powder matrix, upon the plurality of bases.

FIG. 43 shows the processing of dosage forms in a third series of steps, for completing the plurality of peripheral walls for the container bodies, by lowering the build plate to provide a cavity, placing a layer of powder within the cavity upon the previous layer of unbound powder and bound-powder peripheral walls, depositing a binding liquid onto selected portions of the powder layer to form a plurality of upper portions of the peripheral walls consisting of the bound powder matrix.

FIG. 44 shows the processing of dosage forms in a fourth series of steps, for evacuating the unbound powder from within the peripheral walls of the container bodies, and depositing a particulate payload material to fill the evacuated container bodies.

FIG. 45 shows the processing of dosage forms in a fifth series of steps, for forming a plurality of container tops for the filled container bodies, by lowering the build plate to provide a cavity, placing a layer of powder within the cavity upon the previous layer of unbound powder and filled container bodies, depositing a binding liquid onto selected portions of the powder layer to form a plurality of container tops consisting of the bound powder matrix, upon the plurality of filled container bodies, to form a plurality of dosage forms.

FIG. 46 shows an alternative process for evacuating the unbound powder from within the peripheral walls of the container bodies, and depositing a particulate payload material to fill the evacuated container bodies.

FIG. 49 shows a sectional view of a container body formed from a plurality of incremental layers of build powder material, having a base and a peripheral wall, with an open cavity bounded by the peripheral wall that is filled with the build powder material. A plurality of the container bodies being processed in an open print bed is shown in FIG. 43 at step D3.

Figure 50:
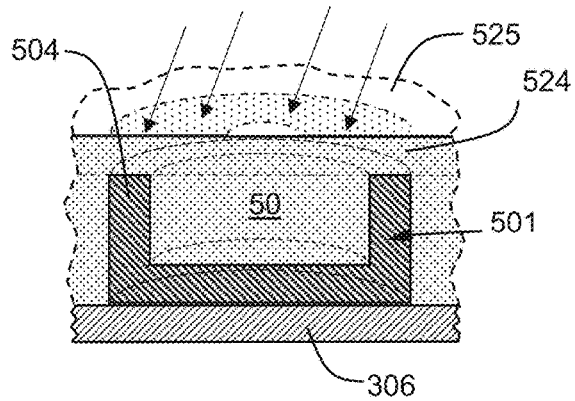

In the present embodiment, as illustrated in FIG. 50, the build plate 306 is lowered an incremental distance, and one (or more) substantially uniform, incremental layer of build powder material is applied over the formed container body and build powder material, and an area on the upper surface of the build powder layer illustrates where a printing liquid will be directed.

Figure 51:
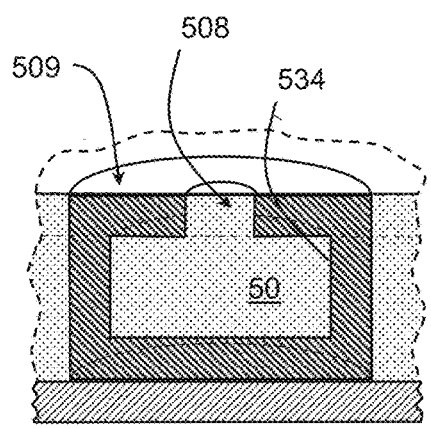

FIG. 51 shows a sectional view of the formed unitary, partially-enclosed dosage form having an internal cavity filled with unbound powder material, and a top lid formed from the selected printing of the layer of build powder material, the top lid having a port opening formed from unwetted and unbound build powder.

Figure 52:
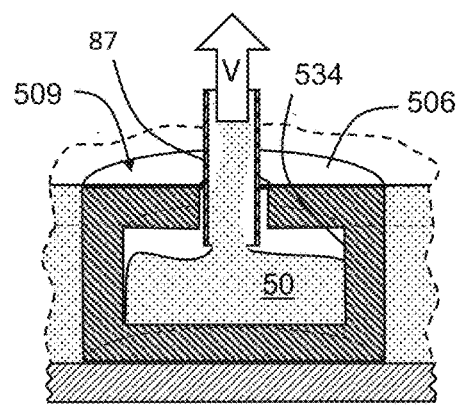

FIG. 52 shows the use of an evacuation system to remove the unbound powder material from within the cavity through the port opening.

Figure 53:
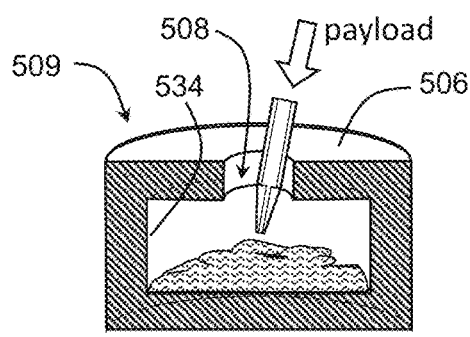

FIG. 53 shows a means for partially or completely filling the empty cavity of the partially-enclosed dosage form with a payload material.

Figure 54:
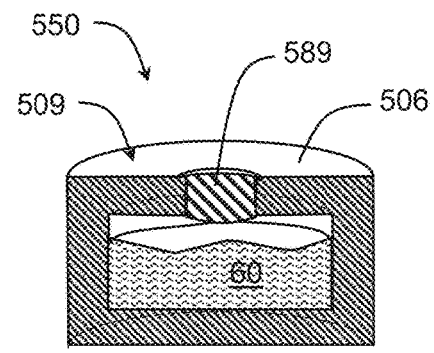

FIG. 54 shows the closing and sealing of port opening in the lid, to form the filled-and-sealed dosage form.

Figure 55:
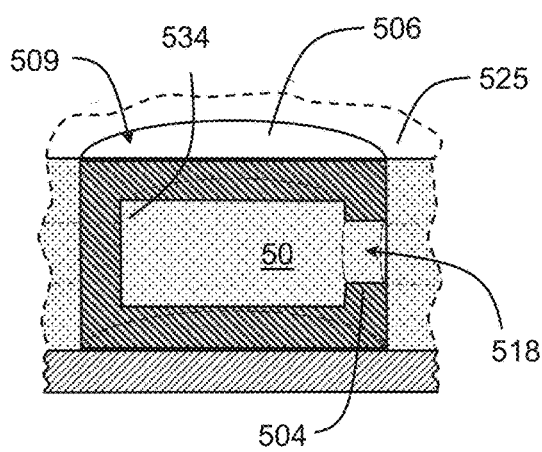

FIG. 55 shows an alternative embodiment of a unitary, partially-enclosed dosage form with a port opening formed in a peripheral wall of the container body.

Figure 56:
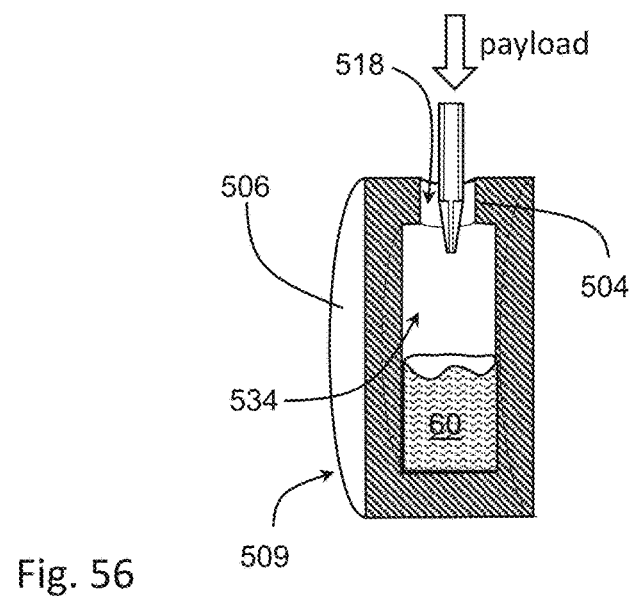

FIG. 56 shows the unitary, partially-enclosed dosage form of FIG. 55 being filled with a payload through the port opening in the peripheral wall of the container body.

Figure 43:
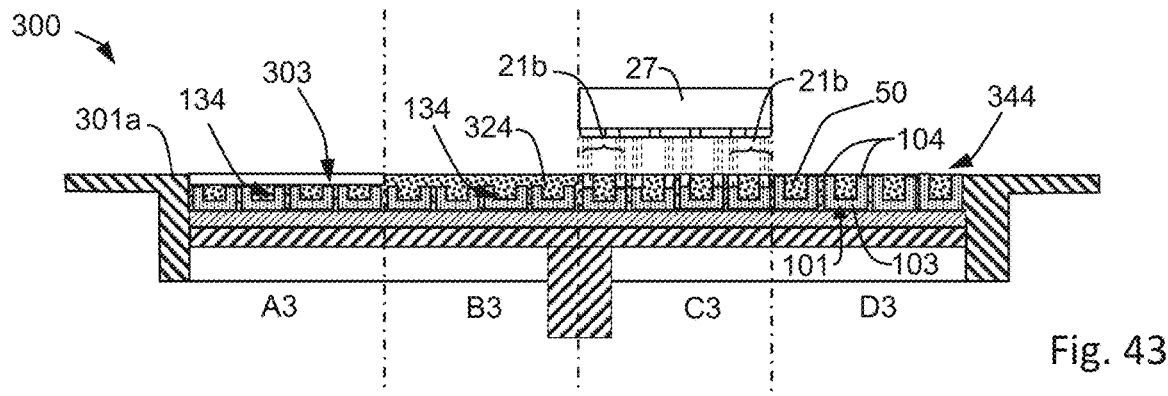
Figure 57:
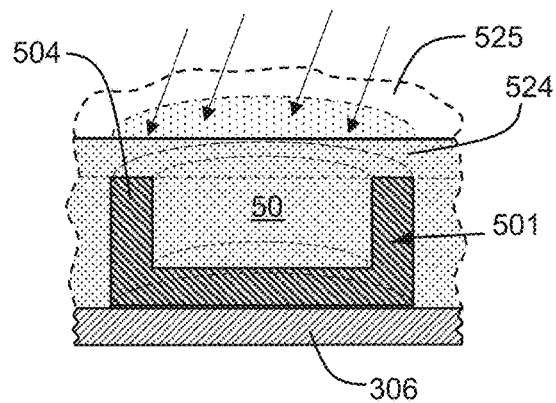

FIGS. 57-60 illustrate the forming, filling and sealing of an alternative embodiment of a unitary dosage form having an internal cavity and port opening in a peripheral wall of the container body. FIG. 57 shows a sectional view of a container body formed from a plurality of incremental layers of build powder material, having a base and a peripheral wall, and one (or more) substantially uniform, incremental layer of build powder material is applied over the formed container body and build powder material. A plurality of the container bodies being processed in an open print bed is shown in FIG. 43 at step D3.

Figure 58:
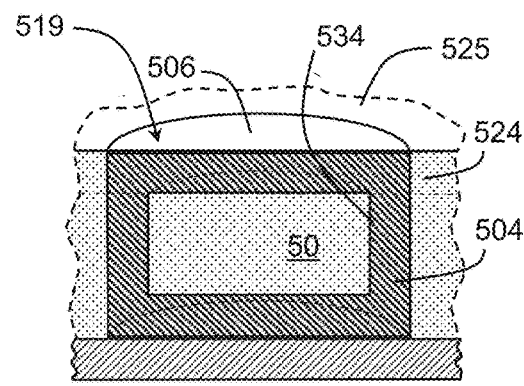

FIG. 58 illustrates a unitary top formed onto the container body by printing the build powder layer, enclosing unwetted build powder within the internal cavity of the container body.

Figure 59:
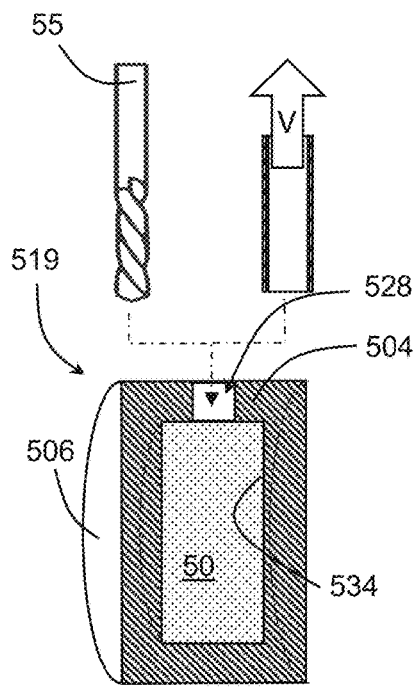

FIG. 59 illustrates forming a port opening into the peripheral side wall with a boring means, and a means for evacuating the unwetted build powder from within the cavity.

Figure 60:
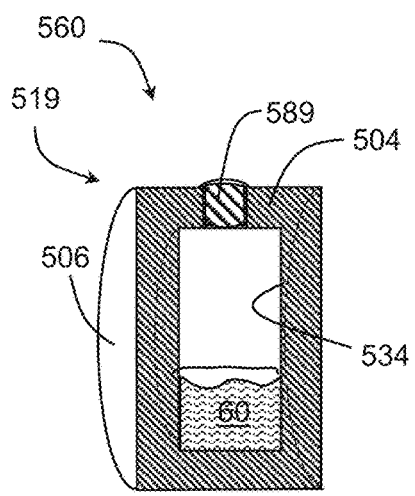

FIG. 60 shows a finished dosage article following the deposit of a payload material through the port opening and into the internal cavity of the dosage form, and sealing of the port opening.

Figure 61:
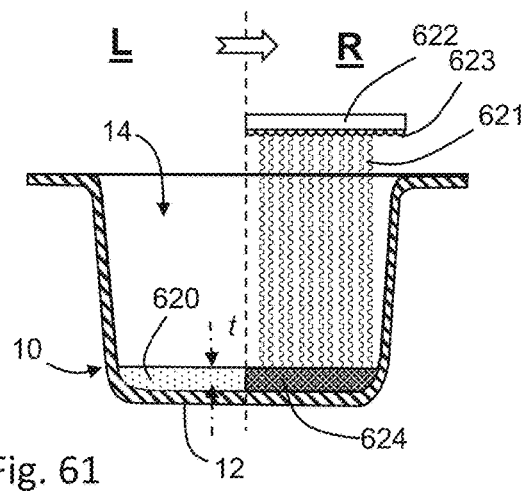

FIG. 61 illustrates on the left side, L, a first layer of a thermofusable powder material formed within the base of a depression of a dosage form package, and on the right side, R, heat energy directed across the entire surface of the first layer to form a stabilized granular agglomerate of a thermofused first layer.

Figure 62:
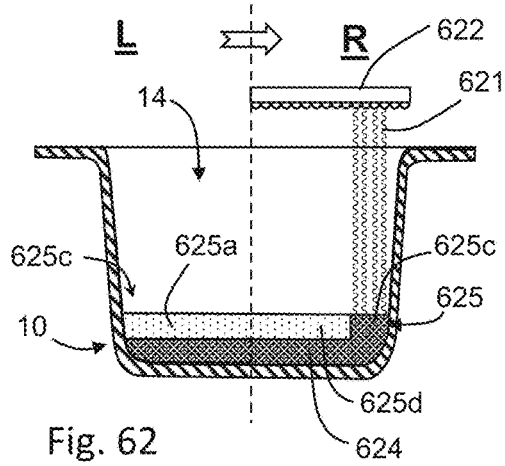

FIG. 62 illustrates on the left side, L, a second layer of the thermofusable powder material onto the thermofused first layer, and on the right side, R, the heat energy targeted at a peripheral portion of the second layer of powder, forming the selected peripheral portion into a stabilized granular agglomerate, while the remaining central portion of the second layer remains unbonded.

Figure 63:
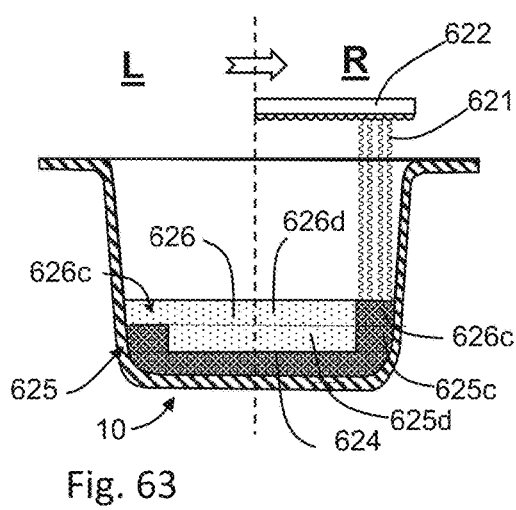

FIG. 63 illustrates on the left side, L, a third layer of the thermofusable powder material onto the thermofused second layer, and on the right side, R, the heat energy targeted at a peripheral portion of the third layer of powder, forming the selected peripheral portion into a stabilized granular agglomerate, while the remaining central portion of the third layer remains unbonded.

Figure 64:
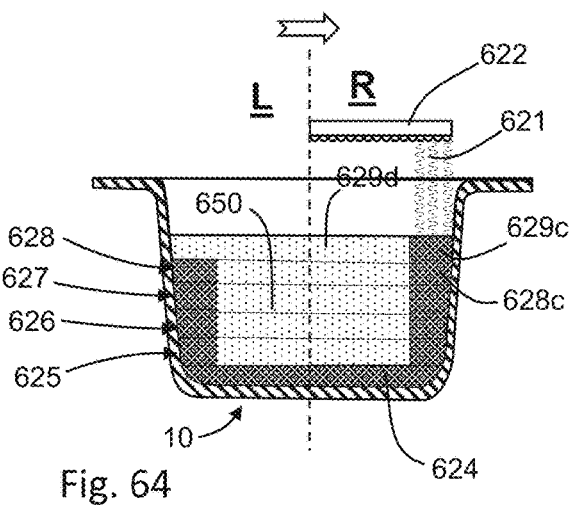

FIG. 64 illustrates a partially thermofused article with five completed layers, with the fourth and fifth layers formed substantially as the third layer, where on the left side, L, a sixth layer of the thermofusable powder material is formed onto the thermofused fifth layer, and on the right side, R, the heat energy targeted at a peripheral portion of the sixth layer of powder, forming the selected peripheral portion into a stabilized granular agglomerate, while the remaining central portion of the six layer remains unbonded.

Figure 45:
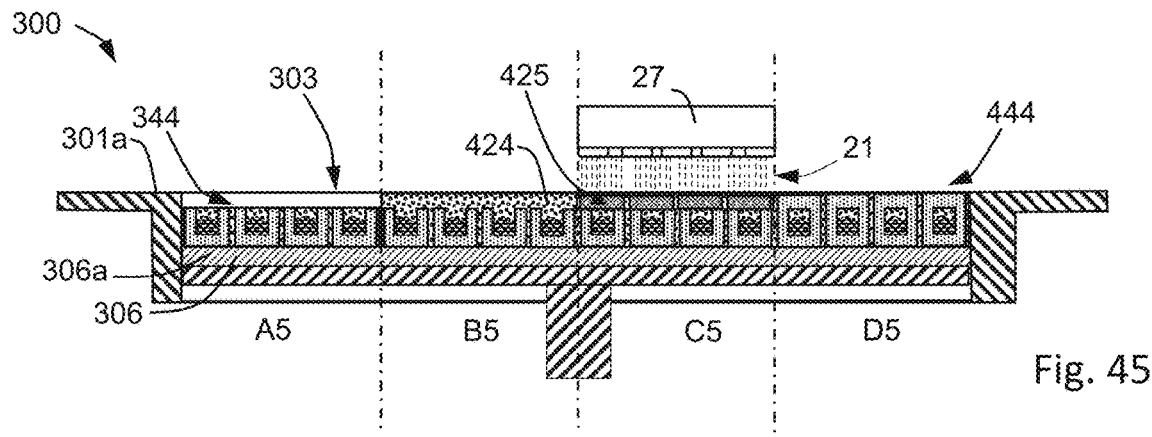
Figure 65:
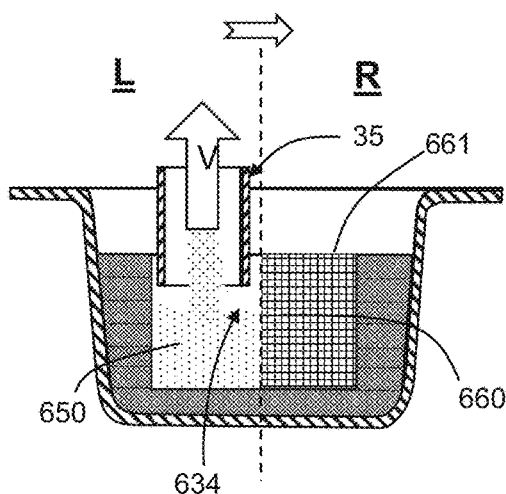

FIG. 65 illustrates on the left side, L, the partially-formed container of FIG. 45, with a vacuum system withdrawing the unbound thermofusable powder out of the central portion, to leave an empty cavity, and on the right side, R, a complete filling of the empty cavity with a particulate medicament.

Figure 66:
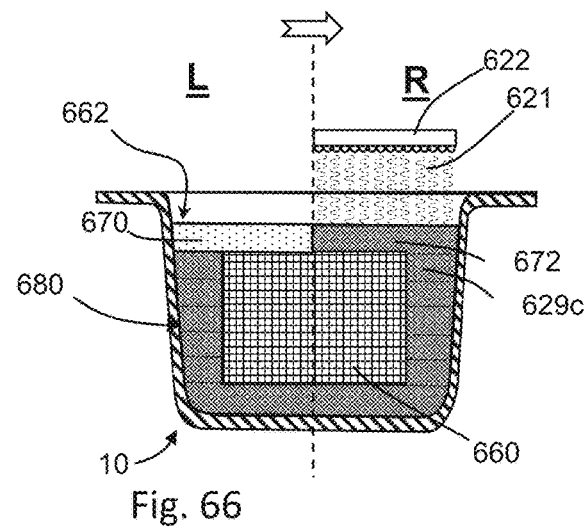

FIG. 66 illustrates on the left side, L, a top layer of a thermofusable powder material onto the upper surface of the peripheral thermofused portion of the sixth layer and the central portion-filling medicament, and on the right side, R, heat energy directed across the entire surface of the first layer to form a stabilized granular agglomerate of a thermofused first layer, enclosing the medicament within the cavity of the stabilized granular agglomerate of the dosage form.

Figure 67:
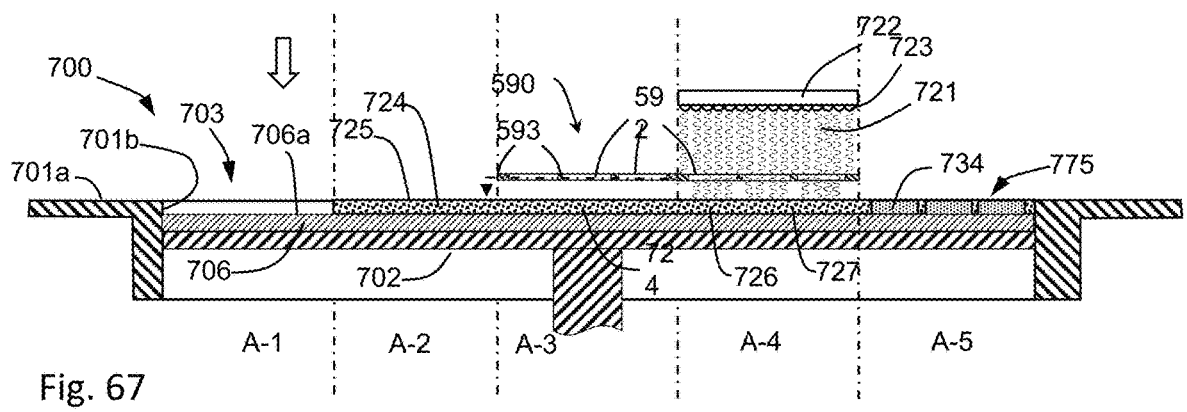
Figure 68:
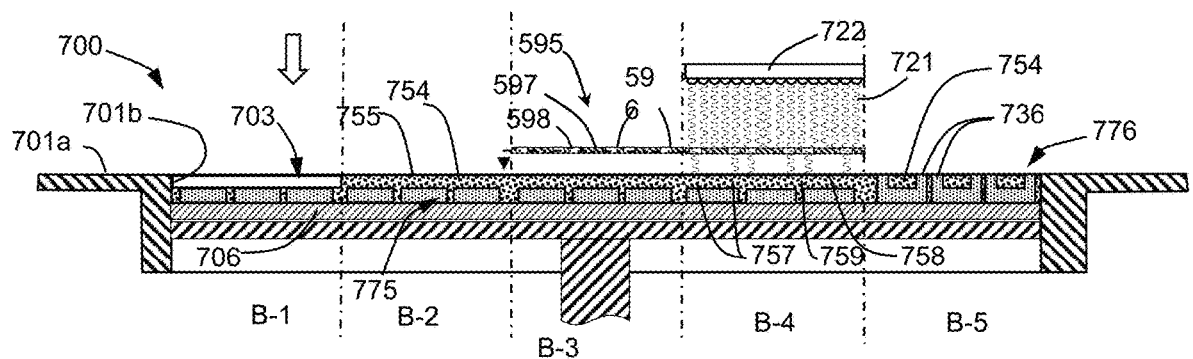

FIGS. 67 and 68 illustrate selected steps in a process for forming of a plurality of container bodies within an open print bed of a 3DP equipment assembly, by placing a layer of thermofusable powder within the upper surface of the open print bed, and directing heat energy across the selected portions of the surface of the layer for increasing the temperature of the thermofusable powder material, and forming thermofused layer portions, and shielding the delivery of the heat energy at or onto areas of the thermofusable powder layer that are to remain unbonded and un-agglomerated.

Figure 69:
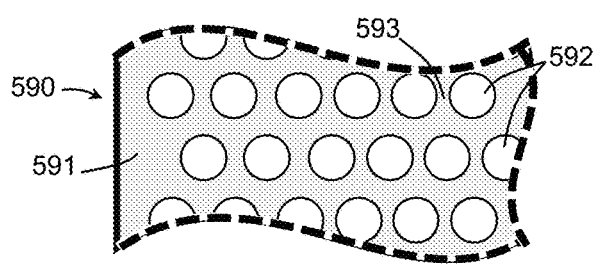

FIG. 69 shows a first embodiment of a shield for allowing heat energy to pass through openings to form uniform circular patterns.

Figure 70:
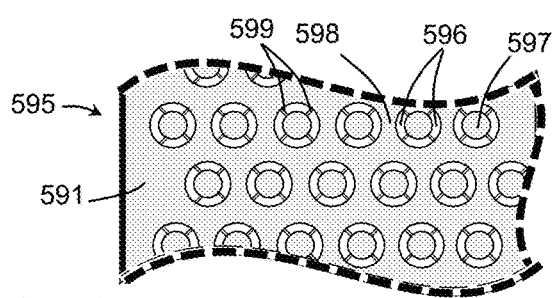

FIG. 70 shows a second embodiment of a shield for allowing heat energy to pass through openings to form annular or ring patterns.

DETAILED DESCRIPTION OF THE INVENTION

Definitions

As used herein, the terms "cavity" and "internal cavity," with respect to a dosage form, interchangeably refer to a compartment or void that is configured for containing and isolating one or more solid materials, particularly one or more medicaments, within any of the dosage forms of the present invention, bound by the container base and an inner surface of the dosage form's peripheral wall. The term "cavity" can also refer to a cavity with an open top surface for receiving solid materials into the cavity, while the term "internal cavity" can refer to the cavity after it has been enclosed to from the rapidly-orodispersible dosage form.

As used herein, the term "unitary", with respect to a dosage form, refers to a dosage form having a single, seamless bound matrix having two or more elements that surround and enclose an interior cavity, for example, a base portion, peripheral walls, and a lid portion, as opposed to a two-piece dosage form having a separated container body and a lid that are secured together.

As used herein, the term "3DP" is an abbreviation referring to either "three-dimensional printing," "three-dimensionally printed," or other such conjugation thereof.

As used herein, the term "tamping" pertains to an act of reducing the porosity or pore volume within a volume of a mass of powder under a force that reduces the volume of the mass of powder. Tamping can be performed with a tamper system, whereby a volume of one or more incrementally-formed layer of powder, particularly within a depression, is shaped and/or reduced.

As used herein, the term "depression," with respect to a packaging, refers to a spatial cavity formed into a portion of a packaging for a dosage form. Non-limiting examples of the depression portion of a packaging include a blister, cup, pod, or other packaging receptacle capable of receiving and containing flowable materials such as powder or liquid.

As used herein, the term "pharmaceutically acceptable" refers to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used herein, the term "derivative" refers to either a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps.

As used herein, the term "orodispersible" refers to dosage forms that can disperse or disintegrate in the mouth in a minimal amount of saliva or water. The term "rapidly-orodispersible" refers to dosage forms take can disperse or disintegrate in the mouth in a minimal amount of saliva or water in 90 seconds or less.

As used herein, the term "shaping," with respect to a 3DP-building process, refers to the act of altering the shape of one or more surfaces of an incremental layer of a material, or the shape of a plurality of one or multiple layers. The altering of the shape can be of the entire surface or of only a portion of the surface, and typically the upper surface at the step of shaping. The altered shape can be flat or planar, convex, concave, or any other shape as desired. The altered shape of the upper surface can be different from the shape of the lower surface.

As used herein, the term, "three-dimensional printing build system" or "3DP build system" generally comprises a powder layering system (region), where a powder material is deposited and/or layered into an incremental powder layer, and then powder material is formed selectively into one or more bound-powder matrix(cies). In one non-limiting example, the bound powder matrix(cies) is formed with a printing system (region), wherein a binding liquid is applied as the printing liquid to the incremental powder layer according to a pre-determined pattern thereby forming a partially- or fully bound-powder layer (an incremental printed layer) comprising the bound powder matrix(cies).

Embodiments of the Invention

Figure 1:
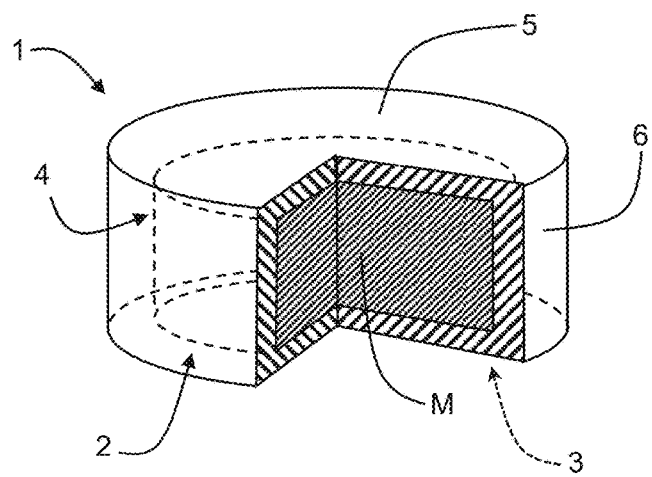
FIG. 1 shows a perspective view of a cylindrical rapidly-orodispersible dosage form of the present invention, with a sectional cut-out that illustrates a medicament contained within an internal cavity of the dosage form.

A non-limiting example of a rapidly-orodispersible dosage form according to the present invention is illustrated in FIG. 1. As shown in FIG. 1, the dosage form 1 has a cylindrical shape and comprises a lower portion 2 having a base 3, an upper portion 4 having a top surface 5, and an annular peripheral wall 6. The dosage form has an interior cavity that is filled with an unbound, solid medicament M and is circumferentially bound by an inner surface of the peripheral wall 6. The lower portion 2, upper portion 4, and the annular peripheral wall 6 comprise a single, interconnected and unitary matrix that encloses and isolates the interior cavity within the dosage form 1.

In various embodiments, the interconnected matrix can consist of adjacent particles of the powder material that are connected and bonded together by a binder material that can bind to the particles of the powder material and to other binder material.

In various embodiments, a dosage form illustrated in FIG. 1 can be formed using an additive manufacturing apparatus, system and process. One non-limiting example of an additive manufacturing process, and associated apparatus and system, is a three-dimensional printing (3DP) building process. Generally, 3DP systems include a powder layering system that forms a layer of build powder, and a printing system that applies a printing liquid, typically containing a binder material, to the layer of build powder according to a pre-determined pattern, thereby binding the build powder and forming a printed or bound-powder layer. A height adjustable platform can be utilized in cooperation with the powder layering system to form incremental printed layers one on top of another to vertically build the dosage form of the invention, thereby forming an article comprising a plurality of incrementally-printed layers. In another embodiment, the number of printed incremental layers can be in a range from at least 3 layers and up to at least 50 layers, or from at least 10 layers up to 50 layers, or from at least 15 layers up to at least 45 layers, or from at least 20 layers up to at least 40 layers, or from at least 5 layers up to at least 15 layers, or from at least 5 layers up to at least 10 layers.

The process of spreading powder and depositing droplets of the printing liquid is repeated until the desired number of layers for the article is complete. The layers adhere to one another due to infiltration of the printing liquid from one layer to an adjacent other layer such that the powder material in one incremental layer can adhere to adjacent, previously-formed incremental layers. Following completion of the initial three-dimensional structure, residual binding liquid can be removed from or reduced in the article by a drying process. The evaporation of solvent during the drying process results in a bound matrix having a three-dimensional architecture comprising the particles of the bound-powder material and a binder material. The physical properties of the resulting dosage forms, such properties including hardness, bulk density, disintegration time, dissolution time, bioavailability, moisture content, mouthfeel and friability, can be generally controlled by selectively varying incremental powder layer thickness, powder composition, printing fluid composition, printing fluid saturation level on a layer, and identity and amount of the excipients included within the dosage form, non-limiting examples of which include the identity and amount of disintegrant, binder, sweetener, surfactant. Additionally, the identity, amount, and physical form of the API compound or medicament can also have an effect, as described in further detail below.

Figure 16:
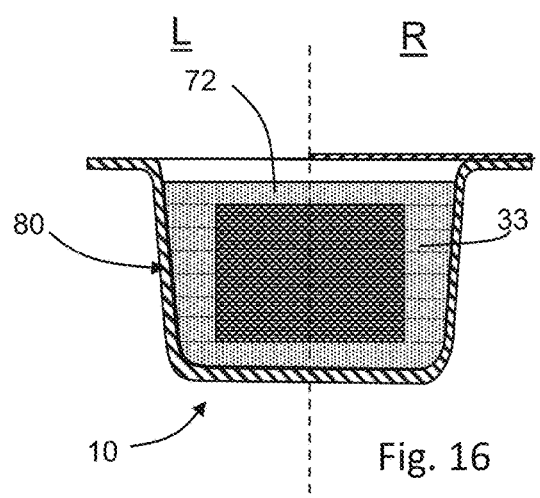
FIG. 16 illustrates on the left side, L, the formation of an upper bound matrix layer enclosing the cavity-filling medicament, to form the rapidly-orodispersible dosage form, and on the right side, R, the application of a lidding film over the dosage-form filled depression to form the dosage form product.

According to various embodiments described herein, an example of another rapidly-orodispersible dosage form according to the present invention is illustrated in FIG. 16, and is described in more details herein after.

Figure 2:
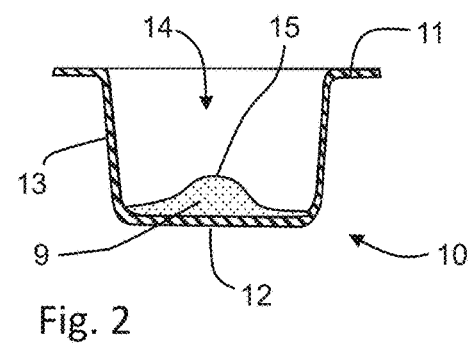
FIG. 2 illustrates depositing a pile of powder material from a powder source into a depression.

With respect to a dosage form, and a rapidly-orodispersible dosage form in particular, in a non-limiting example, FIG. 2 illustrates a step of depositing a first pre-determined amount of a powder material 9 comprising particles, within a blister pack depression 10 formed into a sheet 11 of a film or laminate material. As a non-limiting example, blister pack depressions can be formed using conventional cold-forming or thermoforming processes. The depression 10 has a closed end 12 and an outer wall 13 that forms a boundary for a space 14 within the depression 10. The powder material 9 is discharged from a feed container or hopper, through a powder-dosing apparatus (not shown). Typically, the powder-dosing apparatus is designed and configured to dispense a pre-determined amount of powder material 9 from the feed container, which can include a pre-determined volumetric amount of powder material 9 or a predetermined mass amount of powder material 9. In the illustrated embodiment, a pre-determined amount of powder material 9 is deposited onto the closed end 12 of the depression 10 in the form of a pile 15 of powder material 9. In an embodiment, the predetermined amount of powder material 9 can be a pre-determined volume of a powder material, the powder material 9 having presumably a substantially uniform powder density such that the pre-determined volume delivers a substantially fixed mass weight of the powder material 9. In another embodiment, the pre-determined amount of powder material 9 can be a pre-determined mass weight of a powder material. Again, presuming a substantially uniform powder density, the pre-determined mass weight delivers a substantially fixed volume of the powder material 9. In the illustrated embodiment, the pre-determined mass weight of a powder material 9 provides a volume of powder material 9 sufficient to form a substantially-uniform powder layer of the fixed volume, within the bottom portion of the space 14 within the depression 10. In another embodiment, the pre-determined amount of powder material 9 can be mechanically dosed and/or metered into the depression 10 by any means known in the art, non-limiting examples of which are described in U.S. Pat. Nos. 9,409,699 and 9,828,119, US Patent Publications 2017/0322068 and 2018/0031410, and U.S. Patent Application No. 62/745,750, the disclosures of which are incorporated by reference in their entireties. Another non-limiting example of a mechanical dosing and/or metering apparatus can include a gravimetric powder dispensing/powder dosing apparatus available from ChemSpeed Technologies (https://www.chemspeed.com/flex-powderdose/), the disclosure of which is incorporated by reference in its entirety.

Figure 3:
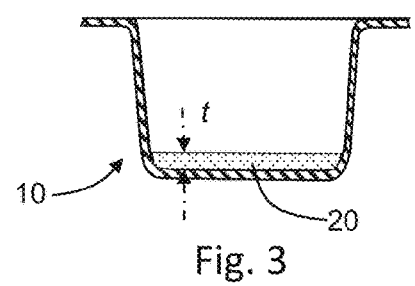
FIG. 3 illustrates the formation of a first layer of powder material having a substantially-uniform thickness.

Upon dispersing a pre-determined amount of a powder material 9 into the depression 10, the powder material 9 can be formed into a base powder layer having a substantially uniform thickness, as shown in FIG. 3, by any leveling means known in the art. Non-limiting examples of such leveling means include: tamping; oscillation laterally, orbitally, and/or vertically; vibration; brushing; and vacuuming. In particular, U.S. Pat. No. 10,071,372 and U.S. Patent Publication 2017/0312179, the disclosures of which are incorporated herein by reference in their entireties, describe a system that both dispenses a predetermined amount of the powder material 9 and subsequently forms the powder material 9 into a substantially uniform layer. In an embodiment, the leveling means can be a tamping system, a non-limiting example of which is described in U.S. Patent Application No. 62/745,750, above. The tamping system can use a tamper with an undersurface that contacts with a pile 15 of powder material 9 to form a uniform powder layer having a substantially uniform thickness, t, as shown in FIG. 3. The tamper can be used to form an incremental layer with a substantially uniform thickness and/or to compress the plurality of layers of the printed dosage form, as described in further detail below.

In another embodiment, the substantial uniform thickness of the base powder layer 20, or any of the successive incremental powder layers discussed in further detail below, can have a predetermined height in a range from at least 0.005 inches, up to 0.1 inches; or at least 0.01 inches, up to 0.08 inches; or at least 0.02 inches, up to 0.06 inches; or at least 0.03 inches, up to 0.05 inches; or at least 0.025 inches, up to about 0.05 inches. In another embodiment, the substantial uniform thickness of any of the powder layers can be in a range from at least 0.1 mm, up to 2.5 mm; or at least 0.5 mm, up to 2.0 mm; or at least 0.5 mm, up to 1.5 mm; or at least 1 mm, up to 1.5 mm; or at least 0.75 mm, up to 1.25 mm. In another embodiment, the substantial uniform thickness of any of the powder layers can be in a range from at least about 100 microns to about 500 microns, or from at least about 100 microns to about 400 microns, or from at least about 100 microns to about 300 microns.

Without being limited by a particular theory, as thicker incremental layers are used, an increasing amount of binding liquid can be deposited to ensure adequate binding both within the plane or thickness of the layer, and from layer-to-layer, and specifically from the powder layer being bound and the previously-formed bound-powder layer below. Conversely, for a thinner incremental layer a lesser amount of binding liquid can be deposited to obtain the same extent of binding. For a given amount of binding liquid deposited per layer, using a larger layer thickness can reduce (worsen) handleability of the dosage form, but reduce (improve) dispersion time. If a layer is too thick relative to a given amount of liquid, laminar defects may form and cause the dosage form to fracture along the planar interface of the layers (delamination), or the dosage form itself may not have adequate strength to be handled at all.

In another embodiment, the base powder layer 20, or any of the successive incremental powder layers discussed in further detail below, can have a pre-determined mass of deposited powder material, based in part on the desired thickness of the bound-powder layer. In another embodiment, the amount of the dispensed powder material to form the bound-powder layer can be in a range from at least 1 mg and up to 1 g; or at least 10 mg and up to 500 mg; or at least 25 mg and up to 300 mg; or at least 50 mg and up to 250 mg; or at least 100 mg and up to 200 mg; or at least 125 mg and up to 175 mg.

Figure 4:
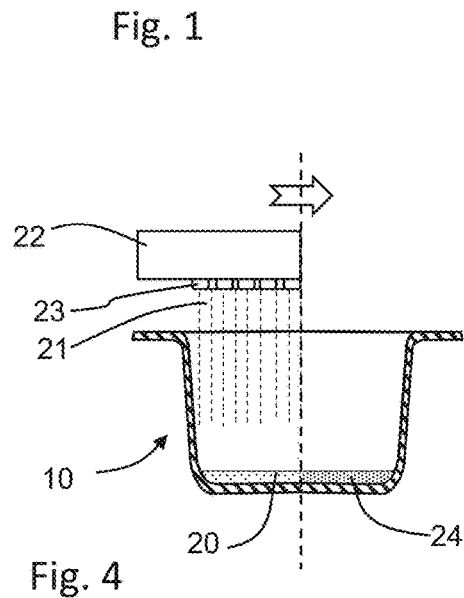
FIG. 4 illustrates the application of a printing liquid onto the substantially-uniform first layer of powder material, to form a wetted powder layer.

FIG. 4 shows, in the left side of the illustration, a step of applying a binding liquid onto a substantially uniform base powder layer 20. In various embodiments, the binding liquid contains (comprises) a binder material, or the build powder contains (comprises) a particulate binder material, or both the binding liquid and the build powder contain (comprise) a binder material. The binding liquid can be applied as a printing liquid using 3DP methods and systems, such as those described in U.S. Pat. Nos. 6,471,992, 6,945,638, 7,300,668, 7,875,290, 8,088,415, and 8,888,480, the disclosures of which are incorporated by reference in their entireties. Printing liquid can be dispensed in drops or in fluid units resembling drops. Either the printhead, the substrate, or both, may move to facilitate deposition of droplets. Drops can be dispensed in a succession that forms a line corresponding to the relative motion or movement of the printhead nozzle and the substrate. The spacing between those drops is the drop-to-drop spacing, which is a function of the droplet dispensing rate from the nozzle and the relative rate of movement of the nozzle and the substrate. After completion of one line, another line may be deposited adjacent to the earlier-deposited line and separated from the earlier-deposited line by a distance that is a line-to-line spacing. In various embodiments, drops may be dispensed from a plurality of spaced-apart printing nozzles, arranged into one or more rows, and in a succession that forms a row line of drops corresponding to the motion of the printhead, wherein the nozzle-to-nozzle spacing results in a line of drops having a drop-to-drop spacing. Drops can be dispensed in a succession from each of the nozzles that forms a column line of drops corresponding to a motion or movement of the printhead nozzle transverse to the row of nozzles of the printhead. The spacing between those drops is a line-to-line spacing, which is a function of the droplet dispensing rate from the nozzle and the rate of transverse movement of the printhead.

In FIG. 4, a first predetermined quantity of printing liquid is deposited by dispensing droplets 21 of the binding liquid from the print nozzles 23 of an inkjet printing nozzle assembly 22. The binding liquid can be dispensed across an entire surface of the substantially uniform base powder layer 20. In embodiments in which the printing liquid is a binding liquid comprising a binding material, the droplets 21 of binding liquid bind particles of the substantially uniform base powder layer 20 into a cohesive powder-liquid matrix, forming a substantially-uniform first layer of wetted powder 24, shown in the right side of the illustration of FIG. 4. In a typical embodiment, the binding liquid includes an amount of a solvent that remains in excess in the resulting wetted powder layer, and is preferably removed to form a finished bound-powder layer. In another embodiment, excess solvent can be evaporated off of the bound-powder layer by heating or irradiating the layer with infrared radiation, for example as described in U.S. Pat. Nos. 6,990,748, 6,047,484, and 4,631,837, the disclosures of which are incorporated herein by reference in their entireties.

In another embodiment, the build powder material can be a bulk powder comprising a plurality of particulate components. In another embodiment, one or more of the plurality of particulate components can include one or more pharmaceutically acceptable excipients, selected from the group consisting of: disintegrants, particulate binder materials, surfactants, glidants, sweeteners, flavorants, humectants, antioxidants, preservatives, and diluents, including combinations thereof. In another embodiment, the one or more pharmaceutically acceptable excipients can also be dissolved, suspended, or otherwise comprised within the binding liquid. Each excipient may be independently selected from the group consisting of a water-soluble, aqueous-fluid soluble, partially-water soluble, partially-aqueous-fluid soluble, water-insoluble or aqueous-fluid insoluble excipient, as needed, to provide the desired particle-to-particle binding properties within the printed matrix. Most pharmaceutically acceptable excipients, both small molecules and polymers, can be employed to support the activity or stability of the medicaments and/or to facilitate the rapid dispersion of the dosage form in the presence of an appropriate aqueous fluid, for example, water or saliva. Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

In another embodiment, one or more disintegrants can be comprised within the bulk powder. The use and identity of a particular disintegrant can be independently selected upon each occurrence, dependent on desired dispersion properties of the dosage form. In another embodiment, the bulk powder can comprise disintegrant in a weight range, by weight of the bulk powder, of at least 5% and up to 30%; or at least 10% and up to 25%; or at least 15% and up to 25%; or at least 18% and up to 24%; or at least 18% and up to 23.7%; or at least 1% and up to 30%; or at least 1% and up to 25%; or at least 20% and up to 25%. In another embodiment, a disintegrant can be selected from the group consisting of: microcrystalline cellulose, crospovidone (cross-linked polyvinylpyrrolidone), croscarmellose, or sodium starch glycolate, including combinations thereof. In another embodiment, the disintegrant can be microcrystalline cellulose, including one or more grades of AVICEL® microcrystalline cellulose, available from Sigma-Aldrich.

In an embodiment, one or more binder materials can be comprised within the bulk powder or within the binding liquid. The binder material can be independently selected upon each occurrence. Adhesion of the particles to and/or by the binder material occurs either when the binder material is contacted by the binding liquid from the printhead or when it is present in the binding liquid itself as a binding liquid. The binder material is preferably water soluble, aqueous fluid soluble, partially water soluble or partially aqueous fluid soluble. The binding liquid can comprise binder material in a weight range, by weight of the binding liquid, of at least 1% and up to 20%; or at least 5% and up to 15%; or at least 8% and up to 12%. In some embodiments, the bulk powder comprises up to 15%, for example, up to 10% by weight, of a binder material. In another embodiment, the bulk powder comprises binder material in a weight range, by weight of the bulk powder, of at least 5% and up to 15%; or at least 8% and up to 14%; or at least 9% and up to 11%. In another embodiment, the printed dosage form can comprise binder material in a weight range, by weight of the dosage form, of at least 1% and up to 20%; or at least 5% and up to 14%; or at least 8% and up to 12%. The binder material is present in the binding liquid only, in the bulk powder only, or in both the binding liquid and the bulk powder.

In an embodiment, binder materials can be selected from the group consisting of: water-soluble synthetic polymer, polyvinylpyrrolidone (povidone), sorbitol, mannitiol, xylitol, lactitol, erythritol, pregelatinized starch, modified starch, hydroxypropylmethylcellulose and others. The preferred binder is polyvinylpyrrolidone, e.g., PVP K30, modified starch (e.g., starch sodium octenylsuccinate), mannitol or a combination thereof. PVP with a K value different from 30 may be used, including without limitation PVP K25 and PVP K90. Spray dried lactose, fructose, sucrose, dextrose, sorbitol, mannitol, or xylitol can also be utilized as binder materials, although they generally exhibit low-strength binding properties in many applications.

Without being limited by a particular theory, the presence, identity, and concentration of binding materials and disintegrants can influence the hardness, friability, and dispersion time of the dosage form. Generally, the greater the amount of a binder material that is present in the dosage form, the higher the hardness, the lower the friability and the slower the dispersion time. On the other hand, increasing the amount of disintegrant generally provides lower hardness, increased friability and a faster dispersion time. Accordingly, in another embodiment, the rapidly orodispersive dosage form of the invention comprises a balanced amount of binder and disintegrant, depending on the desired hardness, friability and dispersion time of the dosage form.

In some embodiments, which may be used in combination with any one or more of the embodiments described above and herein, one or more sweeteners can be comprised within the bulk powder or within the binding liquid. Taste-masking of the solid medicament or other excipients can be achieved when at least one sweetener is present in at least the binding liquid, and preferably, both the binding liquid and the bulk powder. The presence and identity of a sweetener can be independently selected upon each occurrence. In another embodiment, the binding liquid and the bulk powder can have at least one sweetener in common, such as, in a non-limiting example, when the binding liquid and bulk powder each comprise the same sweetener and the bulk powder comprises an additional sweetener. In another embodiment, the bulk powder comprises up to 5% by weight of sweetener, or up to 2% by weight of sweetener, or up to 1.5% by weight of sweetener. In another embodiments, the binding liquid comprises up to 5% sweetener, or comprises sweetener in a range from at least 0.5% be weight, up to 4% by weight; or at least 1% by weight, up to 3% by weight of the binding liquid.

In an embodiment, sweeteners can be selected from the group consisting of a glycyrrhizinic acid derivative, such as, in a non-limiting example, Magnasweet® (monoammonium glycyrrhizinate), sodium saccharin, sucrose, stevia, sucralose, aspartame, acesulfame potassium, and neotame, including combinations thereof. In another embodiment, sucralose can be included within the binding liquid. In another embodiment, a sweetener is included within the binding liquid. In another embodiment, a sweetener is included within both the binding liquid and the bulk powder. In another embodiment, a sweetener may be selected from the group consisting of acesulfame potassium, alitame, ammonium glycyrrhizate, aspartame, compressible sugar, confectioner's sugar, corn syrup solids, dextrose, dextrose anhydrous, erythritol, fructose, galactose, glycerin, glycine, glycyrrhizin, inulin, isomalt, lactitol, liquid glucose, maltitol, maltitol solution, maltose, mannitol, D-mannose, neohesperidin dihydrochalcone, neotame, saccharin, saccharin sodium, sodium cyclamate, sorbitol, sucralose, sucrose, tagatose, thaumatin, trehalose, and xylitol.

In an embodiment, one or more flavorants can be comprised within the bulk powder or within the binding liquid. The presence and identity of a flavorant can be independently selected upon each occurrence. In another embodiment, the flavorant is water soluble, aqueous-fluid soluble, partially-water soluble, or partially-aqueous-fluid soluble. The binding liquid comprises can comprise a flavorant in a range of at least 0.01% by weight, and up to 5% by weight; or at least 0.1% by weight, and up to 1% by weight; or at least 0.2% by weight, and up to 0.5% by weight of the binding liquid. The flavorant may be provided on a powdered carrier. The carrier can be chosen from the group consisting of: starches, celluloses, and other excipients within which the flavorant could be absorbed, adsorbed, encapsulated, or otherwise loaded, including combinations thereof. In another embodiment, the bulk powder can comprise a flavorant-loaded carrier in a range from at least 0.1% by weight, and up to 10% by weight; or at least 1% by weight, and up to 9% by weight; or at least 2% by weight, and up to 8% by weight of the bulk powder. The dosage form can comprise a flavorant-loaded carrier in a range from at least 0.1% by weight, and up to 10% by weight; or at least 1% by weight, and up to 9% by weight; or at least 2% by weight, and up to 8% by weight of the dosage form. A flavorant can be included within the binding liquid only, within the bulk powder only, or within both the binding liquid and the bulk powder.

In another embodiment, the one or more flavorants can be selected from the group consisting of spearmint, peppermint, mint, vanilla, orange, lemon, citrus, lime, grape, cherry, strawberry, chocolate, and coffee, including combinations thereof.

In another embodiment, one or more surfactants can be comprised within the bulk powder or within the binding liquid. The presence and identity of a surfactant can be independently selected upon each occurrence. The binding liquid or bulk powder can comprise one or more surfactants in a range from at least 0.1% by weight, and up to 4% by weight; or at least 1% by weight, and up to 3% by weight; or at least 1.5% by weight, and up to 2.5% by weight.

In an embodiment, the one or more surfactants can be selected from the group consisting of polysorbate (PEGylated sorbitan (a derivative of sorbitol) esterified with fatty acid) and a poloxamer, including combinations thereof. A polysorbate can be selected from the group consisting of: polysorbate 20 (Polyoxyethylene (20) sorbitan monolaurate), polysorbate 40 (Polyoxyethylene (20) sorbitan monopalmitate), polysorbate 60 (Polyoxyethylene (20) sorbitan monostearate), polysorbate 80 (Polyoxyethylene (20) sorbitan monooleate), sodium lauryl sulfate, poloxamer (comprising a central (poly(propylene oxide)) flanked by two chains of (poly(ethylene oxide), e.g. LUTROL®), and low molecular weight polyethylene glycol (e.g. PEG 400), including combinations thereof. A poloxamer may be selected from the group consisting of poloxamers 124, 188, 237, 338, or 407, including combinations thereof.

In another embodiment, one or more preservatives can optionally be comprised within the bulk powder or within the binding liquid. The presence and identity of a preservative can be independently selected upon each occurrence. Non-limiting examples of suitable preservatives include antifungal or antimicrobial preservatives such as methylparaben and propylparaben. In another embodiment, the binding liquid can comprise at least 0.001% by weight, and up to 0.2% by weight, of one or more preservatives.

In another embodiment, one or more glidants can optionally be comprised within the bulk powder. The presence and identity of a glidant can be independently selected upon each occurrence. The bulk powder can comprise a glidant in a range from at least 0.1% by weight, and up to 2.0% by weight; or at least 0.25% by weight, and up to 1.5% by weight; or at least 0.5% by weight, and up to 1.0% by weight of the bulk powder. The glidant can comprise fumed silica (colloidal silicon dioxide).

In another embodiment, two or more excipients can be comprised within the bulk powder material as a co-granulate, a non-limiting example of which is Ludipress® (BASF Pharma), which comprises 93% (w/w) lactose, 3.5% (w/w) povidone, and 3.5% (w/w) crospovidone.

In a non-limiting example, the bulk powder material can consist of dextrose. In another non-limiting example, the bulk powder material can consist of up to 75% (w/w) ascorbic acid, with the balance dextrose.

In various embodiments, the bulk powder material and/or the binding liquid can comprise a medicament compound, including, for example, any one or more of the medicaments listed below. A medicament included within the bulk powder material and/or the binding liquid can be either identical to or different from any medicament that is comprised within a payload deposited into the cavity of any of the rapidly-orodispersible tablets described herein. In a non-limiting example, a bulk powder material can comprise metformin hydrochloride, microcrystalline cellulose, povidone, silica, corn starch, and optionally one or more sweeteners, particularly a sweetener selected from the group consisting of sucralose and monoammonium glycyrrhizinate, including combinations thereof.

In another embodiment, the bulk powder and/or the binding liquid can comprise glycerin (glycerol), which can exhibit characteristics of a humectant, sweetener, preservative, lubricant, saponifier, or a solvent. The use of glycerin in 3DP dosage forms is described in U.S. Pat. Nos. 9,314,429, 9,339,489, 9,492,380, 9,669,009, and 10,028,909, the disclosures of which are incorporated by reference in their entireties.

In another embodiment, glycerin can be comprised within the binding liquid. In another embodiment, the binding liquid comprises glycerin, water, and at least one organic solvent. In another embodiment, the binding liquid can comprise glycerin in a range from at least 1% by weight, and up to 10% by weight; or at least 2% by weight, and up to 8% by weight; or at least 3% by weight, and up to 5% by weight of the binding liquid. In another embodiment, the dosage form can comprise glycerin in a range from at least 0.05% by weight, and up to 5% by weight; or at least 0.25% by weight, and up to 2.0% by weight; or at least 0.5% by weight, and up to 1.5% by weight; or at least 0.5% by weight, and up to 1.0% by weight, of the dosage form.

In another embodiment, the binding liquid can comprise one or more organic solvents in a range from at least 1% by weight, and up to 25% by weight; or at least 5% by weight, and up to 20% by weight; or at least 10% by weight, and up to 15% by weight of the binding liquid. The one or more organic solvents is an alcohol selected from the group consisting of ethanol, methanol, propanol, and isopropanol, including combinations thereof.

Figure 5:
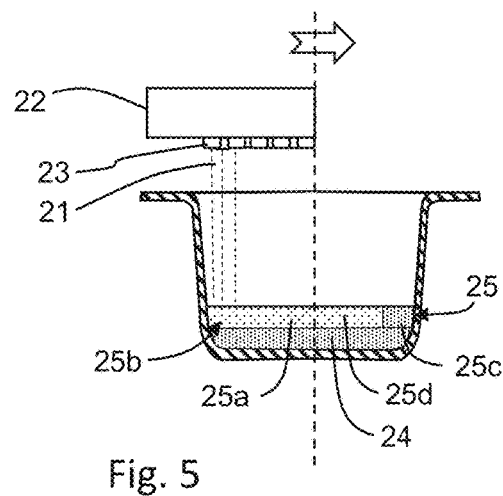
FIG. 5 illustrates the application of a printing liquid at peripheral portions of a second substantially-uniform layer of powder material, to form a second incremental layer having a wetted peripheral portion and a central, unwetted portion.
Figure 6:
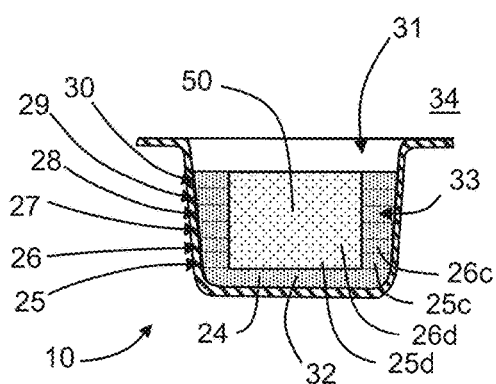
FIG. 6 illustrates an example of a container formed within a depression, the container having a base, a peripheral wall, and a central cavity filled with unwetted, unbound powder.

To facilitate forming an interior cavity, the print head and nozzles of the 3D printing assembly can be configured or programmed to apply droplets of binding liquid upon any specific portion of a substantially uniform layer of powder, particularly a peripheral portion of the layer. FIGS. 5 and 6 show a non-limiting example of the deposition of additional predetermined amounts of powder that are deposited as or formed into intermediate incremental layers, with each layer having its own substantially uniform thickness. In FIG. 5, in the left side of the illustration, the binding liquid is applied only at the peripheral portions 25b of a second substantially-uniform layer of powder material 25a, to form a second incremental layer 25 having a peripheral portion of wetted powder 25c and leaving a central portion of unwetted, unbound powder 25d shown in the right side of the illustration. Subsequently, a third powder layer can be applied into a substantially-uniform third powder layer upon the second incremental layer, and droplets of binding liquid applied only at the peripheral portions of the powder material, to form a third incremental layer 26 having a peripherally-bound portion 26c and a central portion of unwetted, unbound powder 26d as shown in FIG. 6. Repeating the process to form fourth, fifth, sixth, and seventh incremental layers (27, 28, 29, and 30, respectively) results in a container 31 for a dosage form having a base 32, a peripheral wall 33, and a central cavity filled 34 with unwetted, unbound build powder material 50, as shown in FIG. 6.

Those skilled in the art would appreciate that a container formed by a process as described above can comprise any number of consecutive intermediate-peripherally-bound layers to form the peripheral wall, and such examples are omitted for clarity. Additionally, the dosage form can comprise any number of base powder layers, in which the entire layer comprises a bound powder matrix, prior to forming the peripherally-bound layers that form the boundary of the internal cavity, and that such examples are also omitted for clarity. The completed dosage form can also comprise any number of powder layers comprising an upper portion or lid of the dosage, in which the entire layer comprises a bound powder matrix. In one non-limiting example, "end" portions of the dosage form, comprising either the base and/or upper portions of the dosage form, can comprise 1 to 10, 1 to 7, 2 to 7, 2 to 5, or 4 to 6 printed incremental layers. In another non-limiting example, intermediate portions of the dosage form that comprise the peripheral wall of the dosage form can comprise 2 to 10, 2 to 7, 2 to 5, or 4 to 7 printed incremental layers. In a further embodiment, a portion of one or both of the "end" portions, or the peripheral wall, can have an indicium, source, or design printed into the surface of the incremental layer(s).

Figure 7:
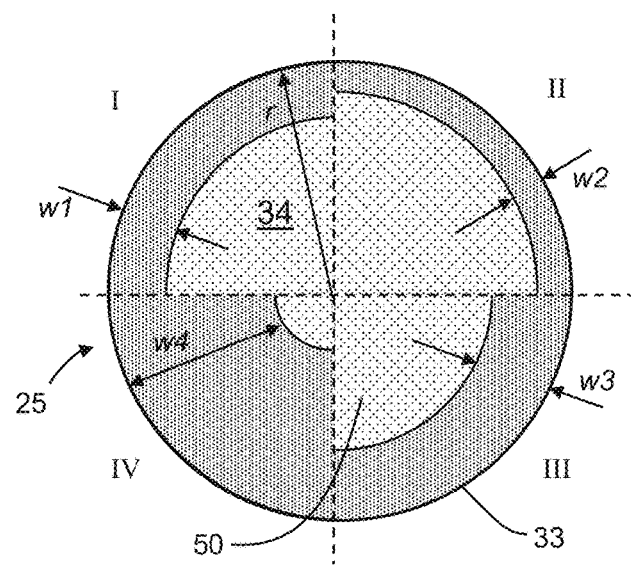
FIG. 7 shows a top plan view of exemplary substantially-uniform widths of the peripherally-bound portion of an incremental layer forming the peripheral wall of the container.

In another embodiment, the peripherally-bound portion of incremental layers that define the container peripheral wall can have a substantially-uniform thickness. FIG. 7 shows an exemplary top view of the second incremental layer 25 of container 31, in a first quadrant (I) of the illustration, in which the peripheral wall 33 has a substantially uniform width, w1, encircling the central filled cavity 34. For cylindrical containers, including rapidly-orodispersible containers, each of the incremental layers that define the peripheral wall 33 can have the same substantially-uniform width, w. In another embodiment, the substantially-uniform width can be modified to affect such factors including, but not limited to: the desired hardness and friability of the dosage form, the desired or required volume of the interior cavity, and/or the desired orodispersibility of the dosage form in a small volume of water. In another embodiment, the peripherally-bound portion can have a substantially uniform width in a range from at least 0.5 mm, and up to 10 mm; or from at least 1.0 mm, and up to 5.0 mm; or from at least 1.5 mm, and up to 3 mm. In another embodiment, the ratio of the substantially-uniform width, w, of the peripherally-bound portion, relative to the radius, r, of the entire layer can be at least 1:10, or at least 1:9, or at least 1:8, or at least 1:7, or at least 1:6, or at least 1:5, and up to 1:4, up to 1:6 or up to 1:8. Non-limiting examples of several peripherally-bound incremental layers having different substantially-uniform width or thicknesses, relative to the radius of the container, are illustrated as wall width w2 in the second quadrant (II), as wall width w3 in the third quadrant (III), and as wall width w4 in the fourth quadrant (IV) of the illustration of FIG. 7, wherein a ratio of the width or thickness w of the peripheral wall to the radius or effective radius r of the container is from about 4:1 to about 1:8, and in some embodiments, from about 1:3 to about 1:6, or about 1:4 to about 1:5.

Figure 8:
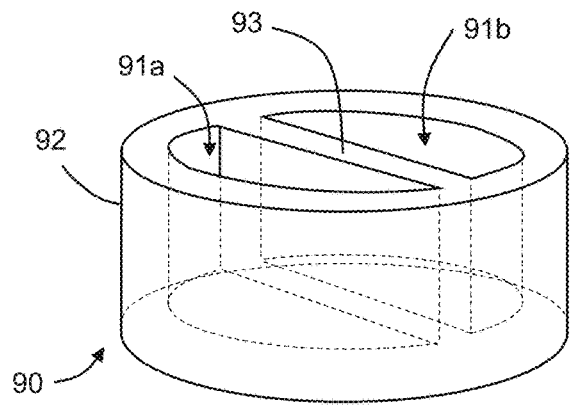
FIG. 8 shows a perspective view of a container having two cavities.
Figure 9:
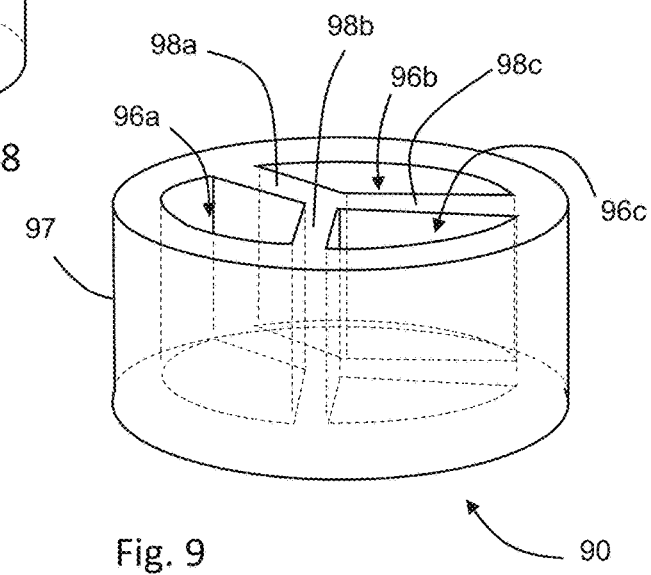
FIG. 9 shows a perspective view of a container having three cavities.

In various embodiments, and illustrated with respect to a dosage form similar in shape to that of dosage form 1 of FIG. 1, two non-limiting arrangements of two or more cavities within a container body are illustrated in FIGS. 8 and 9. FIG. 8 depicts an arrangement of cavities 91a and 91b within a container 90, wherein each cavity is bounded by a peripheral wall 92 and a bisecting interior wall 93. FIG. 9 depicts an arrangement of cavities 96a, 96b, and 96c within a container 95, in which each cavity is bounded by a peripheral wall 97 and two interior walls 98a and 98b, 98a and 98c, or 98b and 98c, respectively. In embodiments of the invention, the printing liquid can be applied onto the powder layer within the printing area in a peripheral pattern that forms the peripheral wall of the container body, and in one or more continuous lines extending into the interior area from the peripheral pattern that form the interior walls of the container body, to divide the interior area of the dosage form into the two or more cavities that are arranged and separated angularly (in pie-shaped segments are illustrated in FIGS. 8 and 9, radially (in concentric rings), or axially (in layers through the depth of the dosage form). Those skilled in the art would appreciate that there are countless print patterns that could be utilized to deposit a printing liquid in the center portion of the print area, in order to form any number of cavities defined by interior walls.

Accordingly, a rapidly-orodispersible container can generally formed by a method comprising the following steps: forming a rapidly-orodispersible container base and forming a rapidly-orodispersible peripheral wall. In another embodiment, the method for forming the container base can comprise the steps of: a) dispersing a powder material into a base powder layer; b) dispensing a printing liquid comprising a binder material onto the base powder layer to form a bound base-matrix layer; and c) optionally repeating steps a) and b) one or more times, and the method for forming the peripheral wall can comprise the steps of: d) dispersing the powder material into an intermediate powder layer atop the container base; e) dispensing the printing liquid onto a peripheral portion of the intermediate powder layer, without dispersing the printing liquid onto an interior portion of the intermediate powder layer, to form: a filled container consisting of a bound wall-matrix layer that is bound to the container base, and an interior portion consisting of unbound powder material; and f) optionally repeating steps d) and e) one or more times.

Figure 10:
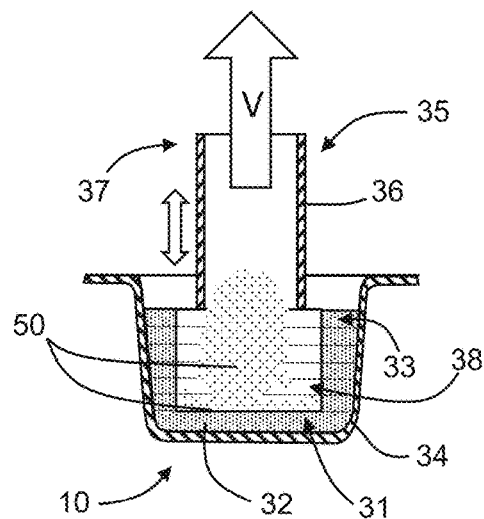
FIG. 10 illustrates the application of a vacuum by a vacuum apparatus positioned within a cavity and evacuating unwetted/unbound powder from the container.

In another embodiment, unbound powder material can be emptied from the filled cavity using a powder evacuation apparatus and system. In some embodiments, the powder evacuation system can comprise a vacuum system configured to fluidize and remove the powder material without damaging or disturbing the bound matrices that comprise the container base and peripheral wall. In a first non-limiting example, a vacuum system can include a vacuuming apparatus for removing unbound powder from a single cavity is shown in FIG. 10. The vacuuming apparatus 35 can be in position to fluidize and remove unbound build powder material 50 from the cavity 34 of a rapidly-orodispersible container 31 within depression 10. The vacuuming apparatus 35 comprises a suction cylindrical body 36 having an outlet, suction end 37, and an inlet, powder end 38. The vacuuming apparatus 35 is positioned within the depression 10 and in substantially axial registry with the cavity 34 of the rapidly-orodispersible container 31. A suction is applied to the interior of the cylindrical body 36 by a remote vacuum source, as indicated by the arrow with the letter, "V". The vacuum source can be regulated by any known device in the art that can provide a controllable amount of vacuum. The vacuum in the cylindrical body 36 results in an intake of air through the inlet end 38, causing particles of the build powder material 50 to be drawn out from the cavity 34 and into the inlet end 38 of the vacuuming apparatus 36. The cylindrical body 36 and inlet end 38 can be configured to be inserted into the partially-filled cavity 34, as shown in FIG. 10, to ensure complete removal of the unbound build powder material 50. As the inlet end 38 is lowered toward the container base 32, the application of vacuum can be carefully controlled and decreased to reduce the risk that the incoming air flow will damage or disturb the matrix of powder and binder of the container base 32 and peripheral walls 33. Eventually, the entire volume of the unbound build powder material 50 is drawn from the cavity and out of the outlet end 37 of the cylindrical body 36. In another embodiment, the unbound powder drawn up by the vacuuming system can be deposited into a powder reservoir and stored for future use.

Figure 11:
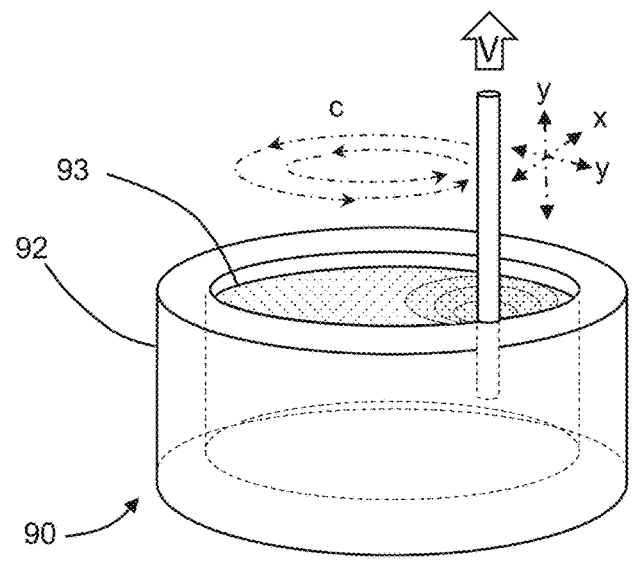
FIG. 11 illustrates a vacuum pipette that can be lowered into the unbound powder of a container, and maneuvered circumferentially and radially within the cavity to evacuate the unbound powder.

In an alternative embodiment of a powder evacuation apparatus and system, a smaller-diameter vacuum pipette, relative to the diameter or width of the cavity, can be used to vacuum the unbound powder material from within the cavity of the built container body. As shown in FIG. 11, an inlet tip of a smaller-diameter vacuum pipette, can be placed above the surface of the unbound powder material. With a vacuum applied to the outlet end of the pipette, the inlet tip can be lowered (in the vertical or y direction) into the unbound powder and maneuvered circumferentially (c direction) and radially or laterally (x,y direction) within the cavity to draw powder into the inlet tip and evacuate the unbound powder from the cavity.

In another embodiment, a powder evacuation apparatus can comprise a plurality of the vacuum pipettes, arranged in a matrix and configured or adapted to be moved in unison as a group, or individually, into and within a corresponding matrix of spaced-apart container bodies to evacuate their respective unbound powder.

In another embodiment of a powder evacuation apparatus and system, unbound powder material can be fluidized and removed from the cavities of a plurality of rapidly-orodispersible containers within the same build platform, particularly a plurality of containers within the same packaging, such as a blister pack. The unbound powder can be fluidized by directing a turbulent, i.e., multi-directional, air or gas glow immediately above the filled cavity. In a further embodiment, a shielding or masking plate can be placed over the plurality of containers, the plate having perforations that expose the unbound powder within the filled cavities, but also sequester the containers themselves, as the turbulent air or gas flow is passed over the cavities.

Figure 12:
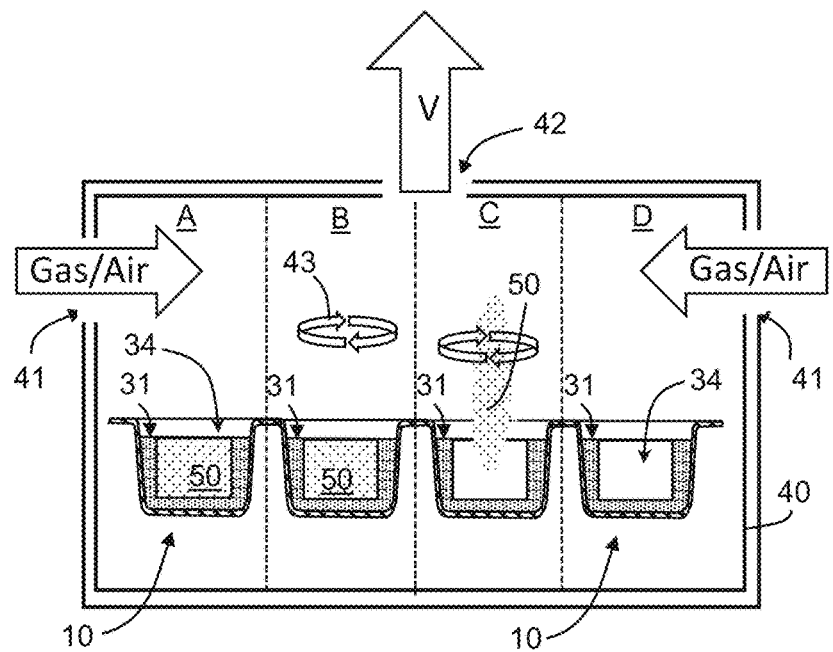
FIG. 12 illustrates the operation of a vacuuming system within a ventilated hood, illustrating the generation of a turbulent airflow over the container having a central portion of unwetted/unbound powder.

In a non-limiting example and as illustrated in FIG. 12, a vacuuming system can comprise a ventilated hood 40 disposed above a plurality of rapidly-orodispersible containers 31 filled with unbound build powder 50 and disposed within a plurality of depressions 10. In some embodiments, the plurality of depressions 10 can be disposed within a blister pack, or a plurality of blister packs. Within the ventilated hood 40, ambient air or gas can be drawn in through a plurality of air inlets 41 to create a turbulent air flow 43 above the containers, fluidizing and emptying the unbound build powder material 50 from each of the cavities 34. The turbulent air and fluidized powder can both be evacuated from the hood by a suction applied to the interior of the body by a remote vacuum source at an outlet portion 42 of the hood 40. In another embodiment, the outlet portion can contain a screen, mesh, or filter for collecting and/or redirecting the unbound powder material into a powder reservoir for future use, as described above, while allowing the air or gas to pass through the outlet freely.

FIG. 12 illustrates the effect of the turbulent air flow 43 above one of the cavities 34, illustrated in four illustrated segments. The first segment A illustrates a container 31 within a depression 10, and with unbound build powder material 50 within the cavity 34. The second segment B illustrates a turbulent air flow 43 being created above the powder-filled container 31 within the depression 10. The second segment C illustrates the unbound build powder material 50 being fluidized, drawn upward, and evacuated from the cavity 34, leaving the rapidly-orodispersible container 31 with an emptied cavity 34 within the depression 10 as shown in fourth segment D.

In another embodiment a powder evacuation apparatus and system, instead of using a vacuuming system to remove the unbound powder material from a cavity, a rapidly-orodispersible container can instead be manually or mechanically inverted, and the powder material decanted from the container.

In another embodiment, a rapidly-orodispersible container can be subjected to high-frequency shaking or external sonication, whereby the unbound powder is substantially ejected from the cavity. Shaking or sonication may be applied when the container body is upright or inverted, and with a controlled frequency that empties the powder material from the cavity, without disturbing or damaging the bound-powder matrix of the container. Systems for shaking and/or sonicating objects are well known in the art.

In various embodiments, the powder evacuation apparatuses described herein are controlled by an automated controller system to evacuate unbound powder from built container bodies within the container-forming system.

In various embodiments, once unbound powder material is removed from a rapidly-orodispersible container, the emptied cavity can then be filled, either partially or fully, with one or more solid, powdered, or particulate medicaments. In another embodiment, each of the one or more medicaments can be a fine, coarse, or granulated powder. In another embodiment, each of the one or more medicaments can be water-soluble, or can be aqueous fluid-soluble, partially water-soluble, partially aqueous fluid-soluble, water-insoluble, or aqueous fluid-insoluble.

In another embodiment, one or more of the medicaments can be coated, taste-masked, agglomerated, and/or cross-linked. Components for taste-masking a medicament are described in U.S. Pat. No. 9,492,380, the disclosure of which is incorporated by reference in its entirety. Methods for taste-masking can include the addition of a coating, non-limiting examples of which include water-insoluble coatings, acid-soluble coatings, cationic polyacrylate coatings, polymethacrylate coatings, ion exchange resins coated with an ingestible polymer, ethyl cellulose coatings, and cellulose polymers. A medicament can be taste-masked using a waxy material, which is not an ionic polymer or copolymer, an acrylate polymer or copolymer, a methacrylate polymer or copolymer, or an enteric polymer. The waxy material can be selected from the group consisting of glyceryl dipalmitostearate (BIOGAPRESS VEGETAL), glyceryl distearate (PRECIROL®), glycerol palmitostearate, glyceryl dibehenate (COMPRITOL 888), mono and diglyceride mixture (GELEOL), glycerol monostearate, beeswax, carnauba wax, or cetyl esters wax. The waxy material can be glyceryl dipalmitostearate or glyceryl distearate. Processes and systems for forming pre-agglomerated powder particles are described in U.S. Pat. No. 9,314,429, the disclosure of which is incorporated by reference in its entirety.

In another embodiment, two or more medicaments can be combined into a powder composition and deposited into a single cavity. In another embodiment, a first medicament can be deposited into a first cavity, a second medicament can be deposited into a second cavity, and so on, such that a container having a plurality of cavities can contain a single medicament in each cavity, typically segregated and out of physical contact with the other. In another embodiment, the one or more medicaments can be combined with one or more solid pharmaceutically-acceptable excipients to form a composition. In another embodiment, the one or more solid pharmaceutically-acceptable excipients can be selected from any of the excipients described above. In another embodiment, the one or more solid pharmaceutically-acceptable excipients can comprise an unbound form of the powder material used to form the bound-powder matrix. In a further embodiment, the one or more solid pharmaceutically-acceptable excipients can consist only of the powder material.

In another embodiment, the solid medicament deposited into a cavity can be any powdered, particulate, crystalline, or agglomerated medicament. In another embodiment, the medicament can be selected from any of the medicaments approved for treatment by the Food and Drug Administration (FDA) (see e.g., "Approved Drug Products with Therapeutic Equivalence Evaluations", 40th Edition, U.S. Department of Health and Human Services (2020)). Non-limiting examples of pharmacological activities and/or medicaments include: local anesthetics, antiepileptic drugs and anticonvulsants; anti-Alzheimer's disease drugs; analgesics; antipodagrics; anti-hypertensive drugs; antiarrhythmic drugs: diuretic drugs; drugs for treating liver diseases; drugs for treating pancreatic diseases; antihistamines; anti-allergics; glucocorticoids; sex hormone drugs and contraceptives; hypoglycemic drugs; anti-osteoporosis drugs; antibiotics; sulfonamides; quinolones; and other synthetic antibacterial drugs; anti-tuberculous drugs; antiviral drugs; anti-neoplasm drugs; immune-modulators, cosmetically active agents; and anti-cancer drugs. In another embodiment, the medicament can be selected from the group consisting of: (R)-folitixorin, lidocaine, 11-di-deutero-ethyllinoleate, 16-dehydro-pregnenolone, 17-beta-estradiol, 2-iminobiotin, 3,5-diiodothyropropionicacid, 5-fluoro-2-deoxycytidine, 6-mercaptopurine, edotreotide, abacavir, abalone haemocyanin, abametapir, abediterol, abemaciclib, abexinostat, abiraterone, acalabrutinib, acamprosate, acamprosatecalcium, acarbose, acebilustat, aceclidine, aceclofenac, acehytisine hydrochloride, acemannan, aceneuramic acid, acetaminophen, acetylcysteine, acetylkitasamycin, acetyl-L-carnitinehydrochloride, acetylsalicylicacid, aciclovir, acipimox, acitazanolast, acitretin, aclidinium, aclidinium bromide, acolbifene, acorafloxacin, acotiamide, acrivastine, actarit, adapalene, adapalene, adefovirdipivoxil, ademetionine, adoair, afatinib, afimoxifene, afuresertib, agomelatine, ail denafilcitrate, aladorian, alalevonadifloxacin mesylate, alarelin acetate, alatrofloxacin mesylate, albendazole, albuterol sulfate, albuterpenoids, alcaftadine, aldoxorubicin, alectinib, alendronate, alendronate sodium, alendronate sodiumhydrate, alendronic acid, alfacalcidol, alfaxalone, alfentanil, alfuzosin, alisertib, aliskiren, alisporivir, alitretinoin, allantoin, alli sartani soproxil, allopurinol, almotriptan, alogliptin, alogliptin benzoate, alosetron, alpelisib, alphaketoglutarate, alphalipoic acid, alpha-lantitrypsin, alpha-cyclodextrin-stabilized sulforaphane, alprazolam, alprostadil, alprostadil alfadex, altiratinib, altretamine, altropane, aluminum sulfate, alvimopan, alvocidib, amantadine, amantadine hydrochloride, ambrisentan, ambroxol, ambroxol hydrochloride, amcasertib, amfetamine, amfetamine polistirex, amifampridine, amifampridine phosphate, amifostine, amikacin, amiloride, aminolevulinic, aminolevulinic acid, aminolevulinic acid hydrochloride, aminopterin, amiodarone, amiselimod, amisulpride, amitifadine hydrochloride, amitriptyline, amlexanox, amlodipine, amlodipine, amlodipinebesilate, amlodipine besylate, amlodipine camsylate, amlodipine maleate, amlodipine nicotinate, amlodipine orotate, ammonium lactate, amodiaquine, amorolfine, amosulalol, amoxicillin, amoxicillin hydrate, amphetamine, amphetamine aspartate, amphetamine sulfate, amphotericinB, amphotericinB cholesterylsulfate, amphotericinB lipid complex, ampicillin sodium, ampiroxicam, amrinone, amrubicin, amtolmetinguacil, anacetrapib, anagliptin, anagrelide, anamorelin, anastrozole, ancrod, androgen, andrographolide, anecortave, anidulafungin, aniracetam, anistreplase, anlotinib, antazoline, antiandrogens, antineoplaston A-10, antineoplaston AS2-1, antofloxacin hydrochloride, antroquinonol, apabetalone, apalutamide, apatinib mesylate, apaziquone, apilimod mesylate, apixaban, apomorphine, apomorphine hydrochloride, apremilast, aprepitant, apricitabine, aramchol, aranidipine, arasertaconazole, arasertaconazol enitrate, arbaclofen, arbaclofen placarbil, arbekacin, arbekacin sulfate, ardeparin sodium, arformoterol, argatroban, arhalofenate, arimoclomol, aripiprazole, aripiprazole lauroxil, arsenictrioxide, arsenious acid, artefenomel mesylate, artemether, artemotil, artenimol, arterolane maleate, artesunate, Artiss, asapiprant, asenapine, asimadoline, astodrimer, astragaloside, asunaprevir, ataciguat, ataluren, atazanavir, atazanavir sulfate, atenolol, atomoxetine, atorvastatin, atorvastatin calcium, atorvastatin strontium, atovaquone, atrasentan, atropine, auranofin, auriclosene, avacincaptadpegol sodium, avacopan, avanafil, avatrombopag, avibactam, avibactam sodium, AvidinOx, aviptadil, avitinib, avoral stat, axelopran, axitinib, azacitidine, azacytidine, azasetron, azelaicacid, azelastine, azelastine hydrochloride, azeliragon, azelnidipine, azilsartan, azilsartan medoxomil potassium, azilsartan trimethylethanolamine, azimilide, azithromycin, azithromycin lactobionate, aztreonam, aztreonam lysine, azvudine, baclofen, bafetinib, Baicalein, baicalin, BAK-freelatanoprost, balofloxacin, balsalazide, balsalazide sodium, bambuterol, barasertib, bardoxolone methyl, baricitinib, barnidipine, basmi sanil, batefenterol succinate, bazedoxifene, beclabuvir, beclometasone dipropionate, beclomethasone dipropionate, bedaquiline, bedoradrine, belinostat, beloranib, belotecan, bempedoic acid, benapenem, benazepril, bencycloquidium bromide, bendamustine, bendamustine hydrochloride, benidipine, benserazide, bentamapimod, benzalkonium chloride, benzhydrocodone, benznidazole, benzocaine, benzoylperoxide, benzydamineHCL, bepotastine, bepotastine calciumdihydrate, bepotastine salicylate, beractant, beraprost sodium, besifloxacin, besifovir, besipirdine, beta-elemene, betahistine, betaine anhydrous, betamethasone, betamethasone butyrate propionate, betamethasonedipropionate, betamethasone valerate, betamipron, betaxolol, betaxolol hydrochloride, bethanechol, betrixaban, bevacizumab, bexagliflozin, bexarotene, bezafibrate, biafungin, biapenem, bicalutamide, bicizar, bictegravir, bicyclol, bilastine, bimatoprost, binimetinib, biotin, birabresibdihydrate, biskalcitrate potassium, bismuth subgallate, bismuthyl ecabet, bisnorcymserine, bisoprolol, bisoprolol fumarate, bitespiramycin, bixalomer, bleomycin, blonanserin, boanmycin hydrochloride, boceprevir, bortezomib, bosentan, bosentan hydrate, bosutinib, bovactant, brexpiprazole, briciclib sodium, brigatinib, brilacidin, brimapitide, brimonidine, brincidofovir, brinzolamide, brivanibalaninate, brivaracetam, brivudine, brolucizumab, bromazepam, bromfenac, bromfenac sodium, bromocriptine, bronchostat, brotizolam, bryostatin-1, bucindolol, bucladesine, budesonide, budipine, buflomedil, bulaquin, bunazosin, buparlisib, bupivacaine, bupivacaine hydrochloride, buprenorphine, buprenorphine hydrochloride, bupropion, bupropion hydrochloride, burixafor, buserelin acetate, buspirone, buspirone hydrochloride, busulfan, busulfex, butenafine, butorphanol tartrate, butylphthalide, cabazitaxel, cabergoline, cabotegravir, cabozantinib S-malate, cadazolid, cadrofloxacin, caffeine, caffeine citrate, cafnea, cafusertib hydrochloride, calcipotriol, calcitriol, calcium acetate, calciumfolinate, calcium levofolinate, calcium polycarbophil, calfactant, calmangafodipir, calsurf, camicinal, camostat mesylate, camptothecin, canagliflozin, candesartan, candesartan cilexetil, canfosfamide, cangrelor, cannabidiol, capecitabine, capmatinib, capsaicin, captopril, carbamazepine, carbetocin, carbidopa, carbinoxamine, carbocysteine, carboplatin, cardidopa, carfilzomib, carglumicacid, cariprazine, carisbamate, carmustine, carotegastmethyl, carteolol, carteolol hydrochloride, carumonam, carvedilol, carvedilolphosphate, caspofungin, catechin, cebranopadol, cediranib, cefaclor, cefadroxil, cefathiamidine, cefazolin sodium pentahydrate, cefcapene, cefdinir, cefditorenpivoxil, cefepime, cefepime dihydrochloride, cefetametpivoxil hydrochloride, cefiderocol, cefilavancin, cefminox, cefoperazone, cefoperazone sodium, cefoselis, cefotaxime, cefotaxime sodium, cefotiam, cefozopran, cefpirome, cefpodoxime, cefprozil, ceftaroline, ceftaroline fosamil, ceftazidime, ceftibuten, ceftobiprole medocaril, ceftolozane sulfate, ceftriaxone, ceftriaxone sodium, cefuroxime, cefuroxime sodium, celecoxib, celgosivir, celiprolol, cellprotect, cenestin, cenicriviroc, censavudine, centanafadine, cephalosporin, ceralifimod, cerdulatinib, ceritinib, ceriumnitrate, cetilistat, cetirizine, cetraxate, cevimeline, chenodeoxycholic acid, chlocibutamine, chlorhexidine, chlormadinone acetate, chlorogenicacid, chloroquine, chloroxoquinoline, chlorpheniramine, chlorpheniramine maleate, chlorpheniramine polistirex, chlortalidone, chlorthalidone, cholecalciferol, cholic acid, choline alfoscerate, choline diepalrestat, choline fenofibrate, ciclesonide, ciclopiroxolamine, ciclosporin, cidofovir, cidoxepin, cilastatin, cilazapril, cilnidipine, cilostazol, cimetidine, cinacalcet, cinepazide maleate, cinhyaluronate sodium, cinitapride tartrate, cipargamin, ciprofibrate, ciprofloxacin, ciprofloxacin hydrochloride, ciraparantag, circadin, cisatracurium besilate, cisplatin, citalopram, citalopram hydrobromide, citicoline, citrulline, cladribine, clarithromycin, clavulanate potassium, clavulanic acid, clazosentan, clevidipine, clevudine, clindamycin, clindamycin hydrochloride, clindamycin phosphate, clioquinol, clobazam, clobetasolpropionate, clobetasolpropionatefoam, clodronic acid, clofarabine, clofazimine, clomipramine, clomipramine hydrochloride, clonazepam, clonidine, clonidine hydrochloride, clopidogrel, clopidogrel besylate, clopidogrel bi sulfate, clopidogrel camsylate, clopidogrel hydrogensulfate, clopidogrel napadisilate, clopidogrel resinate, clotrimazole, clozapine, cobamamide, cobicistat, cobimetinib, cobiprostone, codeine, codeine polistirex, colchicine, colecalciferol, colesevelam, colestilan, colforsin daropate, colfosceril palmitate, colistimethate sodium, conivaptan, copanlisib, copperhistidine, cortexolone 17alpha-propionate, cositecan, crenolanib, cridanimod sodium, crisaborole, crizotinib, crofelemer, crolibulin, cromoglicic acid, cromolyn sodium, cutamesine dihydrochloride, cyanocobalamin, cyclizine lactate, cyclobenzaprine hydrochloride, cyclophosphamide, cyclophosphamide monohydrate, cyclosporin, cyproterone, cyproterone acetate, cytarabine, cytarabine ocfosfate, dabigatran etexilate, dabrafenib, daclatasvir, dacomitinib, dalbavancin, dalcetrapib, dalfampridine, dalfopristin, dalteparin sodium, danaparoid sodium, danazol, danirixin, danoprevir, dantrolene sodium, danusertib, dapaconazole, dapagliflozin, dapagliflozin propanediol, dapiprazole, dapivirine, dapoxetine, daprodustat, dapsone, darifenacin, darinaparsin, darunavir, dasabuvir, dasatinib, dasotraline, daunorubicin, decitabine, decuprate, defactinib, deferasirox, deferiprone, deferoxamine mesylate, deflazacort, deflexifol, delafloxacin, delamanid, delapril, delapril hydrochloride, delavirdine, denibulin, deoxyandrographolide, dematansulfate, desflurane, desipramine hydrochloride, desloratadine, desmopressin, desmopressin acetate, desogestrel, desonide, desvenlafaxine, deudextromethorphan hydrobromide, deuteporfin, deuterated levodopa, deuteratedvenlafaxine, deutetrabenazine, dexamethasone, dexamethasone acetate, dexamethasone cipecilate, dexamethasone palmitate, dexamethasone sodiumphosphate, dexamfetamine, dexanabinol dexferrum, dexketoprofen trometamol, dexlansoprazole, dexmedetomidine, dexmethylphenidate, dexpramipexole, dexrazoxane, dexsotalol, dextroamphetamine saccharate, dextroamphetamine sulfate, dextromethorphan, dextromethorphan hydrobromide, dextropropoxyphene, diacerein, diamorphine hydrochloride, dianhydrogalactitol, diazepam, diazoxidecholine, diclofenac, diclofenac potassium, diclofenac sodium, diclofenamide, dicycloplatin, didanosine, dienogest, difluprednate, digoxin, dihomogamma-linolenic acid, dihydroergocristine, dihydroergotamine, dihydroergotamine mesylate, diltiazem, diltiazem hydrochloride, dimesna, di methyl fumarate, dimiracetam, dinoprostone, diphenylcyclopropenone, dipraglurant, dipyridamole, diquafosoltetra sodium, dirithromycin, disufentonsodium, disulfiram, dithranol, d-methadone, docarpamine, docetaxel, dociparstat, docosanol, dofetilide, dolasetron, dolutegravir, domperidone, donafenib tosylate, donepezil, donepezil hydrochloride, dopamine, doravirine, doripenem, dorzolamide, dorzolamide hydrochloride, dosmalfate, doxacurium chloride, doxazosin, doxazosin mesylate, doxepin hydrochloride, doxercalciferol, doxifluridine, doxofylline, doxorubicin, doxorubicin hydrochloride, doxycycline, doxycycline hyclate, doxylamine succinate, dronabinol, dronedarone, drospirenone, droxidopa, D-tagatose, duloxetine, duloxetine hydrochloride, dutasteride, duvelisib, ebastine, eberconazole, ebselen, ecabet, econazolenitrate, ecopipam, edaravone, edivoxetine, edonerpic maleate, edoxaban, efatutazone, efavirenz, efinaconazole, eflornithine, efonidipin hydrochloride, egualen sodium, eicosapentaenoic acid monoglycerides, elafibranor, elagolix elamipretide, elbasvir, eldecalcitol, eleclazine, elesclomol sodium, eletriptan, eliglustattartrate, elobixibat, eltrombopag, eluxadoline dihydrochloride, elvitegravir, emdogain, emedastine, emeramide, emixustat, emodepside, empagliflozin, emricasan, emtricitabine, enalapril, enalaprilmaleate, enasidenib, encenicline, enclomifene citrate, encorafenib, endoxifen, enobosarm, enoxacin gluconate, enoxaparin sodium, enprostil, entacapone, entasobulin, entecavir, entecavir maleate, entinostat, entospletinib, entrectinib, enzalutamide, enzastaurin, epacadostat, epalrestat, eperisone, epetraborole, ephedrine sulfate, epinastine hydrochloride, epinephrine, epirubicin, epirubicin hydrochloride, episalvan, epitinib, eplerenone, epoprostenol, episteride, eprodisate, eprosartan, eptaplatin, eravacycline, erdafitinib, erdosteine, eribulin mesylate, erlotinib, ertapenem, erteberel, ertugliflozin, erythromycin, erythromycin acistrate, erythromycin stinoprate, escitalopram, esketamine, esketamine hydrochloride, eslicarbazepine acetate, esmolol hydrochloride, esomeprazole, esomeprazole magnesium, esomeprazole strontium, esomeprazole, estetrol, estradiol, estradiol acetate, estradiol cypionate, estradiol valerate, estrodiol, estrogen, esuberaprost sodium, eszopiclone, etamicastat, ethambutol hydrochloride, ethaselen, ethinylestradiol, ethylhydrogenfumarate calcium, ethylhydrogenfumarate magnesium, ethylhydrogenfumara tezinc, ethynylestradiol, etidronicacid, etimicin sulfate, etirinotecanpegol, etizolam, etodolac, etonogestrel, etoposide, etoposide phosphate, etoricoxib, etravirine, etripamil, eupatilin, evenamide hydrochloride, everolimus, evofosfamide, evogliptin, exemestane, exendin (9-39), exeporfinium chloride, ezatiostat, ezetimibe, ezutromid, fadolmidine, fadrozole, faldaprevir, falecalcitriol, famciclovir, famitinib, famotidine, fampridine, faropenem, fasitibant chloride, fasoracetam, fasudil, fasudil hydrochloride, fasudil mesylate, favipiravir, febarbamate, febuxostat, fedovapagon, felbamate, felbinac trometamol, felodipine, femitra, fenfluramine hydrochloride, fenobam, fenofibrate, fenofibric acid, fenoldopam, fenoterol, fenretinide, fentanyl, fentanyl citrate, fenticonazole, fermagate, ferriccitrate, ferricmaltol, ferumoxytol, fesoterodine fumarate, fevipiprant, fexinidazole, fexofenadine, fibrinsealant, fibrinogen, fibrinogensealant, fidaxomicin, filanesib, filgotinib, filociclovir, fimaporfin, fimasartan, finafloxacin, finafloxacin hydrochloride, finasteride, finerenone, fingolimod, fipamezole, firtecanpegol, flecainide, fleroxacin, flibanserin, flomoxef, floxuridine, fluazolepali, fluconazole, fludarabine, flumatinib, flumazenil, flunisolide, fluocinolone acetonide, fluocinonide, fluorapacin, fluorouracil, fluoxetine, fluoxetine hydrochloride, flupirtine, flurbiprofen, flurbiprofenaxetil, flurbiprofen sodium, flurithromycin, fluticasone, fluticasone furoate, fluticasone propionate, flutrimazole, fluvastatin, fluvoxamine, folic acid, folinate, foliumginkgo, fomepizole, fonadelpar, fondaparinux sodium, foretinib, formestane, formoterol, formoterol fumarate, forodesine, fosamprenavir, fosaprepitant, fosbretabulin, fosbretabulin disodium, fosfluconazole, fosfomycin, fosfomycindi sodium, fosfomycintrometamol, fosinopril, fosinopril sodium, fosmidomycin, fosphenytoin, fospropofol, fosravuconazole, fostamatinib, fostemsavir trometamine, fotagliptin benzoate, fotemustine, frovatriptan, fruquintinib, fudosteine, fulvestrant, funapide, furosemide, fusidic acid, gabapentin, gabapentinenacarbil, gabexate mesylate, gacyclidine, gadobutrol, gadoversetamide, gadoxetate disodium, galantamine, galeterone, galidesivir, gallium nitrate, galunisertib, gambogic acid, ganaxolone, ganciclovir, ganetespib, ganirelix acetate, garenoxacin, gatifloxacin, gatifloxacin mesylate, gedatolisib, gefitinib, gemcabene, gemcitabine, gemcitabine hydrochloride, gemfibrozil, gemifloxacin, gemigliptin, gemigliptintartaric acid, genistein, gentamicin, gentiopicrin, gepirone, gepotidacin, gestodene, gestrinone, timolol maleate, gilteritinib, gimeracil, ginsenosideC-K, ginsenosideRg3, givinostat, glasdegib, glatiramer acetate, glecaprevir, glesatinib glycolate, glibenclamide, gliclazide, glimepiride, glipizide, glufosfamide, glutamine, glutathionarsenoxide, glycerol phenylbutyrate, glycopyrronium, glycopyrronium bromide, glycopyrronium tosylate, glycyrrhizi cacid, ganglioside, golotimod, gosogliptin, granisetron, granisetron hydrochloride, grazoprevir, guaifenesin, guaimesal, guanfacine, gusperimus trihydrochloride, haemophilusinfluenzae, halobetasol propionate, halofantrine, halometasone, healon, hematoporphyrin, hemearginate, hemocoagulase acutus, heparin, Herbiron, hetrombopag, hextend, higenaminehydrochloride, histamine dihydrochloride HPPHphotosensitizer, humanapotransferrin, humanplasminogen, huperzineA, hyaluronate sodium, hydralazine, hydrochloride, hydrochlorothiazide, hydrocodone, hydrocodone bitartrate, hydrocodone polistirex, hydrocortisone, hydrogenperoxide, hydromorohone, hydromorphone hydrochloride, hydroxocobalamin, hydroxycarbamide, hydroxychloroquine, hydroxyprogesterone caproate, hydroxysafflor yellowA, hylastan, hypericin, hypoestoxide, ibandronate, ibandranic acid, iberogastN, ibodutant, ibrutinib, ibudilast, ibuprofen, ibutilide, ibutilide fumarate, icosabutate, icosapent, icosapentethyl, icosapentethyl ester, icotinibhydrochloride, idalopirdine, idasanutlin, idebenone, idelali sib, idoxuridine, idronoxil, ifetroban, ifetrobansodium, iguratimod, ilansoprazole, ilaprazole, iloperidone, iloprost, iloprostbetadexclathrate, imatinib, imatinibmesylate, imeglimin, imidafenacin, imidapril, imidazole salicylate, imidol hydrochloride, imigliptin dihydrochloride, imipenem, imiquimod, imisopasem manganese, imrecoxib, incadronic acid, incobotulinumtoxin, indacaterol, indacaterol maleate, indapamide, indeloxazine, Indimitecan, indinavir, indisetron, indometacin, indoramin, indotecan, indoximod, inecalcitol, infigratinib, Ingavirin, ingenolmebutate, inhaled sodium nitrite, ferric carboxymaltose, inosine, intepirdine, iodiconazole, ipatasertib dihydrochloride, ipragliflozin, ipratropium, ipratropium bromide, iptakalim, irbesartan, irinotecan, irinotecan hydrochloride, irinotecan sucrosofate, irofulven, iron isomaltoside1000, iron protein succinylate, irosustat, irsogladine maleate, isavuconazonium chloride/sulfate, isodibut, isoflurane, isoniazid, isopropylunoprostone, isosorbidedi nitrate, isosorbide mononitrate, isosteviol, isothiafludine, isotretinoin, isradipine, istaroxime, istradefylline, itacitinib, itopride hydrochloride, itraconazole, ivabradine hemisulfate, ivabradine hydrochloride, ivacaftor, ivermectin, ivosidenib, aflibercept, ixabepilone, ixazomib citrate, kallikrein, kangbeide, ketamine, ketanserin, ketoconazole, ketoprofen, ketorolac, ketorolac tromethamine, ketotifen, kevetrin, kukoamine Bmesylate, L-4-chlorokynurenine, lacidipine, lacosamide, lactitol, ladarixin, ladostigil, laflunimus, lafutidine, lamivudine, lamotrigine, landiolol, landiolol hydrochloride, laninamivir octanoate, lanoconazole, lansoprazole, lanthanum carbonate, lapatinib, laquinimod, laromustine, lasmiditan, lasofoxifene, latanoprost, latanoprostenebunod, lauflumide, ledipasvir, lefamulin, leflunomide, lemborexant, lenalidomide, lentinan, lentinansulfate, lentinanviral, lenvatinib mesylate, lercanidipine, lesinurad, leteprinim, letermovir, letrozole, leucine, leuprorelin acetate, levalbuterol, levalbuterol hydrochloride, levami sole, levamlodipine, levamlodipine besylate, levamlodipine maleate, levetiracetam, levobupivacaine, levocabastine, levocabastine hydrochloride, levocarnitine, levocetirizine dihydrochloride, levodopa, levodoxazosin mesylate, levofloxacin, levoketoconazole, levomilnacipran, levonadifloxacin arginine salt, levonorgestrel, levonorgestrel butanoate, levo-phencynonate hydrochloride, levornidazole, levorphanol, levosimendan, levothyroxine sodium, levotuss, L-glutamine, lidocaine, lifitegrast, ligustrazine hydrochloride, limaprost, linagliptin, linezolid, liothyronine, liothyronine sodium, lipobean, liposomal curcumin, lipoteichoic acid, liranaftate, lisdexamfetamine, lisinopril, lisofylline, lisuridehydrogen maleate, lithiumcitrate, lithiumsuccinate, lixivaptan, lobaplatin, lobeglitazone, lodenafil carbonate, lofexidine, lomefloxacin, lomerizine, lomerizine dihydrochloride, lomitapide, lonafarnib lonidamine, loperamide, loperamideoxide, lopinavir, loratadine, lorazepam, lorcaserin, lorediplon, lorlatinib, L-ornithineL-aspartate, lornoxicam, losartan, losartan potassium, losmapimod, loteprednoletabonate, lovastatin, loxapine, loxoprofen, L-praziquantel, lubiprostone, lucanthone, lucerastat, lucinactant, lucitanib hydrochloride, luliconazole, lumacaftor, lumateperone toluene sulfonate, lumefantrine, lumiracoxib, lunacalcipol, lurasidone, lurbinectedin, luseogliflozin hydrate, lusutrombopag, lysine acetylsalicylate, macimorelin, macitentan, mafenide, magnesium carbonate, magnesium isoglycyrrhizinate, mangafodipir, manidipine, manidipine dihydrochloride, mannitol, maraviroc, maribavir, marizomib, masilukast, masitinib, mavoglurant, maxacalcitol, mebendazole, mebiphon, mecamylamine, mecamylamine hydrochloride, mechlorethamine, mecobalamin, medroxyprogesterone, medroxyprogesteroneacetate, mefloquine, megestrol, megestrolacetate, meisuoshuli, melevodopa, meloxicam, melphalan, melphalanflufenamide hydrochloride, memantine, memantine hydrochloride, menadione sodium bisulfite, menatetrenone, mepacrine, mequinol, mercaptamine, mercaptamine bitartrate, mercaptamine hydrochloride, mercaptopurine, merestinib, meropenem, merotocin, mesalamine, mesalazine, metacavir, metadoxine, metamizolesodium, metaxalone, metergoline, metformin, metformin hydrochloride, methadone, methazolamide, methotrexate, methoxyflurane, methylaminolevulinate hydrochloride, methylnaltrexone bromide, methylnaltrexone, methylphenidate, methylphenidate hydrochloride, methylprednisolone, methylprednisolone aceponate, methylthioninium chloride, metirosine, metoclopramide, metoprolol, metoprolol succinate, metrifonate, metronidazole, metyrapone, mexiletine, mibefradil, miconazole, miconazole nitrate, midazolam, midazolam hydrochloride, midodrine, midostaurin, mifamurtide, mifepristone, migalastat, miglitol, miglustat, milnacipran, milrinone, miltefosine, minaprine, minocycline, minocycline hydrochloride, minodronic acid, minoxidil, mirabegron, miriplatin hydrate, mirodenafil, mirodenafil hydrochloride, mirogabalin, mirtazapine, misoprostol, mitiglinide, mitomycin, mitoxantrone, mitoxantrone hydrochloride, mivotilate, mizolastine, mizoribine, mocetinostat dihydrobromide, moclobemide, modafinil, doxycycline, modipafant, moexipril, mofezolac, molidustat, molindone hydrochloride, momelotinib, mometasone, monepantel, monoammonium glycyrrhizinate, monobenzone, monosodium alphaluminol, monoterpene perillyl alcohol, montelukast, montelukast sodium, montmorillonite, moracizine, morinidazole, morphine, morphine glucuronide, morphine pitavastatin, morphine sulfate, morphothiadine mesilate, mosapride, motolimod, moxidectin, moxifloxacin, moxifloxacin hydochloride, moxonidine, moxonidine hydrochloride, mozavaptan, muparfostat sodium, mupirocin, mycobactovir, mycophenolatemofetil, myristylnicotinate, nabilone, nabiximols, nabumetone, N-acetylcysteine, nacystelyn, nadifloxacin, nadolol, nadroparin calcium, naftifine hydrochloride, naftopidil, nalbuphine, nalbuphine sebacate, naldemedine, nalfurafine, nalmefene, naloxegol, naloxone, naloxone hydrochloride, naltrexone, naltrexone hydrochloride, naluzotan, nandrolone decanoate, napabucasin, naphazoline, naphthoquine, naproxen, naproxen sodium, naquotinib mesylate, naratriptan, narlaprevir, nasapaque, nasaruplase, nastorazepide calcium, nateglinide, navamepent, nazartinib, nebivolol, necuparanib, nedaplatin, nedocromil, nelarabine, nelfinavir, nelotanserin, nemonapride, nemonoxacin, neoandrographolide, neosaxitoxin, neostigmine methyl sulfate, nepadutant, nepafenac, nepicastat, nepolong, neramexane, neratinib, neridronic acid, netarsudil, netilmicin, netupitant, nevirapine, niacin, nicardipine, nicergoline, nicorandil, nicotiflorin, nicotine, nicotinicacid, nicousamide, nifedipine, nifekalant, nifeviroc, Nifurtimox, nifurzide, nikkomycin, nilotinib, nilutamide, nilvadipine, nimesulide, nimodipine, nimorazole, ningetinib, nintedanib, niraparib, nisoldipine, nitazoxanide, nitisinone, nitrendipine, nitricoxide, nitroglycerin, nitroglycerine, nizatidine, nokxaban, nolatrexed, nomegestrol acetate, norelgestromin, norepinephrine, norethindrone, norethindrone acetate, norethindrone enantate, norethisterone, norethisterone acetate, norfloxacin, norgestimate, noribogaine, norursodeoxycholic acid, obeticholicacid, octenidine, octohydroaminoacridine succinate, octreotide, octreotide hydrochloride, odalasvir, odanacatib, odiparcil, ofloxacin, olanzapine, olaparib, olesoxime, oliceridine, olmesartan, olmesartan cilexetil, olmesartan medoxomil, olodaterol, olodaterol hydrochloride, olopatadine, olopatadine hydrochloride, olprinone, olsalazine, oltipraz, omacetaxine mepesuccinate, omadacycline, omarigliptin, omaveloxolone, ombitasvir, omecamtivmecarbil, omega-3 carboxylicacids omeprazole, omigapil, omoconazole, onalespib, onapristone, ondansetron, ondelopran, opicapone, opipramol, methylphenidate, orcinoside, orilotimod, oritavancin, orlistat, ornithine phenyl acetate, ornoprostil, ortataxel, orteronel, orthovisc, orvepitant, oseltamivir, osilodrostat, osimertinib, Osiris *Phleum pratense*, ospemifene, oteracil potassium, oteseconazole, oxaliplatin, oxaloacetic acid, oxandrolone, oxazepam, oxcarbazepine, oxfendazole, oxidizedglutathione sodium, oxiracetam, oxybutynin, oxybutynin hydrochloride, oxycodone, oxycodone hydrochloride, oxymetazoline, oxymetazoline hydrochloride, oxymorphone, oxytocin, ozagrel, ozagrel hydrochloride, ozagrelsodium, ozanimod, ozenoxacin, paclitaxel, paclitaxel poliglumex, pacritinib, palbociclib, paliperidone, paliperidone palmitate, palmidrol, palonosetron, palovarotene, pamidronate disodium, pancrelipase, panipenem, panobinostat, pantoprazole, paracetamol, parecoxib, paricalcitol, paritaprevir, parnaparin sodium, parogrelil, paromomycin, paroxetine, paroxetine hydrochloride hemihydrate, paroxetine mesylate, patiromer calcium, patupilone, pazopanib, pazufloxacin, pazufloxacin mesylate, pefcalcitol, peficitinib, pegylatedapo-filgrastim, pelubiprofen, pemafibrate, pemetrexed disodium, pemirolast, pemirolast potassium, pemirolast sodium, penciclovir, penehyclidine hydrochloride, pentamidine, pentetate calcium trisodium, pentetatezinc tri sodium, pentetrazol, pentosan polysulfate sodium, pentostatin, pentoxifylline, peramivir, perampanel, perchlozone, peretinoin, perflenapent, perflubronemulsion, perfluorooctyl bromide, pergolide, perhexiline maleate, perifosine, perindopril, perindopril arginine, perospirone, pevonedistat, pexidartinib, PhagoBioDerm, phenchlobenpyrrone, phenethyl isothiocyanate, phenoxybenzamine hydrochloride, phentermine, phentermine hydrochloride, phentolamine mesylate, phenylbutyrate, phenylephrine, phenyl ephrine hydrochloride, phenytoin, phosphazid, pibrentasvir, picibanil, picroliv, picropodophyllin, pidotimod, pilocarpine, pilocarpine hydrochloride, pilsicainide, pimasertib hydrochloride, pimavanserin, pimecrolimus, pimobendan, pinocembrin, pinometostat, pioglitazone, pioglitazone hydrochloride, pipamperone, pipecuronium, piperacillin, piperacillin sodium, piperaquine, piperaquine phosphate, piperidone hydrochloridum, piperine, piperphentonamine, piracetam, pirarubicin, pirfenidone, phmenol, piromelatine, pirotinib, piroxicam, piroxicambetadex, pitavastatin, pitavastatin calcium, pitolisant, pixantrone, plazomicin, pleconaril, plerixafor, plinabulin, pocapavir, hydromorphone, podofilox, polaprezinc, polmacoxib, polydatin, polyoxidonium, pomaglumetad methionil, pomalidomide, ponatinib, ponesimod, porfimer sodium, posaconazole, posiphen, potassium bicarbonate, potassium citrate, potassium clavulanate, poziotinib, pracinostat, pradefovir, pralatrexate, pramipexole, pramiracetam, pranlukast, pranlukast hydrate, prasterone, prasugrel, pravastatin, prazosin, prednimustine, prednisolone, prednisoloneacetate, prednisolone sodiumphosphate, prednisone, pregabalin, prempro, presatovir, pretomanid, previdersin, prexasertib, pridopidine, prilocaine, pritelivir, procaterol hydrochloride, prochlorperazine, prochlorperazinemaleate, profezyme, progesterone, progestogen, progestogendienogest, proguanil, promethazine, promitil, propafenone, propagermanium, propofol, propranolol, propranolol hydrochloride, prostat, proxodolol, prucalopride, prulifloxacin, prurisol, prussianblueinsoluble, pseudoephedrine, pseudoephedrine hydrochloride, puerarin, puquitinib mesylate, pyrazinamide, pyridoxamine dihydrochloride, pyridoxine hydrochloride, pyrimethamine, pyronaridine, pyrroltinibmaleate, quazepam, quetiapine fumarate, quetiapine, quinagolide hydrochloride, quinapril hydrochloride, quinidine sulfate, quinine sulfate, quinupristin, quisinostat, quizartinibdi hydrochloride, rabeprazole, rabeprazolesodium, rabeximod, racecadotril, radezolid, radotinib, ralfinamide, ralimetinib, ralinepag, raloxifene, raltegravir, raltitrexed, ramatroban, ramelteon, ramipril, ramosetron, ranitidine, ranitidine bismuth citrate, ranolazine, rasagiline, ravidasvir hydrochloride, raxatrigine, rebamipide, rebastinib, reboxetine, reboxetine mesylate, recilisib sodium, recoflavone, redaporfin, ibuprofen, naproxen, glycopyrronium bromide, refametinib, regorafenib, relebactam, relenopride, relugolix, remeglurant, remifentanil, remifentanil hydrochloride, remimazolam, remimazolam tosylate, remogliflozin etabonate, repaglinide, reparixin, repirinast amlexanox, chlorcyclizine hydrochloride, bucillamine, guanabenz, mazindol, naltrexone, nitisinone, ondansetron, phacetoperane, retigabine, rosiglitazone, sodium phenylbutyrate, resiniferatoxin, resiquimod, resminostat, resveratrol, retagliptin, retapamulin, retigabine, retinoicacid, retosiban, revaprazan, revefenacin, reviparin sodium, rhein, rhenium-186 etidronate, ribavirin, ribociclib, ricolinostat, ridinilazole, ridostin, rifabutin, rifampicin, rifamycin, rifapentine, rifaximin, rigosertib sodium, rilapladib, rilpivirine, rilpivirine hydrochloride, riluzole, rimantadine, rimeporide, rimexolone, riociguat, ripasudil hydrochloride hydrate, risedronate sodium, risperidone, ritonavir, rivaroxaban, rivastigmine, rivipansel sodium, rizatriptan, rizatriptan benzoate, rmulation, rociletinib, roflumilast, rokitamycin, rolapitant, romurtide, ronacaleret, roneparstat, ronopterin, ropinirole, ropinirole hydrochloride, ropivacaine, rosebengal sodium, rosiglitazone, rosiglitazone maleate, rosiglitazone sodium, rostafuroxin, rosuvastatin, rosuvastatin calcium, rotigotine, rovatirelin, roxadustat, roxithromycin, rubitecan, rucaparib phosphate, rufinamide, rufloxacin, rupatadine, ruxolitinib, S-(–)-ornidazole phosphate disodium, sabarubicin, sacubitril, safinamide, salbutamol, salbutamol sulfate, salicyclic acid, salmeterol, salmeterol xinafoate, salubrinal, salvicine, samarium (153Sm) lexidronam, samidorphan, S-amlodipine nicotinate, sapacitabine, sapropterin, sapropterin dihydrochloride, saquinavir, saracatinib, sarecycline, saroglitazar, sarpogrelate hydrochloride, savolitinib, saxagliptin, scopolamine, scorpionvenom, omega-3 polyunsaturated fatty acid, secnidazole, segesterone acetate, selegiline, selegiline hydrochloride, selepressin, selexipag, seliciclib, selinexor, selisistat, selumetinib, selurampanel, sepranolone, seratrodast, serlopitant, sertaconazole, sertaconazole nitrate, sertindole, sertraline, sertraline hydrochloride, setipiprant, sevelamer carbonate, sevelamer hydrochloride, seviteronel, sevoflurane, sevuparin sodium, sibutramine maleate, sibutramine mesylate, sildenafil, sildenafil citrate, silibinin dihydrogen succinate, silmitasertib, silodosin, silver sulfadiazine, simeprevir, simmitecan hydrochloride, simotinib hydrochloride, simvastatin, sinotecean, siponimod, sirolimus, sitafloxacin, sitagliptin, sitagliptinphosphate, sivelestat, sizofiran, smilagenin, S-modafinil, sobuzoxane, sodium aescinate, sodium ascorbate, sodium benzoate, sodium bicarbonate, sodium chromoglycate, sodium ferricgluconate complex, sodium glycididazole, sodium gualenate, sodium hyaluronate, sodium ibandronate, sodium nitrate, sodium nitrite, sodium oxybate, sodium phenylacetate, sodium phenylbutyrate, sodium polysulthionate, sodium prasteronesulfate, sodium pyruvate, sodium taurocholate, sodium thiosulfate, sodium zirconiumcyclosilicate, sofosbuvir, sofpironium bromide, solabegron, solifenacin, solithromycin, sonidegib, sonoli sib, sophocarpine, sophoridine hydrochloride, sorafenib, sorbitol, sotagliflozin, sotirimod, sotrastaurin, sotylize, sovaprevir, sparfloxacin, sparsentan, spebrutinib, spirapril, spironolactone, squalamine, stannsoporfin, stavudine, S-tenatoprazole, stepronin, stiripentol, streptozocin, strontium malonate, strontium ranelate, succinic acid, sucralfate, sucroferric oxyhydroxide, sufentanil, suftalanzinc, sugammadex, sulbactam, sulbactam sodium, sulcardine sulfate, sulfamethoxypyrazine, sulfasalazine, sulfatinib, sulfonylurea, sulforaphane, sulfotanshinone sodium, sulindac, sulodexide, sulphamethoxazole, sulthiame, sumatriptan, sumatriptan succinate, sunitinib, sunstone, suplasyn, suplatast tosilate, suramin sodium, verapamil hydrochloride, rilpivirine, sutezolid, suvorexant, tacalcitol, tacrine, tacrolimus, tadalafil, tafamidis, tafenoquine, tafluprost, tafoxiparin sodium, taladegib, talaporfin, talazoparib, talipexole, taltirelin, tamibarotene, tamoxifen, tamsulosin, tamsulosin hydrochloride, tandospirone, tanespimycin, tapentadol, tarafenacin, tarenflurbil, tarloxotinib bromide, taselisib, tasimelteon, tasquinimod, tavaborole, tavilermide, tazarotene, tazemetostat, tazobactam, tazobactam sodium, tebipenem pivoxil, tecarfarin, tecovirimat, tectorigenin sodiumsulfonate, tedisamil, tedizolid phosphate, tefinostat, tegafur, tegaserod, teicoplanin, telaprevir, telapristone acetate, telatinib, telbivudine, telithromycin, telmisartan, telotristatetiprate, temanogrel, temocapril, temoporfin, temozolomide, temsirolimus, tenalisib, tenapanor, teneligliptin, tenofovir, tenofoviralafenamide, tenofovirdipivoxil fumarate, tenofovir disoproxil aspartate, tenofovir disoproxil fumarate, tenoxicam, tepotinib, teprenone, terameprocol, terazosin, terbinafine, terbinafine hydrochloride, terguride, teriflunomide, tesevatinib, tesofensine, testosterone, testosterone undecanoate, tetrabenazine, tetracaine, tetracaine hydrochloride, tetrahydrocannabidiol, tetrathiomolybdate, tetryzoline, tezacaftor, thalidomide, theliatinib, theophylline, therapeutic, thiazide, thienorphine hydrochloride, thiotepa, thrombin, thromboreductin, thyroxine, tiagabine, tianeptine, tibolone, ticagrelor, ticlopidine, tigecycline, tiludronatedi sodium, timolol, timolol maleate, tindamax, tinidazole, tinzaparin sodium, tioconazole, tiopronin, tiotropium bromide, tiotropium bromide monohydrate, tipelukast, tipepidine hibenzate, tipifarnib, tipiracil hydrochloride, tipranavir, tirapazamine, tirasemtiv, tirilazad, tirofiban, tirofiban hydrochloride, tivantinib, tivozanib, tizanidine, tobramycin, tocofersolan, tocoretinate, tofacitinib, tofogliflozin, tolcapone, tolimidone, tolperisone, tolterodine, tolterodine tartrate, tolvaptan, tonabersat, topiramate, topiroxostat, topotecan, topotecan hydrochloride, torasemide, toreforant, toremifene, tosedostat, tosufloxacin, totrombopag, tozadenant, trabectedin, trabodenoson, tradipitant, tramadol, tramadol hydrochloride, trametinib, trandolapril, tranexamic acid, tranilast, transcrocetinate-sodium, transepithelial riboflavin, trantinterol hydrochloride, travoprost, trazodone, trehalose, trelagliptin succinate, treosulfan, treprostinil, treprostinil diolamine, tretinoin, triamcinolone acetonide, triapine, triazolam, tribendimidine, trichlormethiazide, triciribine, triclabendazole, triclocarban, trientine hydrochloride, trifarotene, trifluridine, triflusal, triheptanoin, trilostane, trimebutine3-thiocarbamoyl-benzenesulfonate, trimebutine tosylate, trimegestone, trimethoprim, trimetrexate, trinitrate, tripotassium dicitratobismuthate, trofinetide, tropicamide, tropisetron, trospiumchloride, trovafloxacin, troxipide, tucatinib, tulobuterol, tylerdipinehydrochloride, ubenimex, ubidecarenone, ubrogepant, udenafil, ulinastatin, ulipristal, ulixertinib, ulobetasol, umeclidinium, umeclidinium bromide, upamostat, uprosertib, uracil, urapidil, uridinetriacetate, uroacitides, ursodeoxycholic acid, ursolicacid, vaborbactam, vadadustat, valaciclovir, valaciclovir hydrochloride, valbenazine, valdecoxib valganciclovir, valomaciclovir stearate, valproic acid, valrubicin, valsartan, valsartan trisodium hemipentahydrate, vancomycin, vancomycin hydrochloride, vandetanib, vaniprevir, vanoxerine, vapendavir, vardenafil hydrochloride, varenicline, varithena, varlitinib, vatiquinone, vavelta, veliparib, velpatasvir, velusetrag, vemurafenib, venetoclax, venlafaxine, ventafaxine hydrochloride, vepoloxamer, verapamil, verapamil hydrochloride, verdinexor, veregen, vericiguat, verinurad, vernakalant, vernakalant hydrochloride, verosudil, verteporfin, verubecestat, verubulin, vesatolimod, vesnarinone, vibegron, vicagrel, vigabatrin, vilanterol, vilanterol trifenatate, vilaprisan, vilazodone, vildagliptin, vincristine sulfate, vinflunine, vinorelbine, vinpocetine, vintafolide, viralym-C, vismodegib, vistusertib, vitamin E nicotinicate, vizomitin, voglibose, volasertib, volixibat potassium ethanolate hydrate, vonoprazan fumarate, vorapaxar, voriconazole, vorinostat, vortioxetine, vortioxetine hydrobromide, vosaroxin, voxilaprevir, warfarin, xemilofiban, yimitasvir, yonkenafil, zabofloxacin, zafirlukast, zalcitabine, zaleplon, zaltoprofen, zamicastat, zanamivir, zemiStatin, Z-endoxifen hydrochloride, zibotentan, zidebactam, zidovudine, zileuton, zincacetate, zinostatin stimalamer, ziprasidone, zofenopril, zogenix, zoledronate D,L-lysinemonohydrate, zoledronate disodium, zoledronic acid, zoliflodacin, zolmitriptan, zolpidem, zolpidem tartrate, zonisamide, zopiclone, zotepine, zucapsaicin, zuclopenthixol, and zuretinol acetate, including combinations thereof.

In some embodiments, the medicament can be provided in one or more forms that could exhibit diminished efficacy or stability during the formation of a dosage form, particularly if the medicament is exposed to the printing fluid and/or interacts with other components within the bound-powder matrix. In some embodiments, the API compound itself is sensitive to process conditions for constructing the dosage form. In another embodiment, the medicament can be provided in the form of engineered particles made via spray drying, coating, granulation, chemical complexation, co-crystallization, or combinations thereof. In some embodiments, the medicament can be chemically incompatible with one or more excipients comprised within a container body or lidding body. Non-limiting examples of such coatings can include taste-masking agents, as well as controlled-release agents or extended-release agents, which can be utilized to delay dissolution of the medicament until after the disintegrated dosage form is ingested. In some embodiments, the API compound or the medicament as a whole can be sensitive to one or more of moisture, liquid, light, and/or elevated temperature.

Without being limited by a particular theory, sensitivity to one or more process conditions or components within the bound-powder matrix can negatively impact the physical or chemical instability of the medicament; the dissolution, release, or efficacy of the API compound; and/or organoleptic or other physical properties of the dosage form. As a result, the time required to develop dosage forms containing such sensitive materials is often extensive and laborious. However, in another embodiment, the research and development time for dosage forms comprising condition- or process-sensitive API compounds or medicaments can be decreased by dispensing them into pre-formed container bodies, and enclosing them with a pre-formed lidding body, according to any of the methods for forming a dosage form described herein. Use of such pre-formed container bodies and lidding bodies allows for the filling of medicament (and optionally other components) under process conditions that differ from those used to make the container bodies and lidding bodies. This approach can be used to avoid liquid exposure, oven exposure, or other process condition that is undesirable for certain APIs or medicaments. In one non-limiting example, a pre-formed container body and lidding body are used to allow dry filling of medicament in a preferred solid-state form as a co-crystal, thereby avoiding dissolution of the co-crystal and potential subsequent recrystallization as one or more undesired crystal forms or as amorphous material subject to form change. In another non-limiting example, a pre-formed container body and lidding body are used to allow dry filling of an effervescent material incorporating one or more medicaments, thereby avoiding liquid contact that would inadvertently trigger effervescent reaction during processing. In another non-limiting example, a pre-formed container body and lidding body are used to allow dry filling of a coated API or medicament, thereby avoiding liquid exposure and/or oven exposure that may compromise the function of the coating, such coating function including taste-masking, controlled- or modified- or extended-release, physical isolation for chemical stability reasons, or other pharmaceutical purpose as recognized in the art.

In another non-limiting example, a pre-formed container body and lidding body are used to allow dry, ambient temperature filling of an API or medicament provided in the form of an amorphous solid dispersion (ASD), thereby avoiding undesired liquid exposure and/or oven exposure that may compromise the function of the ASD. As is recognized in the relevant art, ASDs may be used to improve bioavailability of compounds with poor aqueous solubility, such as compounds in Class II and/or Class IV of the Biopharmaceutics Classification System (BCS). Generally, ASDs are manufactured by either a solvent-based approach or a fusion-based approach, the objective being to maintain the drug in an amorphous state, retain drug stability characteristics, and create a free-flowing powder that can be easily processed using conventional dosage form manufacturing technologies. In particular, fusion-based approaches can include the thermo-kinetic processing of hot melt extrudates to form multi-particulate formulations which can be tailored to provide such properties as modified release (e.g. extended release, controlled release, and other release profiles), enhanced bioavailability, taste masking, improved solubility, and/or medicament stabilization. Methods and apparatuses for producing multi-particulate formulations with such properties are described, for example, in U.S. Pat. Nos. 9,050,254 and 10,132,565, as well as U.S. Patent Publication Nos. 2011/0014295 and 2021/0038520, the disclosures of which are herein incorporated by reference in their entireties.

In another non-limiting example, a pre-formed container body and lidding body are used to allow dry, ambient temperature filling of an API or medicament provided in the form of a melt extrudate or other engineered particles initially formed via melt extrusion, thereby avoiding undesired liquid exposure and/or additional thermal exposure that may compromise one or more functions of the melt extrudate or other engineered particles initially formed via melt extrusion.

In another non-limiting example, a pre-formed container body and lidding body are used to allow dry, ambient temperature filling of an orally-available protein, peptide, monoclonal antibody, vaccine, or other biologic, thereby avoiding undesired liquid exposure and/or oven exposure that might compromise the physical or chemical stability, or the biological activity, of the protein, peptide, monoclonal antibody, vaccine, or other biologic.

In another embodiment, the medicament can be a chemical compound approved by the FDA or similar governing agency for administering to a subject as part of a clinical trial. In another embodiment, the solid medicament can be a placebo material intended to mimic the taste, texture, and overall experience of a rapidly-orodispersible dosage form containing a medicament, but without having a pharmacologic effect.

In another embodiment, a dissolvable barrier material can be deposited into a cavity prior to depositing the one or more solid medicaments, to inhibit or prevent migration of the one or more medicaments into the bound-powder material comprising the dosage form. As with the powder and binder materials, dissolvable barrier materials can also be ingested and disperse in aqueous solution at a similar rate, or faster rate, compared to the porous bound powder matrix materials comprising the tablet. Non-limiting examples of dissolvable barrier materials can be selected from the group consisting of: mannitol, sorbitol, xylitol, lactitol, erythritol, isomalt, povidone, copovidone, hydroxypropylcellulose, hydroxypropylmethylcellulose, carboxymethylcellulose, gelatin, casein, agar, guar gum, gellan gum, xanthan gum, locust bean gum, alginate, carrageenan, hydroxypropyl starch, pre-gelatinized starch, poloxamer, polyethylene glycol, polydextrose, or polyvinyl alcohol, including derivatives and/or combinations thereof.

In another embodiment, a pre-determined mass of one or more solid, particulate payload material(s), for example, a particulate medicament, can be deposited into and contained within the cavity. A pre-determined amount, by mass or volume, of particulate payload material can be mechanically dosed and/or metered into the depression by any means known in the art, non-limiting examples of which are described in U.S. Pat. Nos. 9,409,699 and 9,828,119, and US Patent Publications 2017/0322068 and 2018/0031410, the disclosures of which are incorporated by reference in their entireties. In another embodiment, the mass of the one or more medicaments contained within the dosage form, whether deposited into the cavity or interspersed within the dosage form's interconnected matrix, can be any one of at least 1 microgram, or at least 1 milligram, or at least 5 milligrams, or at least 10 milligrams, or at least 25 milligrams, or at least 50 milligrams, or at least 75 milligrams, or at least 100 milligrams, or at least 200 milligrams, or at least 250 milligrams, or at least 300 milligrams, or at least 400 milligrams, or at least 500 milligrams, or at least 600 milligrams, or at least 700 milligrams, or at least 800 milligrams, or at least 900 milligrams, or at least 1 gram, or at least 2 grams, or at least 3 grams, or at least 4 grams, or at least 5 grams, or at least 10 grams, and up to 10 grams, or up to 5 grams, or up to 1 gram, or up to 500 milligrams, or up to 250 milligrams, or up to 100 milligrams, up to 10 milligrams. In another embodiment, the mass of the one or more solid medicaments deposited into a cavity or interspersed within the dosage form's interconnected matrix can be in a range between and inclusive of any of the values listed above, including but not limited to: at least 1 microgram and up to 10 grams; or at least 1 milligram and up to 1 gram; or at least 1 milligram and up to 10 milligrams; or at least 10 milligrams and up to 100 milligrams; or at least 100 milligrams and up to 200 milligrams; or at least 100 milligrams and up to 500 milligrams.

Figure 13:
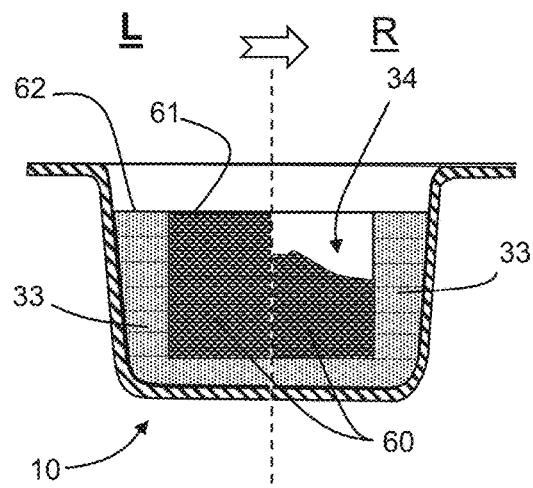
FIG. 13 illustrates a complete filling on the left side, L, and alternatively a partial filling on the right side, R, of the empty cavity of the container, with one or more solid medicaments.
Figure 14:
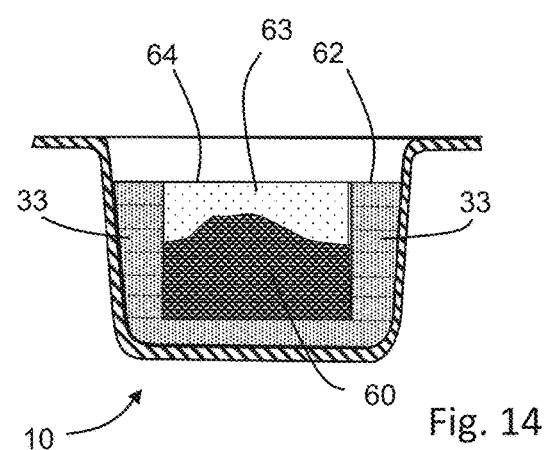
FIG. 14 illustrates the complete filling of the partially-filled cavity shown in the right side of FIG. 13, by depositing one or more filler materials on top of the one or more solid medicaments already inside the cavity.

In another embodiment, which may be used in combination with any one or more of the embodiments described above and herein, the volume of a particulate payload material comprising one or more medicaments dispensed into the cavity of a rapidly-orodispersible container can be sufficient to fill the cavity. As shown in FIG. 13 in the left side of the illustration, the particulate payload material 60 has a top surface 61 that is planar with the upper surface 62 of the peripheral wall 33 to completely fill the cavity 34. In another embodiment, which may be used in combination with any one or more of the embodiments described above and herein, shown in the right side of the illustration of FIG. 13, the volume of the particulate payload material 60 can be sufficient to partially fill the volume of the cavity 34, such that the top surface 61 of the particulate payload material 60 is below the level of the upper surface 62 of the peripheral wall 33. A cavity partially-filled with a particulate payload material 60 can be subsequently filled by dispensing one or more filler materials 63 on top of the particulate payload material 60, until the top surface 64 of the filler material 63 is substantially planar with the upper surface 62 of the peripheral wall 33, as shown in FIG. 14. In another embodiment, the one or more filler materials can be an unbound form of the powder material used to form the bound-powder matrix. In another embodiment, the one or more filler materials can be added to provide a physical and/or chemical barrier between the medicament and the external environment outside of the dosage form, prior to closing off the cavity within an interior portion of the completed dosage form. According to the present invention, the one or more filler materials can be selected from the group consisting of calcium carbonate, calcium lactate, calcium phosphate, calcium silicate, calcium sulfate, cellulose, dextrose, erythritol, isomalt, lactitol, lactose, magnesium carbonate, magnesium oxide, maltodextrin, maltose, mannitol, microcrystalline cellulose, polyethylene glycol, sodium bicarbonate, sodium carbonate, sodium chloride, sorbitol, starch, sucrose, talc, trehalose, and xylitol, and combinations thereof. In a non-limiting example, a bulk powder material and/or a filler material can consist of 90% (w/w) calcium carbonate and 10% (w/w) povidone.

In another embodiment, the filler material can be a super disintegrant. As used herein, a "superdisintegrant" is a material or composition which can be comprised within a dosage form to enhance its orodispersibility upon contacting a liquid, such as saliva or water. Without being limited by a particular theory, it is believed that superdisintegrant materials swell in the presence of water. When a superdisintegrant situated within an interior cavity is exposed to the liquid upon the partial disintegration of the dosage form, the swelling of the super disintegrant can create an internal pressure within the cavity and accelerate the disintegration of the remaining portions of the dosage form. Non-limiting examples of superdisintegrants include carboxymethylcellulose sodium, croscarmellose sodium, sodium starch glycolate, and crospovidone. A superdisintegrant comprised within a filler material can be selected from the group consisting of any of the superdisintegrants listed above, including combinations thereof.

In another embodiment, a rapidly-orodispersible dosage form can be constructed from any of the containers described above, by covering the upper surface of the container and the one or more medicaments, excipients, dissolvable barrier materials, and/or filler materials contained within the one or more cavities. Each of the cavities becomes isolated within the interior portion of the dosage form, both from other cavities and from the environment outside of the dosage form.

Figure 15:
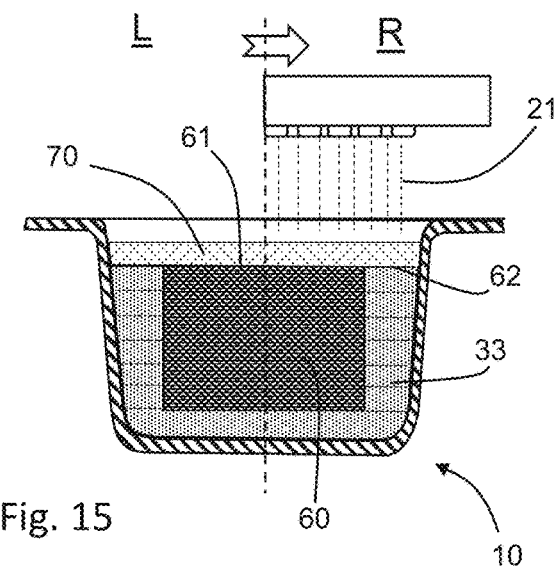
FIG. 15 illustrates on the left side, L, the formation of an upper substantially-uniform layer of powder material on top of the cavity-filling medicament, and on the right side, R, the application of a printing liquid onto the upper substantially-uniform layer of powder.

In a non-limiting example, and in another embodiment, an upper layer of powder material 70 having a substantially-uniform thickness can be formed upon the coplanar surface formed by the upper surface 62 of the peripheral wall 33 and the top surface 61 of particulate payload material 60, as shown in the left side of the illustration of FIG. 15. As shown in the right side of the illustration of FIG. 15, droplets 21 of a printing liquid can be applied to the upper layer of powder material 70, in a pattern and volume to form a dosage form having a bound-powder upper layer 72 atop the cavity filled with particulate payload material 60; forming a unitary dosage form 80 within the depression 10 as shown in FIG. 16. The steps of forming an upper layer of powder material and dispensing a printing liquid atop the cavity can optionally be performed one or more additional times, in forming the unitary dosage form 80.

Partially-Enclosed Dosage Forms

In an embodiment of the invention, a unitary, partially-enclosed dosage form is provided, having an internal cavity, and having a port opening within and through the container body (for example, through the base or the peripheral wall) or a lid portion that encloses the container body. The port opening is in fluid communication with the one or more cavities formed within the container body. The port opening is typically a portion of the lid or the container body where the particulate powder material was left unbound (for example, unprinted with printing liquid) during the forming of the bounder powder matrix of the lid or container body. Once the lid and container body have been formed, any unbound powder material contained within the interior cavity(ies) of the container body can be evacuated through the port opening.

A port opening can be of any formable shape, although circular or oval shapes preferred. The cross-sectional size of the port opening is typically sufficient in effective size or diameter to evacuate the unbound powder material from the interior cavity by fluidizing or pouring the unbound powder material out through the port opening, and sufficient to permit filling the evacuated interior cavity with a payload material. After a payload material is placed within the interior cavity, along with any optional filler material, the port opening can be closed and sealed as discussed herein. The effective size or diameter of the port opening can be as minimal in size or diameter as possible to simplify or improve the subsequent closing and/or sealing of the port opening, once most or all of the unbound powder material has been evacuated, and the payload material deposited into the internal cavity of the dosage form.

Figure 17:
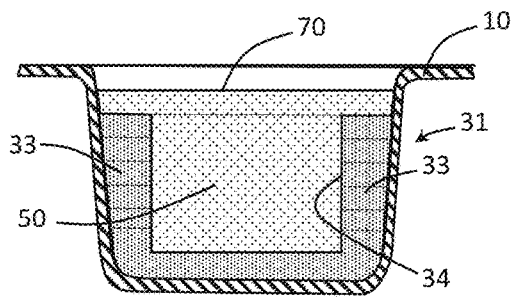
FIGS. 17-21 illustrate forming, filling and sealing a unitary, partially-enclosed dosage form having an internal cavity, formed within a depression of a packaging.
Figure 18:
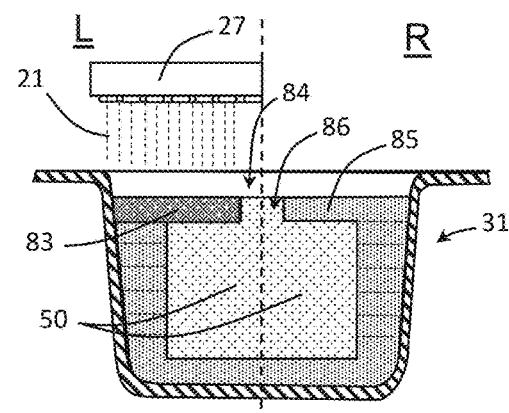

FIG. 17 shows a sectional view of the container body 31 formed within a depression 10, as shown in FIG. 6, having a cavity 34 filled with unbound build powder material 50, and upon which one (or more) incremental upper layer 70 of build powder material is formed having a substantially uniform thickness. As shown in the left side of FIG. 18, a printing liquid 21 is deposited onto preselected portions of the incremental upper layer 70 of build powder material, though avoiding the depositing of the printing liquid is an area 84, forming a printed or wetted layer 83 that surrounds the unprinted area 84. In the right side of FIG. 18, wetted layer 83 forms the bound powder matrix of a lid 85 for the container body, having an area of unbound powder material to form a port opening 86, typically located proximate at or near the center of the lid 85.

In most circumstances, the effective opening size or diameter of the port opening is typically from about 1 millimeter (mm), and up to about 5 mm, and may be about 2 mm to 4 mm, about 2 mm to 3 mm, about 3 mm to 4 mm, and about 4 mm to 5 mm. The relative effective size or diameter of a port opening formed into a lid of a dosage form, or a base of a container body, is less than 50%, more typically less than 25%, and even more typically less than 15%, the effective size or diameter of the lid or base of the container.

Figure 19:
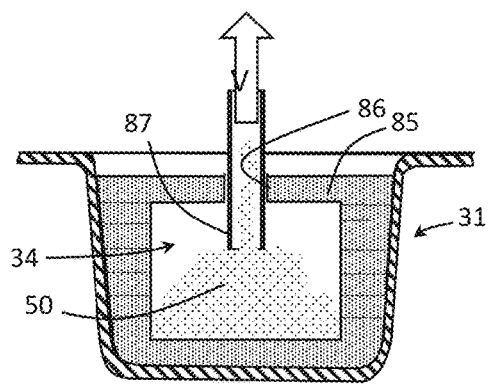

The resulting unitary, partially-enclosed dosage form comprises the container body 31 having an internal cavity 34 filled with unbound build powder material 50, covered with a unitary lid 85 of bound powder matrix material and having the port opening 86. FIG. 19 shows an evacuation system V for evacuating or removing the unbound build powder material 50 from within the cavity 34, through the port opening 86 in the lid 85. In the illustrated embodiment, the evacuation system is illustrated as a vacuum system which draws air and the fluidizing unbound build powder material 50 from within the cavity 34. A distal tip of a tube 87 connected to the vacuum system V can be inserted into port opening 86 in the lid 85 to assist in evacuating most or all of the unbound build powder material 50, to leave an empty or substantially empty cavity 34. The inlet opening in the tube 87 should be larger than the largest particle size of the particulate build powder material.

Figure 20:
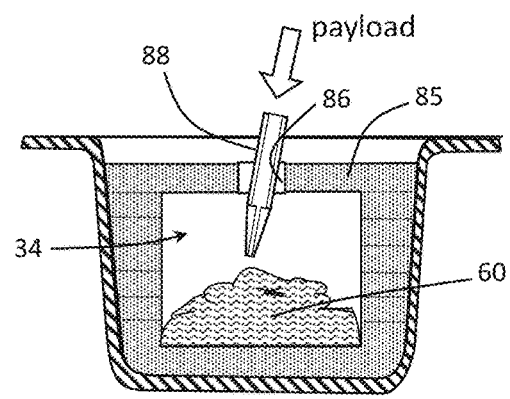

After most or all of the unbound build powder material 50 is evacuated from the cavity 34, a payload material 60 can be deposited into the evacuated cavity. FIG. 20 shows a means for partially or completely filling the empty cavity 34 through the port opening in the lid, with a payload material 60. The payload material can be deposited into the cavity 34 by any well-known means, such as a pipette 88 as illustrated, or an injection needle, which can be inserted through the port opening 86 and into the cavity 34 to avoid spillage or loss of the payload material. The payload material can be any of the solid, particulate, liquid, semi-solid or engineered particles and materials described herein. In some embodiments, after the payload material 60 has been deposited into the cavity, a filler material that is typically inert with the payload material, can be deposited to fill the remaining volume of the cavity 34. In some embodiments, only a small portion of the unbound build powder material 50 can be withdrawn from the cavity 34, as shown in FIG. 20, the small portion by volume being sufficient to provide space for a small amount or volume of a payload material 60.

Figure 21:
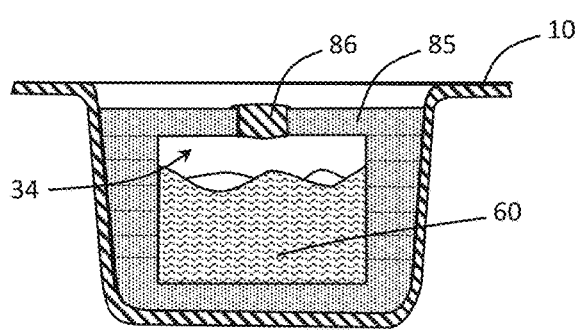

After the payload is deposited into the cavity of the partially-enclosed dosage form, the port opening 86 in the lid 85 can be closed and sealed to prevent the payload and any remaining unbound build powder material from escaping. FIG. 21 shows a plug 89 filling and sealing the port opening 86. The sealing material of the plug 89 can be a solid or solidifying material, and preferable a water-soluble and ingestible material. A preferred material is a solid or waxy material at normal room or storage temperatures, and meltable at elevated temperatures to flow into and seal the edges of the port opening 86. Non-limiting examples of a sealing material are fats, water-soluble polymers, polyethylene glycol, carbohydrates and carbohydrate alcohols, including any one or more thermal binding materials as described herein.

Separate Container and Lid

In another embodiment, rather than printing one or more bound-powder upper layers to form a container body with a lid as a single, contiguous matrix, a container 31 can be formed and then filled with a payload material 60 and optionally filler material 63, and a separately-formed rapidly-orodispersible lid can be placed and secured upon the upper surface of a rapidly-orodispersible container 31. Processes for forming a rapidly-orodispersible tablet from separately-formed container- and lidding bodies are described herein.

Forming a lidding body separately from the container body can be advantageous because it enables the rapidly-orodispersible tablet to be conveniently constructed and handled within different areas of the same facility, or between multiple facilities, without having to form the entire tablet at one place or facility, or at the same time. In a non-limiting example, a set of container bodies and lidding bodies can be formed separately in a first facility and subsequently packaged as a kit and shipped to a second facility. At the second facility, one or more payloads can be dispensed into the interior cavity of the container body, and the lidding body can be secured to the container body, to form the rapidly-orodispersible tablet. In a further embodiment, the formed container and lidding bodies can be stored for a period of time selected from the group consisting of hours, days, weeks, months, or years, prior to dispensing the one or more payloads into an internal cavity and securing the container body and lidding body together to form a tablet.

In a non-limiting example, a kit consisting of a container body and a lidding body can be provided to a point-of-care facility, such as a hospital, clinic, nursing home, or pharmacy. In some embodiments, the container body can be filled with a payload, particularly payloads comprising one or more medicaments, immediately upon the container body, lidding body, and payload arriving at the point-of-care facility. In other embodiments, the container body and/or lidding body can be stored at the point-of-care facility for a length of time, until a particular rapidly-orodispersible tablet is required or prescribed.

In another embodiment, the lidding body can be formed to have a complementary shape and size relative to the upper surface and/or the interior cavity of the container body. In another embodiment, the lidding body can be formed to completely cover the interior cavity when it is secured to the container body, preventing the accidental or incidental release of the solid medicament from the rapidly-orodispersible tablet and potential damage from the tablet's external environment. In a further embodiment, the lidding body can be formed so it also covers the upper surface of the container body. As a non-limiting example, and in another embodiment, a lidding body can be formed so it has the same diameter as the upper surface of a cylindrical container body, to form a cylindrical rapidly-orodispersible tablet. In another embodiment, the lidding body can be formed so it extends beyond the upper surface of the container body. In another embodiment, the lidding body can be formed so it extends beyond the upper surface of the container body and along one or the external surface of the container body peripheral wall. Non-limiting examples of such lidding bodies, and their complementary shapes relative to the container body are described in further detail, below.

In another embodiment, the lidding body can be formed to have any desired height relative to the height of the container body. In another embodiment, the lidding body can be formed to have a height that is equal or less to the height of the container body. In another embodiment, the ratio of the height of the lidding body relative to the container body can be selected from the group consisting of: less than 1:1; less than 0.95:1; less than 0.9:1; less than 0.85:1; less than 0.8:1; less than 0.75:1; less than 0.7:1; less than 0.65:1; less than 0.6:1; less than 0.55:1, less than 0.5:1; less than 0.45:1, less than 0.4:1; less than 0.35:1, less than 0.3:1; less than 0.25:1; less than 0.2:1; less than 0.15:1; and less than 0.1:1. In another embodiment, the lidding body can be formed to have a height that is equal or greater than the height of the container body. In another embodiment, the ratio of the height of the lidding body relative to the container body can be selected from the group consisting of: greater than 1:1; greater than 1.05:1; greater than 1.1:1; greater than 1.15:1; greater than 1.2:1; greater than 1.25:1; greater than 1.3:1; greater than 1.35:1; greater than 1.4:1; greater than 1.45:1; greater than 1.5:1; greater than 1.55:1; greater than 1.6:1; greater than 1.65:1; greater than 1.7:1; greater than 1.75:1; greater than 1.8:1; greater than 1.85:1; greater than 1.9:1; greater than 1.95:1; and greater than 2:1. Non-limiting examples of the such lidding bodies, and their complementary sizes relative to the container body are described in further detail, below.

In another embodiment, the lidding body can have a planar undersurface formed to have the same size and geometric shape as the planar upper surface of the container body peripheral wall. The selection of such geometric shapes is generally described above. Several non-limiting examples of lidding bodies formed to have a planar undersurface having a complementary size and shape relative to a planar upper surface of a corresponding container body are illustrated in FIGS. 22 and 23, 24 and 25, and 26 and 27, including lidding bodies with circular, elliptical, and rectangular undersurfaces that can be secured to container bodies having corresponding circular, elliptical, and rectangular upper surfaces, respectively. FIGS. 22 and 23 show exploded and perspective views of a spherocylindrical dosage form 130A assembled from a lidding body 131A with a circular undersurface 132A and a container body 133A with a circular upper surface 134A. FIGS. 24 and 25 show exploded and perspective views, respectively, of an ovoid dosage form 130B assembled from a lidding body 131B with an elliptical undersurface 132B and a container body 133B with an elliptical upper surface 134B. FIGS. 26 and 27 show exploded and perspective views, respectively, of a dosage form 130C with a cuboid shape, assembled from a lidding body 131C with a rectangular undersurface 132C and a container body 133C with a rectangular upper surface 134C. In other embodiments, any of the lidding bodies 131A or 131B illustrated in FIGS. 22-25 and having an internal cavity can optionally be constructed to have a solid interior portion, similar to lidding body 131C in FIGS. 26 and 27.

In another embodiment, the lidding body can be secured to the container body by one or a combination of securing, including one or more of an adhesive material applied to one or both of the lidding body and the container body, a mechanical securement formed into or associated with one or both of the lidding body and the container body, and a frictional engagement between the lidding body and the container body, including combinations thereof. By any means, and in another embodiment, once the lidding body and the container body are secured together, the resulting dosage form can have the ability to withstand shearing, twisting, and/or impact forces that may cause the lidding body and the container body to inadvertently or incidentally separate from each other prior to being administered to a user.

In another embodiment, the lidding body and the container body can be secured together adhesively, with an adhesive material disposed at the confronting and contacting surfaces of the lidding body and the container body. Generally, a suitable adhesive material can have the strength to withstand any of the forces described above, while at the same time being non-toxic to a user who is ingesting the rapidly-orodispersible dosage form. In another embodiment, such adhesive material can be selected from the group consisting of mannitol, sorbitol, xylitol, lactitol, erythritol, isomalt, povidone, polyvinylpyrrolidone (PVP, copovidone), hydroxypropylcellulose, hydroxypropylmethylcellulose, carboxymethylcellulose, gelatin, casein, agar, guar gum, gellan gum, xanthan gum, locust bean gum, alginate, carrageenan, hydroxypropyl starch, pre-gelatinized starch, poloxamer, polyethylene glycol, polydextrose, or polyvinyl alcohol, including derivatives thereof and/pr combinations thereof.

In a further embodiment, the adhesive material can be a material that becomes an adhesive upon being heated or thermally activated to a temperature above at least the softening point of the material, and optionally being heated at or above the melting point of the material. The adhesive material can be conductively heated by placing a heating element, such as a temperature-controlled soldering iron, in direct contact with the juncture of the lidding body and/or container body, proximate their confronting and contacting surfaces. In another embodiment, the adhesive material can be radiantly heated by directing radiant heat, such as infrared or laser light, at the juncture of the lidding body and/or container body, proximate their confronting and contacting surfaces.

Non-limited examples of adhesive materials that can be thermally-activated are mannitol, sorbitol, xylitol, lactitol, erythritol, isomalt, povidone, copovidone, hydroxypropylcellulose, poloxamer, polyethylene glycol, and polyvinyl alcohol. In a non-limiting example, a thermally-activatable adhesive material, such as mannitol, can be individually comprised within the interconnected matrix of the container body and/or the lidding body, wherein a rapidly-orodispersible tablet can be formed by applying heat to one or more points of contact between the lidding body and container body, sealing them together.

In a non-limiting example, adhesive material can be a component particulate compound or composition contained within the build powder material, and in some embodiments, the adhesive material can also be a binder material contained within the build powder material, including any of the compounds identified as a binder material herein. One non-limiting example of an adhesive material contained in the build powder is mannitol. The bound powder matrices of both the container body and the lidding body can contain particles of the binder material distributed throughout the matrices. By applying heat (conductively, convectively, or radiantly) to one or more junction points where the surfaces of the lidding body confront and contact the container body, a portion of the binder material disposed at the contacting surfaces of the bound powder matrix of either (or both) the lidding body and the container body can soften or melt and flow into mutual contact with both surfaces, adhering the two surfaces together at the one or more junction points. In other embodiments, applying heat (conductively, convectively, or radiantly) continuously along the confronting surfaces of the container body and the lidding body can form a continuous bonded and sealed interface between the two body surfaces.

Figure 28:
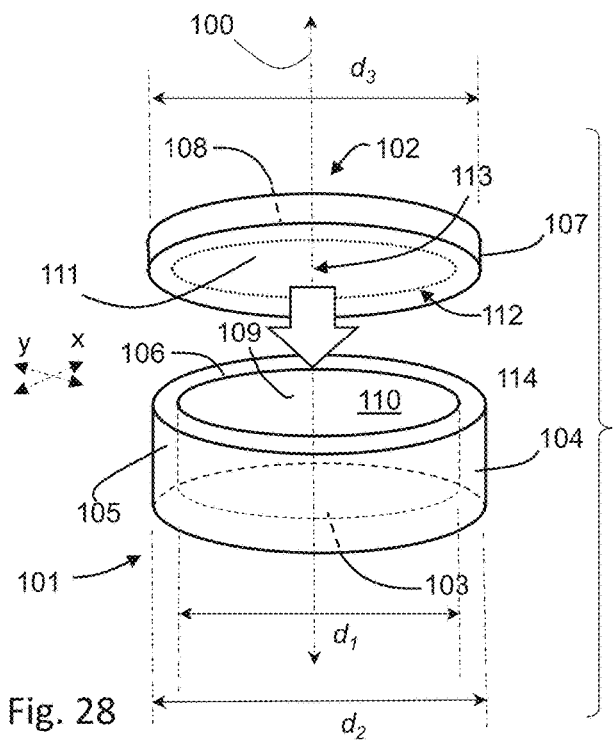
FIG. 28 shows an exploded perspective view of a cylindrical, two-piece dosage form having a container body and an upper lidding body.

In a first non-limiting example shown in FIG. 28, a dosage form can be formed by securing a cylindrical container body 101 with a cylindrical lidding body 102. The container body 101 has a circular base 103, and a peripheral wall 104 having an inner diameter $d_1$ and an outer diameter $d_2$. The peripheral wall 104 extends from the periphery of the base 103 and has an external surface 105 and an upper surface 106. The lidding body 102 has a perimeter edge 107 and a circular undersurface 111 that has a diameter, $d_3$, that is the same or greater than the outer diameter $d_2$ of the container 101. As illustrated, the circular undersurface 111 of the lidding body 102 and the circular container base 103 are parallel with each other. A peripheral portion 112 of the lidding body 102 contacts the upper surface 106 of the peripheral wall 104, and an internal portion 113 covers the cavity 110. The cavity, though shown to be empty for clarity, can advantageously be either partially- or completely filled with one or more particulate payload materials, including the medicament(s), at the time the lidding body is applied and secured to the container body. Unitary tablet forms, as described above, generally require an upper layer of powder material to be applied atop a planar surface formed by both the upper surface of the container peripheral wall as well as the particulate payload material(s) inside the cavity, in order for the upper layer to have a substantially uniform thickness. In contrast, and as described below, the peripheral portion of the lidding body undersurface can be secured solely to the container body peripheral wall, without also having to secure the internal portion of the lidding body undersurface. Consequently, a single dosage form with a standardized set of dimensions and properties can be utilized to contain any desired dose amount or volume of medicament(s) inside the cavity, including and up to the volume of the cavity itself.

In another embodiment, an adhesive material can be applied onto any surface of the container body, the lidding body, or both, that forms a contact surface in the assembled dosage form. Using the dosage form of FIG. 28 as a non-limiting example, an adhesive material can be applied to either or both of the peripheral portion 112 of the lidding body undersurface 111 and the upper surface 106 of the container body peripheral wall 104, including selected portions thereof. In an embodiment, the adhesive material can be applied and distributed across the entire contact surface between the lidding body and the container body, or it can be applied so it is localized to selected multiple portions or areas of the contact surface. Those skilled in the art can determine the identity and location of the applied adhesive material based on several factors, including but not limited to the desired hardness, orodispersibility, and stability of the dosage form. In an alternative embodiment, when the particulate payload material(s) within the container body completely fills the volume of the interior cavity and has a top surface that is planar with the upper surface of the container body peripheral wall, the adhesive material can also be applied to the top surface 110 of the particulate payload material and/or the interior portion of the lidding body undersurface. In embodiments in which the adhesive material is applied to the solid medicament directly, the adhesive material can be selected so that is inert relative to the solid medicament and does not affect its stability and/or pharmaceutical activity.

In another embodiment, the lidding body and/or the container body can be constructed to have one or more structural features that increase the surface area of the contact surface between the lidding body and the container body. In an embodiment shown in FIG. 29, a lidding body 120 can be formed to have a projection portion 121 that extends from the undersurface 111. The projection portion 121 has an annular sidewall surface 122 having a height, h, and a bottom surface 123 having a diameter, $d_3'$. In another embodiment, the annular outer surface 122 can have any height sufficient to secure the lidding body 120, while providing space sufficient within the cavity 110 for the particulate payload material. Upon placing the lidding body 120 onto the upper surface 106 of the peripheral wall 104, the projection portion 121 extends into the cavity 110 of the assembled dosage form 125, forming an additional contact surface between the lidding body 120 and the container body 101. In an embodiment, the bottom surface 123 of the secured projection portion 121 contacts the particulate payload material inside the interior cavity 110, while in another embodiment, the bottom surface 123 of the secured projection portion 121 does not contact the particulate payload material inside the interior cavity 110.

In another embodiment, the diameter, $d_3'$, of the projection portion 121 can be configured to be identical to, or only very slightly larger than, the diameter, $d_1$, of the interior cavity 110 of the container body 101, to allow the outer sidewall surface 122 of the projection portion 121 to frictionally engage with the inner surface 109 of the upper end of the peripheral wall 104.

In an alternate embodiment, the diameter, $d_3$, of the projection portion 121 can be configured to be slightly smaller than the diameter, $d_1$, of the interior cavity, but large enough for the annular outer surface 122 and the inner surface 109 of the peripheral wall 104 to adhere to each other upon the application of an adhesive material. In a further embodiment, an adhesive material can also be applied to the peripheral undersurface 112 of the lidding body and/or the upper surface 106 of the peripheral wall 104.

In various embodiments, the lidding body and the container body can have mating or congruent mechanical features that mechanically or physically engage one another, which prevent movement of the lidding body in at least one direction relative to the container body, other than the lidding body being seated on the container body to close the cavity of the container body when assembled. As used herein, the terms, "mechanically engaged" or "physically engaged" mean that a surface or edge of one body is in direct or near contact with a surface or edge of the other body to prevent movement in at least one direction. The engagement of the mating mechanical features can prevent the lidding body from moving relative to and/or separating away from the container body when assembled in one or more of three directions: an axial direction, illustrated by axial line 100 in FIG. 28, where the lidding body can lift upward from the container body; one or more lateral direction, illustrated as a movement in the x-y plane shown in FIG. 28, where the lidding body can slide laterally away, transverse to the axial line 100, in one or more angular directions; and a rotational direction, illustrated as angular rotation c about the axial line 100 in FIG. 28, where the lidding body can rotate about the axial line 100.

Figure 29:
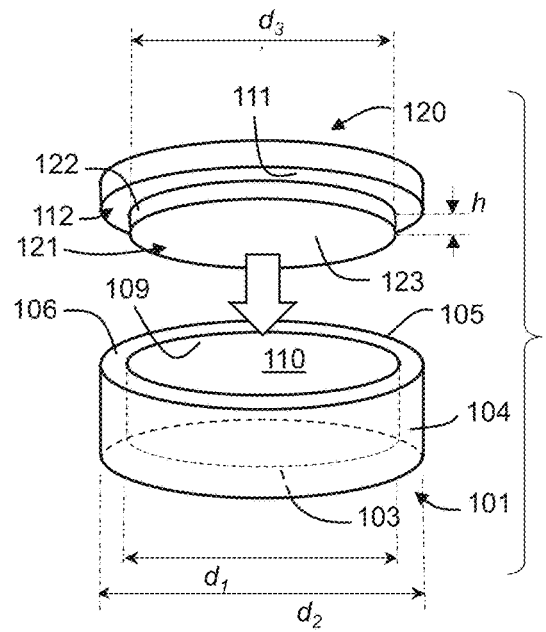
FIG. 29 shows an exploded perspective view of another cylindrical, two-piece dosage form, in which the lidding body has an interior projection portion extending from the undersurface of the upper lidding body.

As a non-limiting example, the lidding body 120 shown in FIG. 29 has a projection portion 121 that, when assembled, extends from the undersurface 111 partially into the cavity 110 of the container body 101, thereby providing a mechanical or physical engagement that prevents a lateral movement of the lidding body relative to the container body in all lateral directions in the x-y plane. By comparison, in the lidding bodies and container bodies illustrated in FIGS. 22-28, once the lidding body is seated over and assembled with the container body to close the cavity of the container body, the lidding body can be moved in any of the three directions to separate from the container body: the axial direction upward, any lateral direction, and the rotational direction. In such embodiments, the lidding body and the container body are secured or affixed together by some adhesive or unitary mechanism. The fitment of the peripheral edge of the projection portions 121 of the lidding body 120 with inner surface 109 of the upper end of the peripheral wall 104 of the container body 101 maintains the lidding body 120 engaged with the container body 101 during subsequent handling, packaging and use of the article.

Generally, a mating or congruent mechanical securement can comprise a first mechanical element that mates or congruently engages a second one or more mechanical elements. A non-limiting example of a first mechanical element can be selected from the group consisting of a tab, ridge, peak, pin, knob, or similar or equivalent extension feature, and a non-limiting example of a second mechanical element can be selected from the group consisting of a valley, notch, cut, slot, thread, or similar or equivalent receiving feature. Processes for forming such mechanical elements as a feature into a bound powder matrix, including using 3DP, are well known in the art. In another embodiment, one or more first mechanical elements can be formed into the lidding body, while one or more second mechanical elements can be formed into the container body. In another embodiment, the one or more first mechanical elements can be formed into the container body, while the one or more second mechanical elements can be formed into the lidding body. In another embodiment, a lidding body and a container body within the same tablet can each contain first and second mechanical elements.

In a non-limiting example, and in another embodiment, a plurality of peaks can be formed into the upper surface of the container body peripheral wall, which can mate with a plurality of valleys formed into the undersurface of the lidding body. In an alternate embodiment, a plurality of peaks can be formed into the undersurface of the lidding body, which can mate with a plurality of valleys formed into the upper surface of the container body peripheral wall. In either arrangement, the peaks on the lidding body can be formed to have complementary structures relative to spaces between peaks on the container body, such that when lidding body properly aligned and placed atop the container body, the number and overall surface area of the contact surfaces between the container body and the lidding body can be increased. An adhesive material can be applied to one or more of these additional surfaces to provide a more secure fit between the container body and lidding body.

Figure 30:
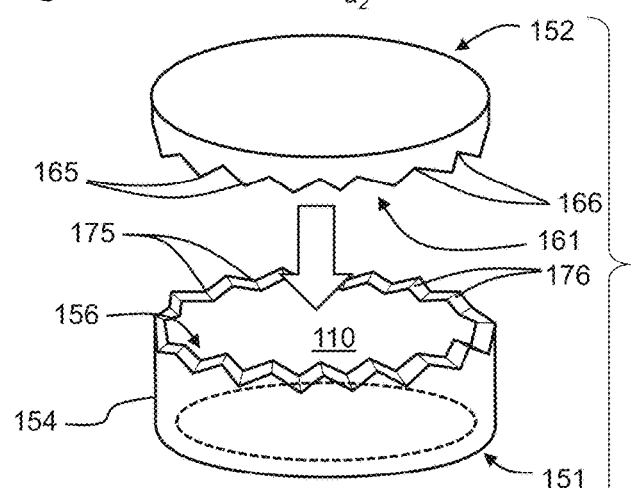
FIG. 30 shows a perspective view of an alternate embodiment of a dosage form having a plurality of peaks extending from the undersurface of the lidding body and a plurality of complementary valleys formed into the upper surface of the container body.
Figure 31:
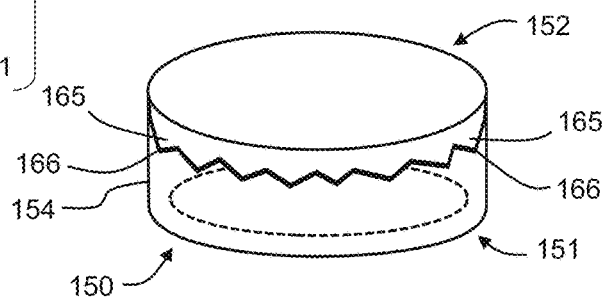
FIG. 31 shows a perspective view of a dosage form assembled by securing the lidding body and container body of FIG. 29.

As shown in FIG. 30, an undersurface 161 of lidding body 152 can include a plurality of lid peaks 165 separated by lid valleys 166, which can mate with a correspondingly-shaped plurality of container peaks 175 and container valleys 176, respectively, having a complementarily-shaped structure, and formed into the upper surface 156 of the peripheral wall 154 of container body 151. Securing lidding body 152 and container body 151 forms dosage form 150, illustrated in FIG. 31. In various embodiments, each of the peaks 165,175 can have an identical size relative to each other, though in alternative embodiments, one or more of the peaks 165,175 can be larger, smaller, or have different shapes relative to other peaks 165,175, so long as there are a corresponding number of valleys 176,166 on the container body and lidding body, respectively, with complementary size(s) and shape(s) to receive them. Without being limited by a particular theory, providing a repeating series of uniformly sized and/or shaped peaks 165,175 and valleys 166,176 can provide a precise fit that ensures that the lidding body 152 is placed onto the container body 151 properly in any orientation of the lidding body 152 with the container body 151 each time a dosage form 150 is assembled. In another embodiment, an adhesive material can be applied to one or more of the peaks and/or valleys, in in addition to any one or more of the contact surfaces described above.

Figure 32:
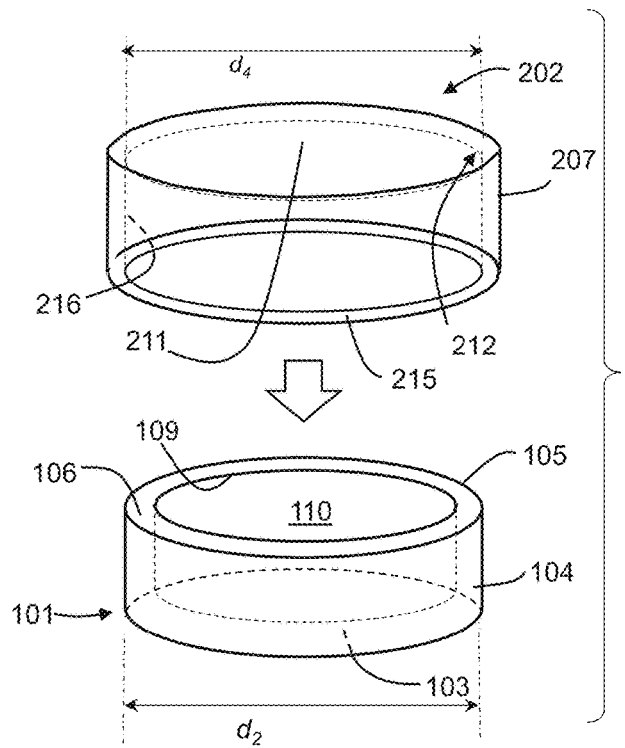
FIG. 32 shows an exploded perspective view of an alternate embodiment of a lidding body and a container body, the lidding body having a perimeter wall extending from a peripheral portion of the lidding body undersurface and radially beyond the perimeter wall of the container body.
Figure 33:
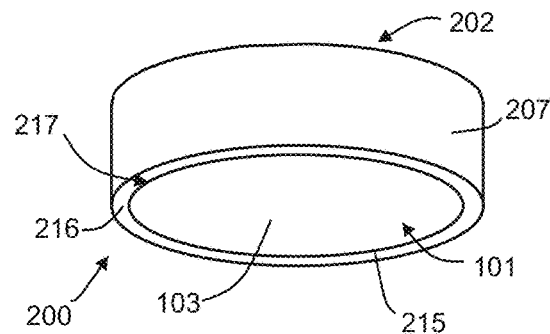
FIG. 33 shows a perspective view of a dosage form assembled by placing the lidding body of FIG. 32 over the container body.

In another embodiment, the lidding body can also be formed in the shape of a container, configured to be inverted and placed over a container body 101, creating a dosage form 200 in which the lidding body envelops the upper surface 106 of the container body 101 and extends along at least a portion of the external surface 105 of the peripheral wall 104. As shown in FIG. 32, the lidding body 202 has a perimeter wall 207 that extends from the peripheral portion 212 of the lidding body undersurface 211, and having a bottom edge surface 215 and an inner surface 216. The inner surface 216 is formed to define a diameter $d_4$ of the lidding body undersurface 211 that can be identical to, or only very slightly smaller than, the diameter, $d_2$, of the container base 103, to allow the inner surface 216 of the perimeter wall 207 to frictionally engage with the external surface 105 of the peripheral wall 104. In an embodiment, the perimeter wall 207 can be configured so its inner surface 216 can engage with the entire external surface 105 of the peripheral wall 104, and form a planar bottom surface 217 of the dosage form 200 with the container base 103, shown in FIG. 33. In an alternate embodiment, the diameter $d_4$ of the lidding body undersurface 211 can be configured to be slightly larger than the diameter $d_2$ of the container base 103, but small enough for the inner surface 216 of the peripheral wall 207 to adhere to the external surface 105 of the peripheral wall 104 upon the application of an adhesive material to either the inner surface of 216 the perimeter wall 207, the external surface 105 of the peripheral wall 104, or both.

Figure 34:
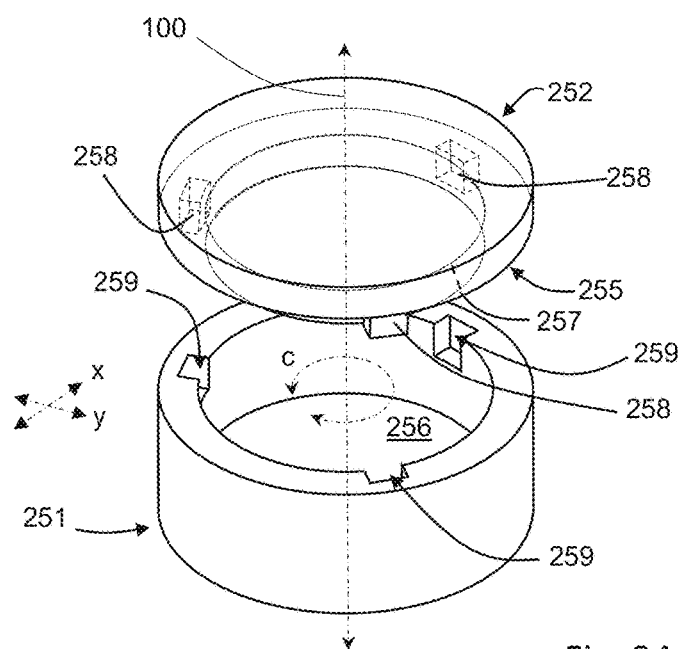
FIG. 34 shows an exploded perspective view of an alternate embodiment of a lidding body and a container body, the lidding body having a trio of pins extending from an undersurface of the lidding body, to engage a corresponding trio of slots in the peripheral wall of the container body.

FIG. 34 shows an embodiment of a lidding body 252 having a trio of pins 258 extending from an undersurface 255 of the lidding body 252, to engage a corresponding trio of slots 259 in the peripheral wall 254 of the container body 251. The lidding body 252 also includes an internal projection 257 that extends partially into the cavity 256 of the container body 251. The pins 258 engagement with the slots 259 prevent both angular rotation and lateral movement of the lidding body 252 relative to the container body 251. The fitment of the side edges of the pins 258 with the inner surfaces of the slots 259 maintains the lidding body 252 engaged with the container body 251 during subsequent handling, packaging and use of the article.

Figure 35:
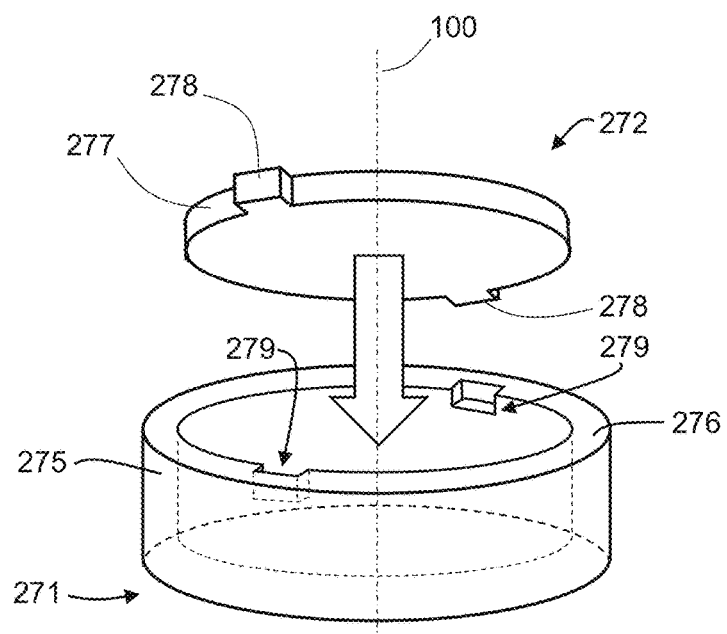
FIG. 35 shows an exploded perspective view of another alternate embodiment of a lidding body and a container body, the lidding body having a pair of opposed pins extending from an outer peripheral surface of the lidding body, to engage a correspondingly-shaped pair of slots in the upper surface of the peripheral wall of the container body.
Figure 36:
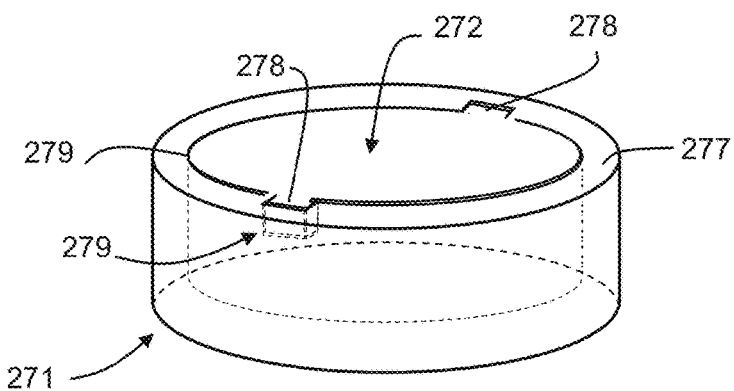
FIG. 36 shows a perspective view of a dosage form assembled by placing the lidding body of FIG. 35 over the container body.

FIG. 35 shows another embodiment of a lidding body 272 having a pair of rectangularly-shaped pins 278 extending from opposite sides of an outer surface of the peripheral edge 277 of the lidding body 272, to engage with and fit down within a pair of congruently-shaped slots 279 formed into opposite sides of the upper surface 276 of the peripheral wall 274 of the container body 251. The pins 278 engagement with the slots 279, as shown in FIG. 36, prevent angular rotation and inward axial movement of the lidding body 272 relative to the container body 271, while the outer surface of the peripheral edge 277 of the lidding body 272 in engagement with the inner surface of the peripheral wall 275 of the container body prevents lateral movement of the lidding body 272 relative to the container body 271. The fitment of the side edges of the pins 278 with the inner surfaces of the slots 279 maintains the lidding body 272 engaged with the container body 271 during subsequent handling, packaging and use of the article.

Figure 37:
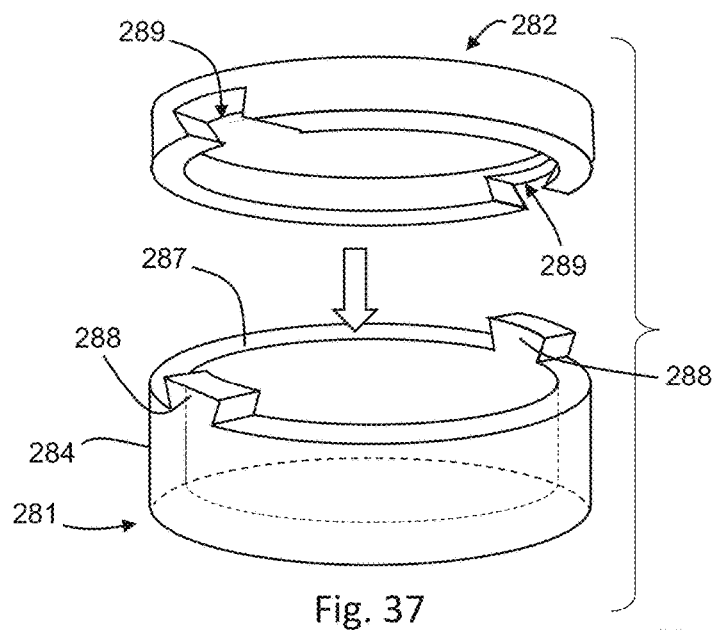
FIG. 37 shows an exploded perspective view of an alternate embodiment of a lidding body and a container body, the lidding body having a pair of keystone slots in a perimeter wall of the lidding body, to engage a pair of keystone pins atop the peripheral wall of the container body.
Figure 38:
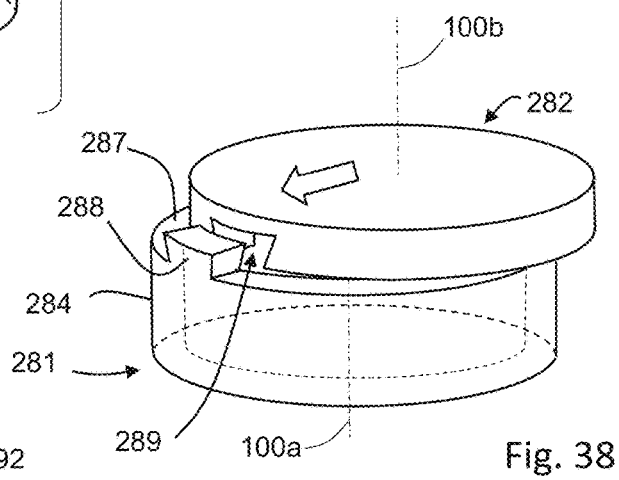
FIG. 38 shows the lidding body being assembled to the container body on FIG. 37 by engaging the keystone pins in the container body into the keystone slots in the lidding body.

FIG. 37 shows an embodiment of a lidding body 282 having a pair of diametrically-opposed keystone-shaped slots 289 in the extending peripheral wall 284, and a container body 281 having a pair of diametrically-opposed keystone-shaped pins 288 extending from the upper surface 287 of the peripheral wall 284 of the container body 281. The pins 288 are of a congruent shape and dimension of the slots 289, though typically slightly shorter lengths and dimensions to allow the pair of pins 288 to slide laterally into the pair of slots 289. FIG. 38 shows the lidding body 282 being assembled to the container body 281 by first aligning the lidding body 282 axially offset from the container body 281, so that the pins 288 align laterally from the slots 289, and then engaging the keystone pins 288 in the container body 281 into the keystone slots 289 in the lidding body 282. Subsequently, the lidding body 282 is moved laterally so that the two pins 288 simultaneously slide into the corresponding slots 289. In this embodiment, the engaged lidding body 282 is prevented from moving relative to the container body 281 in the axial direction, rotatively, and in any other lateral direction than the sliding direction. The fitment of the inside surfaces of the keystone-shaped slots 289 with the outside surfaces of the keystone-shaped pins 288 maintains the lidding body 282 engaged with the container body 281 during subsequent handling, packaging and use of the article.

Figure 39:
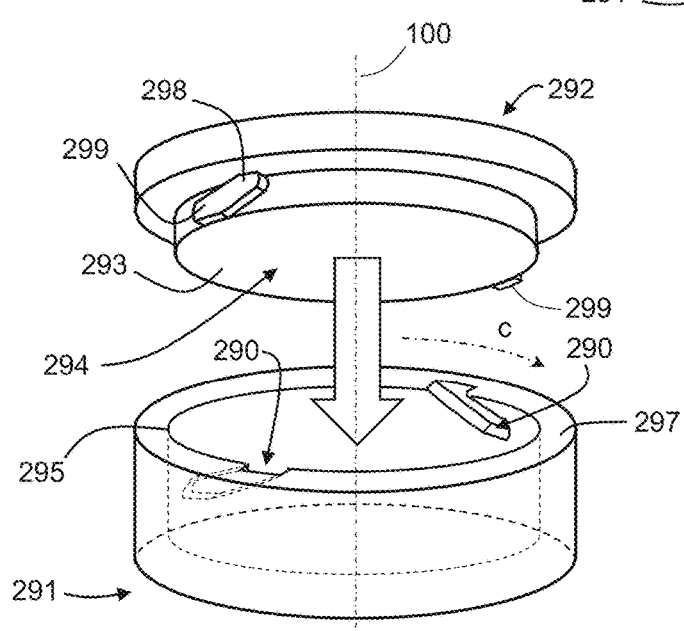
FIG. 39 shows a lidding body having a tapered thread segment that engages a matching tapered slot segment of a container body, for engaging the lidding body to the container body by a threading action.

FIG. 39 shows an embodiment of a lidding body 292 having a pair of partially tapered threads 298 extending outwardly from a projection portion 294 of the undersurface 293 of the lidding body 292. The lead edge 299 of each thread 298 is configured to engage with a tapered slot 290 within the inner wall 295 of the container body 291. The lead edge 299 of each thread 298 can be aligned with a respective slot 290 and then rotated in a clockwise direction, c, as the undersurface 293 of the lidding body 292 is lowered onto the upper surface 297 of the container body 291. The fitment of the outer surfaces of the thread 298 with the inner surfaces of the slot 290 maintains the lidding body 292 engaged with the container body 291 during subsequent handling, packaging and use of the article.

In another embodiment, any of the rapidly-orodispersible structures above can be formed in any 3DP equipment assembly with an open print bed. One such non-limiting example of a 3DP equipment assembly is described in U.S. Pat. No. 8,888,480, the disclosure of which is incorporated by reference in its entirety.

Figure 40:
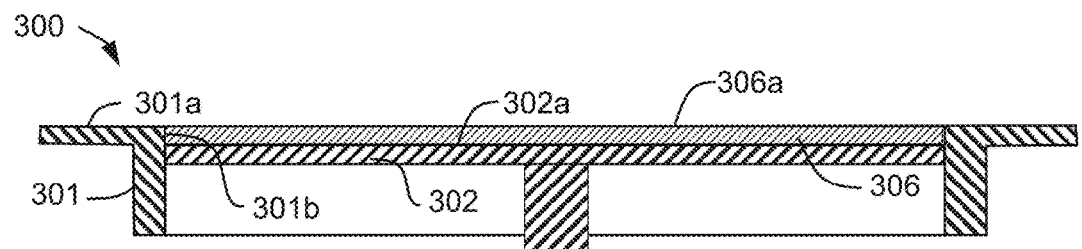
FIGS. 40-46 illustrate the forming of a plurality of container bodies within an open print bed.

FIG. 40 shows a partial cross-sectional view of a build module 300 comprising a body 301 having an inner wall 301b and an upper surface 301a and a height adjustable platform 302 having an upper surface 302a. A removable build plate 306 is placed on top of the platform 302. Process steps to form a rapidly-orodispersible dosage form are illustrated in a series of steps, labeled as steps A, B, C and D below, at various platform height-adjusted stages. The build module 300 and upper surface 306a of the removable build plate 306 is depicted in starting position at an initial platform stage 0.

Figure 41:
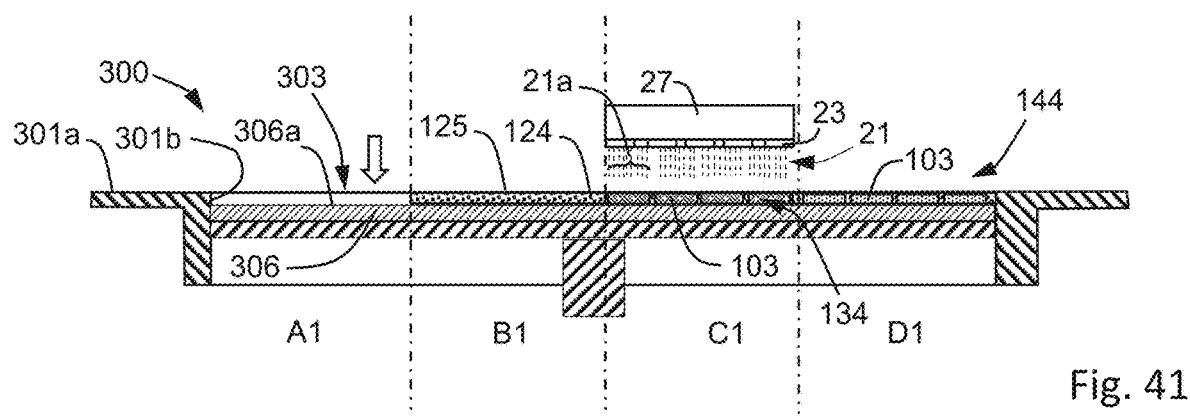

In step A1 shown in FIG. 41, the upper surface 306a of the removable build plate 306 is lowered (small arrow down) within the inner wall 301b of the build module 300, forming a cavity 303 bounded by the inner wall 301b and the upper surface 306a of the removable build plate 306. It should be understood that the segment illustration shown in step A1 extends across the entire build module.

In process step B1, a substantially uniform layer of powder 124 is deposited within the cavity 303 and its upper surface 125 made level with (at the same height of) the position of the upper surface 301a of the build module. Typically, the powder layer 124 is formed by depositing a volume of the powder material into the cavity 303 more than sufficient fill the entire volume of the cavity 303, and the upper surface leveled using a leveling blade or roller. It should be understood that the segment illustration shown in step B1 extends across the entire build module.

In process step C1, a printing liquid is deposited, in a predetermined pattern and in predetermined amounts, by a printing apparatus 27 expressing streams of droplets 21 from nozzles 23 onto the top surface 125 of the powder layer 124. In the illustrated process, a plurality of patterns of streams of droplets 21a are expressed, each pattern area being circular. The expressed printing liquid in the printed patterns forms a layer of printed powder 134 including the predetermined pattern of printed powder material and non-printed powder material. It should be understood that the segment illustration shown in step C1 extends across the entire build module.

After completing the liquid printing, the first layer of printed powder material 134 is formed into a first layer of bound powder 144, comprising predetermined patterned areas of bound powder and remaining areas of unbound (non-printed) powder material, shown in step D1. Each of the patterned areas of bound powder corresponds to an area and thickness of a circular base for a dosage form, such as circular base 3 shown in FIG. 1. It should be understood that the segment illustration shown in step D1 extends across the entire build module.

In some embodiments, the process of Steps A1, B1, C1 and D1 can be repeated in series, one or more additional times, to deposit a second layer of powder material, to deposit binding liquid in the printed patterns in registry with the printed powder material areas of the first layer of printed powder 134, and to form a plurality of thicker, two- (or more-) layered circular base for a container body.

Figure 42:
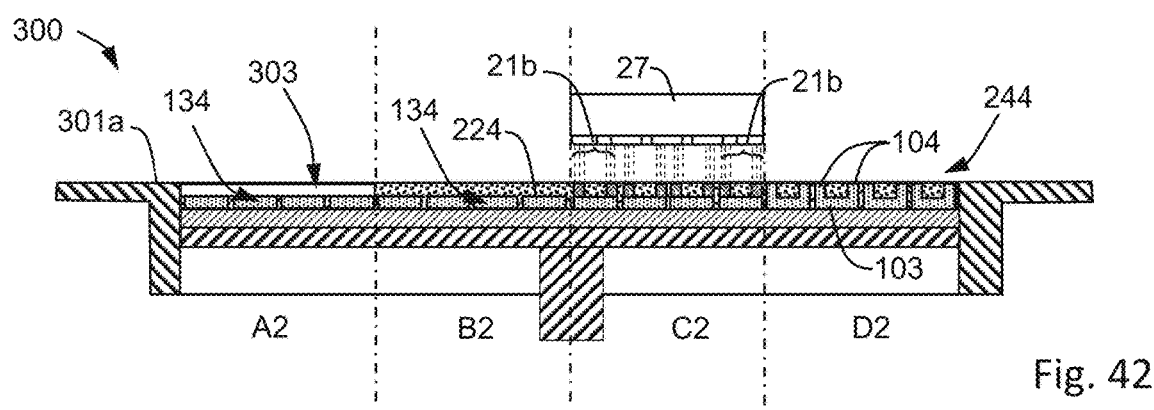

In step A2 shown in FIG. 42, the upper surface 306A of the removable build plate 306 is again lowered by an increment distance within the build module 300, re-forming a cavity 303 above the upper surface of the first layer(s) of bound powder 144.

In process step B2, another substantially uniform layer of powder 124 is deposited within the cavity 303 above the upper surface of the first layer(s) of bound powder 144, and its upper surface 125 made level with (at the same height of) the position of the upper surface 301a of the build module.

In process step C2, a printing liquid is deposited, in a second predetermined pattern and in predetermined amounts, by the printing apparatus 27 expressing streams of droplets 21 from nozzles onto the top surface of the second powder layer 224. In the illustrated process, a plurality of patterns of streams of droplets 21b are expressed, each pattern area being annular. The expressed printing liquid in the printed patterns forms a second layer of printed powder 234 including the predetermined pattern of printed powder material in the form of an outer ring with unwetted, unbound powder in a central area within the wetted outer ring.

After completing the liquid printing, the second layer of printed powder material 234 is formed into a second layer of bound powder 244, comprising predetermined patterned areas of bound powder and remaining areas of unbound (non-printed) powder material, shown in step D2. Each of the patterned areas of bound powder corresponds to an area and thickness of an annular wall for the dosage, such as annular wall 6 shown in FIG. 1, with unbound powder material within and between adjacent annular wall portions 104.

In some embodiments, the process of Steps A2, B2, C2 and D2 can be repeated in series, one or more additional times, to deposit an additional layer of powder material, to deposit binding liquid in the printed patterns in registry with the printed powder material areas of the first layer of printed powder 234, and to form a plurality of thicker, two- (or more-) layered annular walls for the container body. FIG. 43 illustrates the steps A3, B3, C3, and D3 for forming of a third layer of bound powder 344 on top of the second layer of bound powder 244, forming a second layer of annular wall 104.

The completion of the printing of the annular walls 104 completes a container body 101 as illustrated in FIG. 28. In some embodiments, the printing process can be stopped and the printed container bodies 101 removed from the build module 300 and the removable build plate 306, and separated from any unbound powder material.

Figure 44:
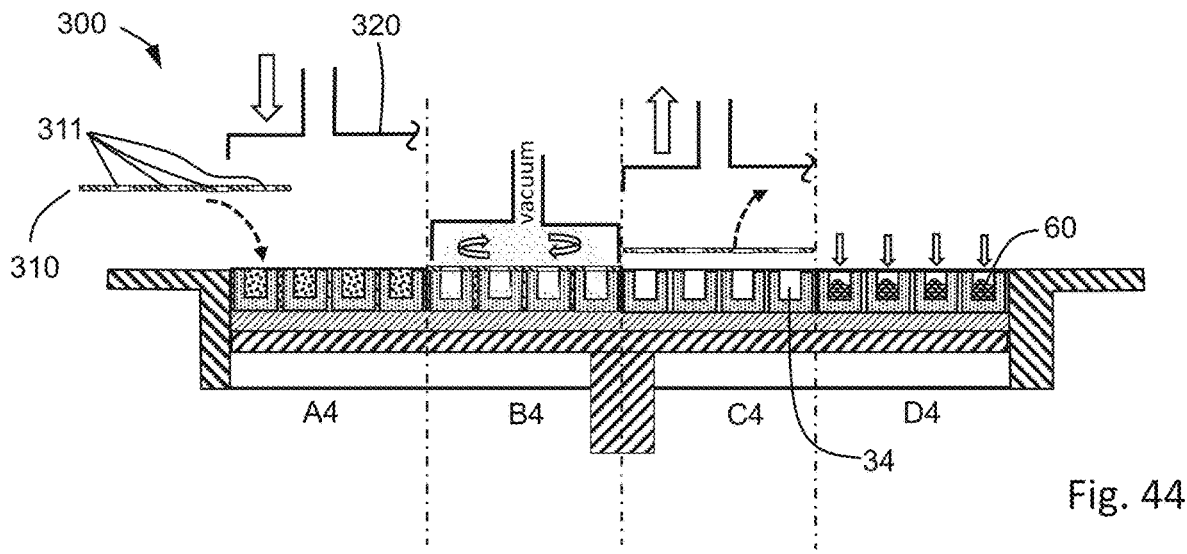

In step A4 shown in FIG. 44, a cavity mask sheet 310 is placed over the upper surface of the third layer(s) of bound powder 344, above the build module 300, and a vacuum hood 320 placed over the cavity mask sheet 310. The cavity mask sheet 310 includes a sheet or plate of a resilient material that extending across the open area of the build module. The cavity mask sheet 310 includes shaped openings 311 that are positioned in the cavity mask sheet 310 to register with each of cavities 34 of the plurality of container parts. Preferably, the cavity mask sheet 310 has an undersurface that is placed into a contact with the upper edges of the printed container parts, and the shaped openings 311 position to avoid fluidizing and evacuating unbound powder material that remains positioned between the outer surfaces of the formed container parts, to prevent or inhibit shifting or lateral movement of the formed container parts in subsequent process steps.

In step B4 shown in FIG. 44, the vacuum is applied and the drawn air fluidizes the unbound powder within the cavities of the printed container parts, without displacing or moving the printed, bound-powder container parts or the unbound powder between the container parts.

In step C4, the vacuum is halted and the vacuum hood 320 withdrawn from above the cavity mask sheet 310.

In step D4, a particulate payload material 60 comprising one or more medicaments is deposited in a pre-determined amount into each cavity 34. A pre-determined amount, by mass or volume, of the particulate payload material 60 can be mechanically dosed and/or metered into the cavities 34 by any means known in the art, non-limiting examples of which are described in U.S. Pat. Nos. 9,409,699 and 9,828, 119, and US Patent Publications 2017/0322068 and 2018/0031410, the disclosures of which are incorporated by reference in their entireties.

In step A5 shown in FIG. 45, the upper surface 306a of the removable build plate 306 is again lowered by an increment distance within the build module 300, re-forming a cavity 303 above the upper surface of the third layer(s) of bound powder 344 with the cavities filled with particulate payload material 60.

In process step B5, another substantially uniform layer of powder 424 is deposited within the cavity 303 above the upper surface of the third layer(s) of bound powder 344, and its upper surface made level with (at the same height of) the position of the upper surface 301a of the build module.

In process step C5, a printing liquid is deposited, in a fourth pre-determined pattern and in pre-determined amounts, by the printing apparatus 27 expressing streams of droplets 21 from nozzles onto the top surface of the fourth powder layer 424. In the illustrated process, a plurality of patterns of streams of droplets 21 are expressed, each pattern area being circular. The expressed printing liquid in the printed patterns forms a layer of printed powder 425 including the pre-determined pattern of printed powder material and non-printed powder material.

After completing the liquid printing, the fourth layer of printed powder material 425 is formed into a fourth layer comprising predetermined patterned areas of bound powder 444 and remaining areas of unbound (non-printed) powder material, shown in step D5. Each of the patterned areas of bound powder 444 corresponds to an area and thickness of a circular top for a dosage form 1, such as circular top 5 shown in FIG. 1.

Figure 46:
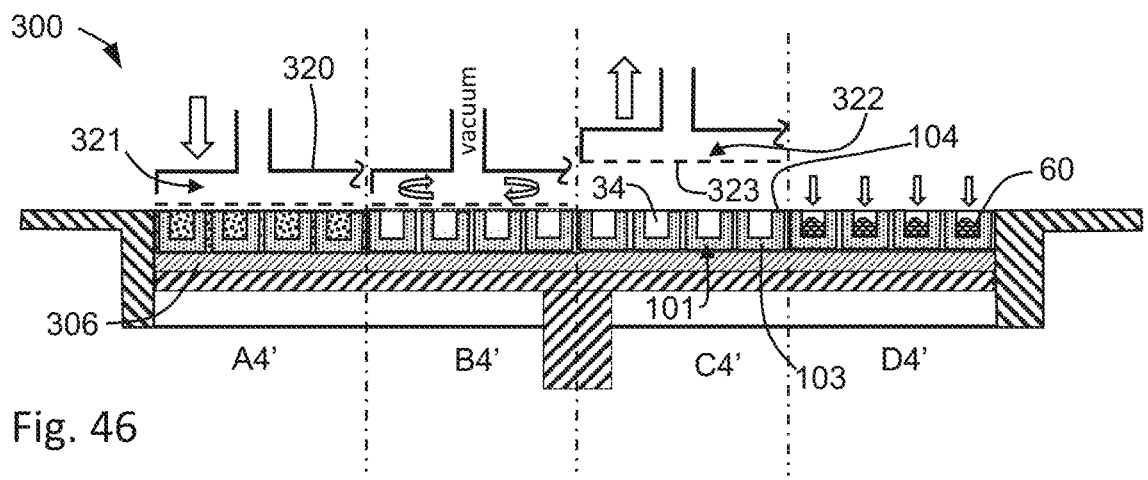

FIG. 46 shows an alternative process for extracting unbound powder from within the cavities 34 of the formed container bodies 101, as an option to the process described above for FIG. 44. Step A4' shows a vacuum hood 320 in placed over the upper surface of the third layer(s) of bound powder 344, above the build module 300. The vacuum hood 320 has an inlet open area 321 of substantially the upper open area of the build module 300. The vacuum hood 320 includes a coarse screen 322 extending across the inlet open area 321, the openings in the coarse screen 322 being sufficiently large to allow fluidized unbound powder material to be drawn into the vacuum hood 320 and into a powder recovery system, though not so large that printed container bodies 101 are not pulled into the vacuum system or moved from their positions. Preferably, the coarse screen 322 has an undersurface 323 that is placed into a contact with the upper edges of the printed container parts to prevent their movement upon the build plate 306.

In step B4' shown in FIG. 46, the vacuum is applied and the drawn air fluidizes the unbound powder within and surrounding the printed container bodies 101, substantially without displacing the printed, bound-powder container bodies 101.

In step C4' shown in FIG. 46, the vacuum is halted and the vacuum hood 320 withdrawn from above the build module 300. Each container body 101 is shown having a lower base 103 with an annular wall 104 surrounding a cavity 34.

In step D4' shown in FIG. 46, particulate payload material 60 comprising one or more medicaments is deposited in a pre-determined amount into each cavity 34. A pre-determined amount, by mass or volume, of the particulate payload material can be mechanically dosed and/or metered into the cavities 34 by any means known in the art, non-limiting examples of which are described in U.S. Pat. Nos. 9,409,699 and 9,828,119, and US Patent Publications 2017/0322068 and 2018/0031410, the disclosures of which are incorporated by reference in their entireties.

Figure 47:
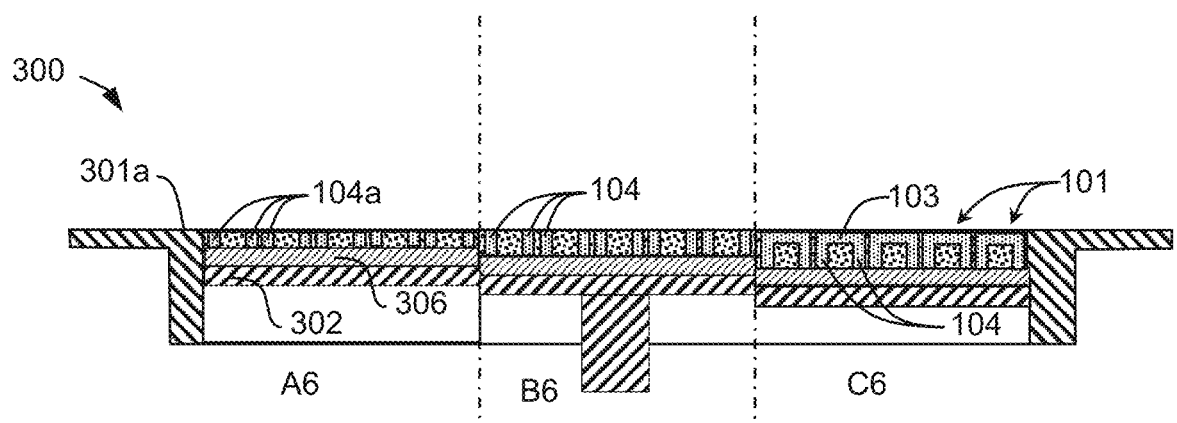
FIG. 47 shows an alternative process for forming a plurality of container bodies in a series of steps with the bottom side up, by forming in one or more layers an upper portion of a plurality of peripheral wall portions, then forming in one or more layers the remaining peripheral wall portions, and then forming a plurality of bases consisting of the bound powder matrix, upon the peripheral wall portions, to form the plurality of dosage container bodies.

FIG. 47 shows an alternative process for forming a plurality of container bodies in a series of steps, using the bound-powder printing processes described above, where in the container bodies are formed bottom sides up. The process in step A6 shows the completed steps after forming a powder layer and printing a binding liquid on selected portions of the powder layer to form a plurality of the upper peripheral wall portions 104a consisting of the bound powder matrix, illustrating that the top side of the container bodies (the upper portion of the peripheral walls) being formed down, while the process in step B6 shows the completed steps after forming a powder layer and printing a binding liquid on selected portions of powder layer to form the remainder of the peripheral walls 104 consisting of the bound powder matrix. The process in step C6 shows the completed steps after forming a powder layer and printing a binding liquid on selected portions of the powder layer to form a plurality of bases consisting of the bound powder matrix, upon the peripheral wall portions, to form the plurality of dosage container bodies with the bottom sides (bases) facing up. After forming the container bodies, the printed layers can be further processed to separate the container bodies from the unbound powder material, which can be recovered and optionally recycled. The separated container bodies can be optionally dedusted, and transported for further treatment and processing into dosage forms, or optionally packaged as separate articles.

Figure 48:
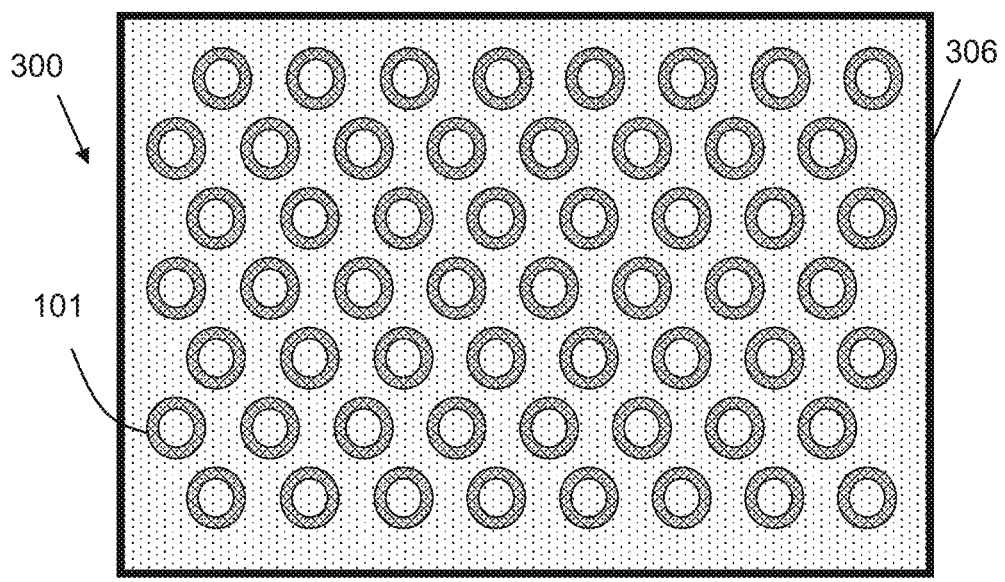
FIG. 48 shows a top plan view of an exemplary arrangement of a plurality of containers formed within an open print bed of a 3DP equipment assembly.

In an embodiment of the invention, which can be used with any other embodiment described herein, the rapidly-orodispersible dosage forms can be printed as an array of objects on top of the same build surface. A top view showing a sample distribution of an array of printed rapidly-orodispersible containers 101 on a build plate 306 is shown in FIG. 48. However, those skilled in the art would appreciate that any number of objects can be built on the same build surface in any pattern, based on the size of the build platform and the capabilities of the 3DP equipment assembly, and that other such examples are omitted for clarity.

In another embodiment, a plurality of lidding bodies can also be formed in a 3DP equipment assembly with an open print bed, according to the same or similar process as described and depicted above. In another embodiment, lidding bodies can be printed on a separate build surface from the container bodies. In another embodiment, lidding bodies can be printed simultaneously on the same build surface as the container bodies.

Unitary, Partially-Enclosed Dosage Form

Figure 49:
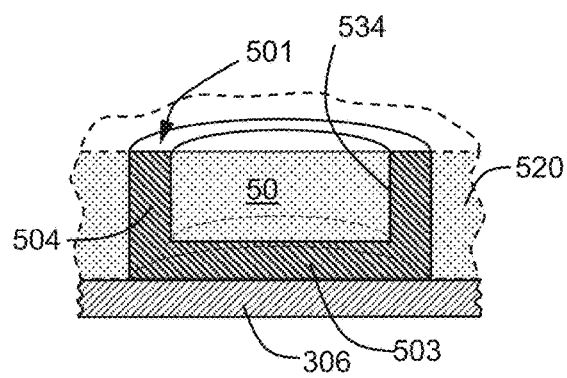
FIGS. 49-54 illustrate forming, filling and sealing a unitary, partially-enclosed dosage form having an internal cavity, formed in an open print bed of a 3DP equipment assembly.

FIGS. 49-54 illustrate forming, filling and sealing a unitary, partially-enclosed dosage form having an internal cavity, formed in an open print bed of a 3DP equipment assembly. FIG. 49 shows a sectional view of a container body 501 formed from a plurality of incremental layers of build powder material 520, the container body 501 having a base 503 and a peripheral wall 504, with a cavity 534 bounded by the peripheral wall 504 that is filled with the entrapped build powder material 50. A plurality of the container bodies being processed in an open print bed is shown in FIG. 43 at step D3.

In the present embodiment, as illustrated in FIG. 50, a build plate 306 of the open print bed is lowered an incremental distance, and a substantially uniform, incremental layer 524 of build powder material is applied over the formed container body 501 and build powder material 50, and an area (arrows) on the upper surface 525 of the build powder layer 524 illustrates where a printing liquid will be directed to form a bound powder matrix. The area (arrows) has a periphery that is coextensive with the outer peripheral wall 504 of the container body 501, and includes an interior area where the printing (binder) liquid will not be printed, and consequently, the build powder material will not be transformed into a bound powder matrix.

FIG. 51 shows a sectional view of the formed unitary, partially-enclosed dosage form 509, resulting from the printing of the printing liquid. The formed unitary, partially-enclosed dosage form 509 has an internal cavity 534 filled with unbound powder material 50, and a top lid 506 formed of the bound powder matrix by the selected printing of the build powder layer 524. The bound powder matrix of the top lid 506 is secured or unitarily formed with the upper edge of the peripheral wall 504. The top lid 506 has a port opening 508 formed from unwetted and unbound build powder of the build powder layer 524.

FIG. 52 shows the use of an evacuation system to remove the unbound powder material from within the cavity through the port opening. An evacuation system V evacuates or removes the unbound build powder material 50 from within the cavity 534, through the port opening 508 in the lid 506. In the illustrated embodiment, the evacuation system is illustrated as a vacuum system which draws air and the fluidizing unbound build powder material 50 from within the cavity 534. A distal tip of a tube 87 connected to the vacuum system V can be inserted into port opening 508 in the lid 506 to assist in evacuating most or all of the unbound build powder material 50, to leave an empty or substantially empty cavity 534. The inlet opening in the tube 87 should be larger than the largest particle size of the particulate build powder material. The inlet opening in the tube 87 can be manually inserted into the port opening, or can be mechanical inserted under automatic control.

After most or all of the unbound build powder material 50 is evacuated from the cavity 534, a payload material 60 can be deposited into the evacuated cavity. FIG. 53 shows a means for partially or completely filling the empty cavity 534 through the port opening 508 in the lid 506, with a payload material 60. The payload material can be deposited into the cavity 534 by any well-known means, such as a pipette 88 as illustrated, or an injection needle, which can be inserted through the port opening 508 and into the cavity 534 to avoid spillage or loss of the payload material. The payload material can be any of the solid, particulate, liquid, semi-solid or engineered particles and materials described herein. In some embodiments, after the payload material 60 has been deposited into the cavity, a filler material (not shown, but described herein) that is typically inert with the payload material, can be deposited to fill the remaining volume of the cavity 534. In some embodiments, only a small portion of the unbound build powder material 50 can be withdrawn from the cavity 534, the small portion by volume being sufficient to provide space for a small amount or volume of a payload material 60.

The unbound build powder 50 contained with the cavity 586 of the partially-enclosed dosage form 509 can be evacuated while the dosage form 509 remains in the open print bed, as illustrated in FIG. 52, or can be further processed remote from the open print bed to separate the partially-enclosed dosage form 509 from the unbound powder material, which can be recovered and optionally recycled. The separated partially-enclosed dosage form 509 can be optionally dedusted, and transported for further treatment and processing into dosage forms, or optionally packaged as separate articles.

After the payload is deposited into the cavity 534 of the partially-enclosed dosage form 509, the port opening 508 in the lid 85 can be closed and sealed to prevent the payload 60 and any remaining unbound build powder material 50 from escaping the cavity, forming a finished unitary dosage article 550 containing a payload, and further, a rapid-orodispersive unitary dosage article containing a payload material, such as a medicament, within the sealed, interior cavity. FIG. 54 shows a plug 589 filling and sealing the port opening 508. The sealing material of the plug 89 can be a solid or solidifying material, and preferable a water-soluble and ingestible material. A preferred material is a solid or waxy material at normal room or storage temperatures, and meltable at elevated temperatures to flow into and seal the edges of the port opening 86. Non-limiting examples of a sealing material are fats, water-soluble polymers, polyethylene glycol, carbohydrates and carbohydrate alcohols, including any one or more thermal binding materials as described herein.

In another embodiment, rather than forming the port opening within the unitary lid, a port opening can be formed into a peripheral wall of the dosage form, and into fluid communication with the internal cavity within the container. An advantage of forming the port opening in the peripheral of a disk-shaped dosage form can be that the bound powder matrix of the peripheral wall surrounding the port opening has better structural integrity than the lid portion or the base of the container body. The portion of the peripheral wall in which the port opening is formed can also be formed more thickly for better structural integrity. The top lid portion and base portions of dosage forms are stamped, embossed or printed with a logo or other mark for the dosage form product, and forming a port opening into a peripheral wall of the dosage form avoids marring of the logo or other mark.

FIG. 55 shows a formed unitary, partially-enclosed dosage form 509 having a port opening 518 formed in a peripheral wall 504, into fluid communication with the internal cavity 534 within the container 501. The port opening 518 is formed from unwetted and unbound build powder that was not wetted or printed during the printing of the peripheral wall segments in previously-deposited build powder layers. A continuous top lid portion 506 can be printed onto the upper-most build powder layer 525, thereby forming the unitary, partially-enclosed dosage form 509 with the unwetted port opening 518.

The build powder 50 contained within the cavity 534 can be removed or evacuated as described above, for example, by a vacuum system. As shown in FIG. 56, a payload material 60 can be deposited into the evacuated cavity 534 through the port opening 518 in the peripheral wall 504, by any well-known means, as described above. After the payload is deposited into the cavity 534 of the partially-enclosed dosage form 509, the port opening 518 in the peripheral wall 504 can be closed and sealed to prevent the payload 60 and any remaining unbound build powder material 50 from escaping the cavity, as described above and illustrated in FIG. 52.

In another embodiment, a port or opening for removing unbound powder material from a filled or partially-filled cavity can be formed after the printing of a unitary dosage form is completed, as illustrated in FIGS. 57-60. Similar to FIG. 50, FIG. 57 illustrates a sectional view of a container body 501 atop of an open print bed 306, the container body 501 formed from a plurality of incremental layers of build powder material 520, the container body 501 having a base 503 and a peripheral wall 504, with a cavity 534 bounded by the peripheral wall 504 that is filled with the entrapped build powder material 50. A substantially uniform, incremental layer 524 of build powder material is applied over the formed container body 501 and build powder material 50, and an area (arrows) on the upper surface 525 of the build powder layer 524 illustrates where a printing liquid will be directed to form a bound powder matrix. In contrast to the application of printing liquid as illustrated in FIG. 50, although the area (arrows) has a periphery that is coextensive with the outer peripheral wall 504 of the container body 501, the entire incremental layer 524 is contacted with the printing (binder) liquid, therefore transforming the entire incremental layer 524 into a bound powder matrix, and forming a lid portion 506 unitary with the container body 501, as shown in FIG. 58. The formed unitary, fully-enclosed dosage form 519 has an internal cavity 534 filled with unbound powder material 50. The bound powder matrix of the top lid 506 is secured or unitarily formed with the upper edge of the peripheral wall 504.

FIG. 59 shows a sectional view of the use of a boring means 55, illustrated in FIG. 59 as a drill bit to create a port opening 528 in the peripheral wall 504 of the unitary, fully-enclosed dosage form 519. Once the port opening 528 is created, an evacuation system, V, can also be used to evacuate or remove the unbound build powder material 50 from within the cavity 534, through the port opening 508 in the peripheral wall 504. In the illustrated embodiment, the evacuation system V is illustrated as a vacuum system which draws air and either a portion of the bound matrix when forming the port opening 528, or unbound build powder material 50 from within the cavity 534. As illustrated in FIG. 52, a distal tip of a tube 87 connected to the evacuation system V can be inserted into port opening 508 in the lid 506 to assist in evacuating most or all of the unbound build powder material 50, to leave an empty or substantially empty cavity 534.

After most or all of the unbound build powder material 50 is evacuated from the cavity 534, a payload material 60 can be deposited into the evacuated cavity. FIG. 60 shows a means for partially or completely filling the empty cavity 534 through the port opening 528 in the peripheral wall 504, with a payload material 60. The payload material can be any of the solid, particulate, liquid, semi-solid or engineered particles and materials described herein, and can be deposited through the port opening 528 and into the cavity 534 by any well-known means, as described above. In some embodiments, after the payload material 60 has been deposited into the cavity, a filler material (not shown, but described herein) that is typically inert with the payload material, can be deposited to fill the remaining volume of the cavity 534. In some embodiments, only a small portion of the unbound build powder material 50 can be withdrawn from the cavity 534, the small portion by volume being sufficient to provide space for a small amount or volume of a payload material 60.

One or both of the formation of the port opening 528 and the evacuation of unbound build powder 50 contained with the cavity 534 of the fully-enclosed dosage form 519 can occur while the dosage form 519 is still on the open print bed (not shown). Alternatively, fully-enclosed dosage forms 519 can be further processed remotely from the open print bed to form the port opening 528 and/or separate the fully-enclosed dosage form 519 from the unbound powder material, which can be recovered and optionally recycled.

After the payload 60 is deposited into the cavity 534 of the dosage form 519, the port opening 528 in the peripheral wall 504 can be closed and sealed to prevent the payload 60 and any remaining unbound build powder material 50 from escaping the cavity, forming a finished unitary dosage article 560 containing a payload 60, and further, a rapid-orodispersive unitary dosage article containing a payload material, such as a medicament, within the sealed, interior cavity 50. FIG. 60 shows a plug 589 filling and sealing the port opening 528. Any of the sealing materials described above can be utilized to form the plug and seal the edges of the port opening 528.

In another embodiment, rather than forming the port opening 528 within the peripheral wall 504, a port opening can instead be formed into the unitary lid 506 of the dosage form 519, and into fluid communication with the internal cavity 534 within the container 501 (not shown).

Printing Liquid

In another embodiment, the spacing of droplets of printing liquid dispensed by a 3DP equipment assembly, including any of the systems described above, can be described in terms of the resolution of the printing system, often expressed as dots per inch (dpi), which is the reciprocal of droplet spacing. For example, resolutions of 300 and 600 dpi correspond to droplet spacings of about 84.7 microns and about 42.3 microns, respectively. The drop-to-drop spacing (within a line), or the line spacing (spacing of droplets from one line to the next), or any other spacing of droplets may be described in terms of resolution expressed in dpi. In some embodiments, layer-by-layer instructions for making the dosage forms may consist of a series of pixelated images characterized by a resolution in dpi in each of two orthogonal linear directions. In some instances, these pixelated images are 1-bit monochrome images, alternately referred to as binary or bi-level images in which each pixel contains one bit of information (0 or 1) that may be represented as either black or white onscreen.

In other embodiments, layer-by-layer instructions for making the dosage forms may consist of a series of voxels, or unit volumes, defined by one drop-to-drop spacing in the fast axis direction of motion, by one line-to-line spacing in the slow axis direction of motion, and by one layer thickness in the vertical direction. Some of the unit volume can be occupied by powder particles, while the remainder of the unit volume can be empty space, referred to as the void volume. As used herein, the terms, "saturation level," or "print density," describes how much of the void volume is occupied by liquid dispensed as a drop or fluid unit within that particular voxel. The saturation level can also describe the ratio of the dispensed fluid volume to the volume of empty space in the voxel. In general, saturation levels may be chosen to be slightly less than, or somewhere approximately equal to, 1.0 (also expressed as 100% saturation). In some embodiments, the saturation level of printing steps in any of the 3DP-based methods described herein during can range from about 10% to about 110%, about 15% to about 80%, about 20% to about 50% or about 15% to about 35%, either in aggregate across the dosage form, or otherwise in selected regions of the dosage form.

In some instances, the relative amount of binding in localized regions of the dosage form is achieved by "grayscaling" (i.e., use of a grayscale print pattern) in the dosage form design. In the case of 1-bit monochrome images used for machine instructions, grayscaling is achieved by changing the number of "black" pixels relative to "white" pixels in a chosen region of a dosage form, or in a chosen layer of a dosage form, or throughout a dosage form. Any other regions that may be "solid" by using all black pixels. In some embodiments, the dosage form design includes a "solid" exterior and a "grayscaled" interior. In some embodiments, grayscaling may be achieved with equally spaced black pixels amongst white pixels to reach an overall ratio of black to white pixels in the grayscaled region. In other embodiments, grayscaling may be achieved with randomly placed black pixels amongst white pixels to achieve an overall ratio of black to white pixels in the grayscaled region. In still other embodiments, grayscaling may be achieved with a chosen pattern (e.g., parallel lines, hashed pattern, dot pattern) of black pixels amongst white pixels to achieve an overall ratio of black to white pixels in the grayscaled region.

In various embodiments, the printing system may apply droplets at different respective droplet spacing for each of two orthogonal linear directions. The dpi for each direction may vary based on the 3DP system used, and in some instances may vary based on such factors as the total count and native spacings of nozzles on the printhead, the axis and velocity of relative motion between printhead and substrate (i.e., articles being formed), and the timing frequency with which each nozzle can eject a unique droplet. These and related factors are recognized and are well known in the art. In one non-limiting example, a first droplet spacing is selected from 200 dpi to 500 dpi with respect to a first orthogonal linear direction, and a second droplet spacing is selected from 700 dpi to 1800 dpi with respect to a second orthogonal linear direction.

Suitable printing devices can include those having a continuous jet printhead or those having a drop-on-demand printhead. A continuous jet printhead provides a continuous jet, or spray, of droplets while depositing printing fluid onto a powder layer. A drop-on-demand printhead only deposits droplets of printing fluid onto the powder layer if it receives an instruction, demand, or operational command to do so. A printhead may scan, or apply fluid to, the surface of powder layer from left to right, or from fright to left, at a predetermined rate, e.g., a scan rate, to form a line of droplets.

Without being limited by a particular theory, it is believed that a high scan rate will result in a lower saturation level, and a low scan rate will result in a higher saturation level when comparing printing fluid deposition at a constant volume per unit time. When binder material is present in the binding solution, it is believed that a doubling of the print speed, for example from 1.0 m/s to 2.0 m/s, can reduce the total volume of binder solution deposited in the tablets by approximately half (assuming constant dispensing rate from the nozzle). In contrast, it is believed that as the print speed increases, the bulk density of the tablet decreases. A simultaneous decrease in the dimensions and weight of the tablets may also be seen, and may be attributed to the fact that a decrease in the total volume of binder droplets deposited onto the powder can result in a decrease in the extent of binder solution spreading in the powder. Additionally, it is believed that increasing the print speed can also decrease the flash time and hardness, as well as increase the friability of the tablets, as a result of decreasing the proportion of decreases in the tablets as the print speed increases. It is also believed that an increase in the print speed can also increase the void volume inside the tablets When using a continuous jet print head, the print head may scan at a rate of about 0.5 m/sec to 3.0 m/sec. When a drop-on-demand jet print head is used, the print head may scan at a rate of 0.1 m/sec to 1 m/sec, or from about 0.15 m/sec to about 0.5 m/sec.

Generally, the size or volume of individual droplets can be varied as desired, for example, by selection of a different 3DP equipment assembly, or different printhead components on the same machine, or different parameters on the same printhead and same machine. Without being limited by a particular theory, it is believed that increasing the size or volume of the droplet can increase the saturation level, while decreasing the size or volume of a droplet can reduce the saturation level when the printing fluid is deposited at a constant scan rate. In another embodiment, when using a continuous jet printhead, the size of the fluid droplets delivered by the printhead can be in a range from about 15 microns to about 150 microns in diameter. In another embodiment, when using a drop-on-demand printhead, the size of the fluid droplets delivered by the printhead can be in a range from about 50 microns to about 500 microns in diameter.

The flow rate of the fluid delivered by the printhead can also be varied as desired. Without being limited by a particular theory, it is believed that increasing the flow rate can increase the saturation level, and decreasing the flow rate can reduce the saturation level when the printing fluid is deposited at a constant scan rate. Generally, the printhead can deposit droplets of printing fluid to form parallel lines thereof in the powder layer. In another embodiment, when using a continuous jet printhead, the line spacing can be in a range from about 20 microns to about 1000 microns, from about 50 to about 500 microns, or from about 100 to about 200 microns. In another embodiment, when using a drop-on-demand jet printhead, the line spacing can be in a range from about 20 microns to about 300 microns, from about 40 microns to about 100 microns, or from about 55 microns to 75 microns.

In another embodiment, the mass of moisture within a dosage form can be quantified as a percent by mass that is lost as a result of drying (LOD). In another embodiment, the dosage form can comprise not more than 10% by weight, not more than 7.5% by weight, not more than 5% by weight, not more than 4% by weight, not more than 3% by weight, not more than 2.5% by weight, not more than 2% by weight, or not more than 1.5% by weight of moisture, as determined by LOD at 120° C. In another embodiment, the dosage form can comprise at least 0.1% by weight, at least 0.2% by weight, at least 0.5% by weight, at least 0.75% by weight, at least 1% by weight, at least 1.5% by weight, at least 2% by weight, at least 2.5% by weight, at least 3% by weight, at least 4% by weight, or at least 5% by weight of moisture as determined by LOD at 120° C. In another embodiment, the dosage form comprises moisture in any range between and inclusive of 0.1% by weight and 10% by weight, including but not limited to: from at least about 0.1% by weight, up to about 10% by weight; or at least about 0.2% by weight, up to about 7.5% by weight; or at least about 0.5% by weight, up to about 5% by weight; or at least about 0.5% by weight, up to about 4% by weight; or at least about 1% by weight, up to about 3% by weight.

Powder Bed Selective Thermal Bonding

In an embodiment of the invention, a powder bed selective thermal bonding process and apparatus can be used to form a thermofused dosage form from a thermofusable powder material using a heat energy source.

In another embodiment, the thermofused dosage form can be formed within a depression of a dosage form package, such as a blister package.

FIG. 61 illustrates on the left side, L, a first layer 620 of a thermofusable powder material 650 of a substantially-uniform thickness, t, formed within the base 12 of a depression 10 of a dosage form package, and on the right side, R, the emissions a matrix of light-emitting elements 623 of a heat-emitting source 622 are controlled to direct the heat energy 621 across the entire surface of the first powder layer 620 for increasing the temperature of the thermofusable powder material, which upon cooling forms a stabilized granular agglomerate of a thermofused first layer 624.

FIG. 62 illustrates on the left side, L, a subsequent or second layer 625 of the thermofusable powder material 650 formed onto the stabilized granular agglomerate 624 of the thermofused first layer, and on the right side, R, the heat-emitting source 622 targets the heat energy 621 at the thermofusable powder material in a selected peripheral portion 625*c* of the thermofusable powder material 650 of the second layer 625, thermally bonding the thermofusable powder material within the selected peripheral portion 625*c* into a stabilized granular agglomerate, which also bonds or attaches to the thermofused first layer 624 therebelow, while limiting or avoiding the application of the heat energy upon the remaining central portion 625*d* of the second layer 625 of thermofusable powder material that remains unbonded and un-agglomerated.

FIG. 63 illustrates on the left side, L, a subsequent or third layer 626 of the thermofusable powder material 650 formed onto the selectively thermofused second layer 625, and on the right side, R, the heat-emitting source 622 targets the heat energy 621 at the thermofusable powder material 650 in a selected peripheral portion 626*c* of the third layer 626, again thermally bonding the thermofusable powder material within the selected peripheral portion 626*c* into a stabilized granular agglomerate, which also bonds or attaches to the stabilized granular agglomerate of the peripheral portion 625*c* of the second layer 625 below, while limiting or avoiding the application of the heat energy upon the remaining central portion 626*d* of the third layer 626 that remains unbonded and un-agglomerated.

FIG. 64 illustrates a partially thermofused article with five completed layers, with the fourth 627 and fifth 628 layers formed substantially as the third layer 626, where on the left side, L, a subsequent or sixth layer 629 of the thermofusable powder material 650 is formed onto the selectively thermofused fifth layer 628, and on the right side, R, the heat-emitting source 622 targets the heat energy 621 at the thermofusable powder material 650 in a selected peripheral portion 629*c* of the sixth 629 layer, again thermally bonding the thermofusable powder material within the selected peripheral portion 629c into a stabilized granular agglomerate, which also bonds or attaches to the stabilized granular agglomerate of the peripheral portion 628c of the fifth layer 628, while limiting or avoiding the application of the heat energy upon the remaining central portion 629d of the sixth layer 629 that remains unbonded and un-agglomerated.

FIG. 65 illustrates on the left side, L, the partially-formed container of FIG. 64, with a vacuum system 35 withdrawing the unbound thermofusable powder 650 out of the central portion, to leave an empty cavity 634, and on the right side, R, a complete filling of the empty cavity 634 with a particulate (payload) medicament 660 to an upper surface 661.

FIG. 66 illustrates on the left side, L, a top or last layer 670 of the thermofusable powder material 650 is formed onto and above the upper surface of the peripheral thermofused portion 629c of the sixth layer (629) and the upper surface 661 of the central portion-filling medicament 660, and on the right side, R, the heat-emitting source 622 directs the heat energy 621 across the entire surface 662 of the top layer 670 of thermofusable powder material 650, which upon cooling forms a stabilized granular agglomerate of a thermofused top layer 672, enclosing the medicament 660 within the walled cavity 634 of the stabilized granular agglomerate of the resulting dosage form 680.

The thermal binder is a material a glass transition temperature in the range of about 20 to about 160° C., preferably about 40 to about 140° C., more preferably about 55 to about 100° C. The thermal binder can be crystalline or amorphous and has the capability, after melting, to re-solidify upon cooling to below its glass transition temperature. Examples of suitable thermal binders include fats such as cocoa butter, hydrogenated vegetable oil such as palm kernel oil, cottonseed oil, sunflower oil, and soybean oil, mono, di, and triglycerides, phospholipids, waxes such as Carnauba wax, spermaceti wax, beeswax, candelilla wax, shellac wax, microcrystalline wax, and paraffin wax, water soluble polymers such as polyethylene glycol, polycaparactone, suitable fatty acid esters including sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides, polyethylene oxides and derivatives, and sucrose esters. Preferably, the thermal binder is selected from hydrogenated vegetable oil, polyethylene glycol, waxes, and mixtures thereof. In one embodiment more than one thermal binder is used and contained in the thermofusable powder material.

A particularly preferred thermal binder is polyethylene glycol (PEG) having at least 95% by weight of the PEG particles less than 100 microns as measured by conventional means such as light or laser scattering or sieve analysis and a molecular weight between 3350 and 8000 Daltons.

The amount of thermal binder present in the thermofusable powder material mixture is proportional to the particle size of the thermal binder used. Where up to 95% by weight of the thermal binder in the thermofusable powder material (and the thermofused bound matrix) has a particle size of less than about 100 microns (as measured by conventional means such as light or laser scattering or sieve analysis), the thermofusable powder material can comprise a range of 10-20% by weight of thermal binder. Where more than 50% by weight of the thermal binder in in the thermofusable powder material (and the thermofused bound matrix) has a particle size between about 100 and about 400 microns as measured by sieve analysis, the thermofusable powder material can comprise a range of 15-40% by weight of thermal binder. The lower particle size of a thermal binder powder contributes a higher surface area within the bound matrix, wherein the thermal binder contributes a greater binding effect when heated and then cooled.

Another component of the thermofusable powder material is at least one carbohydrate or carbohydrate alcohol selected from the group consisting of dextrose, sucrose, erythritol, mannitol, sorbitol, maltitol, xylitol, lactose, isomalt, starch hydrolysates, which include dextrins, dextrates, and maltodextrins, and the like, and mixtures thereof. The carbohydrate material contributes to the dissolvability and mouthfeel of the resulting dosage form, and also by aiding in distributing the dry thermal binder across a broader surface area. The carbohydrate may be present at level of about 5 percent to about 95 percent of the dosage form, e.g., about 20 percent to about 90 percent or about 40 percent to about 80 percent of the dosage form.

As the particle size of the thermal binder is decreased, less heat (in terms of time of heating and temperature) is needed to melt the outer surface of the thermal binder particles to fuse the agglomerate and achieve the same hardness. In one embodiment the particle size of the of carbohydrate or carbohydrate alcohol can influence the level of thermal binder used, wherein a higher particle size of carbohydrate or carbohydrate alcohol provides a lower surface area and subsequently requires a lower level of thermal binder. In one embodiment, wherein the thermal binder comprises 10-20% by weight of the thermofusable powder material when the carbohydrate or carbohydrate alcohol has a mean particle size of the carbohydrate or carbohydrate alcohol is greater than 100 μm and is greater than 50% by weight of the thermofusable powder material.

As described herein for a bound matrix that is formed by depositing and/or forming a layer of powder material and wetting with a binding liquid, the layer of thermofusable powder material can optionally be tamped or compressed after formation and prior to the heating or fusing step, in order to reduce void space and remove air from the thermofusable powder mixture. In one embodiment the tamping step is not enough pressure or force to hold the tablet shape together. In one embodiment the tamping step is conducted using a force less than 0.3 kiloNewtons. In various embodiment, the bound matrix or granular agglomerate can be tamped as the bound matrix is cooling, and before it has fully cooled and hardened.

Temperatures of the thermofusable powder material and the granular agglomerate formed therefrom can be measured using a thermocouple temperature measuring sensor, such as a thermocouple Type K commercially available from the Hewitt Industries.

The thermofusable powder material in the formed layer can be heated to a temperature and for a period of time to softener and/or melt the thermal binder partially or substantially throughout the powder layer. The melted thermal binder begins to flow and forms a fused aggregate portion, fusing multiple particles together, and fusing the layer of thermofusable powder material to a bound powder layer below. The other particulate components in the thermofusable powder can remain solid and maintain their physical properties, including hardness. The time of heating is dependent on the species of thermal binder and its particular size dimensions, and particularly the thickness, of the layer of thermofusable powder material, and must be sufficient in conjunction with the temperature to fuse and stabilize the particulate agglomerate.

A suitable heat source to heat selected portions in the plane of the layer of thermofusable powder material should be directed at specific planar surfaces of the layers, with high resolution, in order to avoid heating of portions of the powder layer which are intended not to be heated and agglomerated. A suitable heat source can be a radiant heater, conductive heating, convective heating, radiofrequency heating, sonic heating, microwave heating, or laser heating. In various embodiments, the heat source includes a means for selectively directing the heat energy for increasing the temperature of the thermofusable powder material only upon and into the planar portion of the layer of powder that is to be thermally bonded, while limiting or preventing the heat energy upon or into the remaining planar portions of the layer of powder that is remain unbonded and un-agglomerated.

In one embodiment, said means can comprise a targeting heat source that targets heat energy only at the areas of the thermofusable powder layer to be bonded. Non-limiting examples of such targeting heat energy can include a laser heat source.

In a preferred embodiment, the laser heat source emits electromagnetic radiation at a wavelength, and can include one or more lasers. Types of lasers can include, for example, CO2 lasers, infrared lasers, and diode lasers such as blue diode lasers. The thermal binder material, causing the thermal binder material to be heated and to soften and/or melt after being heated to its glass transition or melt temperature. The electromagnetic radiation can be electromagnetic radiation within the infrared, visible or ultraviolet regions of the electromagnetic spectrum. The laser power can be measured in watts, and is at least 0.5 W, including at least 1 W, at least 1.5 W, and at least 2 W, and up to 140 W, including up to 80 W, up to 7 W, up to 5 W, and/or up to 3 W.

The laser emits electromagnetic radiation having a wavelength in the range of from 200 nanometers (nm) to 11 micrometers (µm), preferably 315 nm to 1.4 µm, more preferably 380 nm to 800 nm, such as 400 nm to 610 nm, preferably 400 nm to 500 nm, more preferably 430 nm to 470 nm. Other suitable wavelength ranges can include 9.4 to 11 µm, such as 10.2-10.8 µm, preferably around 10.6 µm. Another suitable laser emits electromagnetic radiation in the range of 750-850 nm, such as approximately 800 nm.

The targeted heating with the laser heat source is performed using a scan speed in the range of from 5 mm/s to 50,000 mm/s, preferably from 10 mm/s to 1,000 mm/s, more preferably from 20 mm/s to 300 mm/s and most preferably from 30 mm/s to 200 mm/s.

The selective laser activation is performed using a surface temperature in the range of 0-200° C., preferably 40-180° C., most preferably 70-170° C.

The parameters that can be varied typically include the type of laser and thus its wavelength, as well as the laser power, scan speed, print resolution (layer height), beam spot size, surface temperature of the thermofusable powder material layer, the ambient or chamber temperature, and the initial position of the build platform and its lowering speed.

In various embodiments, a height of the layer of thermofusable powder material is in the range of 0.001 mm to 15 mm, which can include at least 0.025 mm, at least 0.05 mm, at least 0.1 mm, and at least 0.5 mm, and up to 10 mm, including up to 5 mm, up to 2 mm, and up to 1 mm.

Suitable laser beam spot size is typically in the range of from 0.0025 mm to 1 mm, for example 0.05-0.5 mm, preferably 0.1-0.3 mm, for example 0.2 mm. Increasing the spot size can be used to increase the laser beam interaction time. Typically, this is influenced by adjusting the scan speed.

In another embodiment, said means can comprise a heat source that directs heat energy at the areas to be bonded, while shielding the delivery of the heat energy at or onto areas of the thermofusable powder layer that are to remain unbonded and un-agglomerated. Non-limiting examples of such directing heat energy can include a radiant source, convective heating, radiofrequency heating, sonic heating, or microwave heating, while a shielding means can include an areal template that is applied upon to cover the surface of the portion of the layer of thermofusable powder that is to remain unbound, where the template is a material that can reflect away or absorb the heat energy, to prevent or greatly restrict its penetration therethrough to the powder material beneath.

FIGS. 67 and 68 illustrate selected steps in a process for forming of one or more porous articles, each having one or more internal cavities disposed inside. A method can include the steps of depositing a layer of thermofusable powder material, positioning a shield over the upper surface of the powder layer, and directing heat energy through the one or more openings in the shield to selectively bond the thermofusable powder material into a stabilized granular agglomerate, while leaving the portions of the thermofusable powder material that are shielded from the heat energy to remain unbonded and un-agglomerated.

FIG. 67 illustrates a module 700 similar to the build module 300 shown and described in FIG. 40. In step A-1, the upper surface 706a of the removable build plate 706 is lowered (small arrow down) within the inner wall 701b of the build module 700, forming a cavity 703 bounded by the inner wall 701b and the upper surface 706a of the removable build plate 706. It should be understood that the segment illustration shown in step A1 extends across the entire build module.

In process step A-2 of FIG. 67, a substantially uniform layer of thermofusable powder 724 is deposited within the cavity 703 and its upper surface 725 made level with (at the same height of) the position of the upper surface 701a of the build module. Typically, the thermofusable powder layer 724 is formed by depositing a volume of the thermofusable powder material into the cavity 703 more than sufficient to fill the entire volume of the cavity 703, and the upper surface is leveled using a leveling blade or roller. It should be understood that the segment illustration shown in step A-2 extends across the entire build module.

In process step A-3 of FIG. 67, a shield 590 is positioned above the upper surface 725 of the thermofusable powder layer 724. The shield 590 is typically a planar material 591 having openings formed through the planar material, and is placed above and substantially parallel to the upper surface 725 of the thermofusable powder layer 724. In some embodiments, the heat source is a laser light source. The planar material can be formed from one or more materials that can reflect away or absorb the heat energy of the laser light, to prevent or greatly restrict penetration of the laser-light heat energy therethrough to the powder material beneath. To form a uniform circular first or base layer of stabilized granular agglomerate, the openings 592 in the shield 590 are open circles, the openings 592 spaced apart in a selected pattern in the planar material 591, defined by rims 593 as shown in FIG. 69. The shield 590 can be placed directly above, or alternatively spaced a suitable distance above, the upper surface 725 of the thermofusable powder layer 724. It should be understood that the segment illustration shown in step A-3 extends across the entire build module.

After positioning of the shield 590, laser light 721 is emitted from light-emitting elements 723 of an energy source 722 as illustrated in step A-4 of FIG. 67. The areal shape and pattern of the light-emitting elements 723 can be placed on the undersurface of the energy source 722 in the same shape as the removable build plate 706 of the build module 700, so that the entire surface of the removable build plate 706 and uniform thermofusable powder layer 724 are exposed to the emitted heat energy simultaneously. In an alternative embodiment, a laser light heat source can have a smaller area of light emission that can be maneuvered laterally above the shield 590 to expose the removable build plate 706 and uniform thermofusable powder layer 724 in a predetermined duration and pattern of heat energy. The laser light energy passing through the openings 592 in the shield 590 strikes the exposed portions 726 of the upper surface 725 of the thermofusable powder layer 724, to heat the thermofusable powder material beneath the exposed surface 726, which causes the thermal binder material within the thermofusable powder material to soften and/or melt sufficiently. The energy intensity and duration can be selected to provide sufficient softening and melting of the thermal binder material in the exposed surface portions 726, while avoiding complete liquifying of the thermal binder material, while the shield 590 prevents or minimizes heating, and bonding or agglomeration, of the thermofusable powder material 724 in the shielded surface portions 727. It should be understood that the segment illustration shown in step A-4 extends across the entire build module.

After the heat energy is stopped or removed, the shield 590 is removed from over the upper surface 725, revealing a selectively thermofused first layer or base layer 775, as shown in step A-5 of FIG. 67. As the exposed heated powder material cools, the thermofusable powder material beneath the exposed surface 726 has become bonded together into stabilized granular agglomerate, forming the thermofused base portions 734 of the container article, while the thermofusable powder material in the shielded portions 727 remains unbonded and free-flowing. Each of the patterned areas of bound powder corresponds to an area and thickness of a circular base for a dosage form, such as circular base 3 shown in FIG. 1. It should be understood that the segment illustration shown in step A-5 extends across the entire build module.

In some embodiments, the process of Steps A-1 through A-5 can be repeated in series, one or more additional times, to form a plurality of thicker, two- (or more-) layered circular base for a container body. A second layer of thermofusable powder material is deposited over the selectively-bonded first layer 775, and the shield 590 positioned with the openings 592 in registry with the stabilized granular agglomerate 734 of the first layer 775. The powder material exposed through the openings 592 is thermally fused and bonded by the heat energy of the laser light into a newly-formed stabilized granular agglomerate, which also bonds to the stabilized granular agglomerate 734 therebelow of the selectively-thermofused first layer 775.

In step B-1 shown in FIG. 68, the upper surface 706a of the removable build plate 706 is again lowered by an increment distance within the build module 700, re-forming a cavity 703 above the upper surface of the selectively-bound powder layer(s) 514.

In process step B-2 of FIG. 68, another substantially uniform layer of thermofusable powder 754 is deposited within the cavity 703, and its upper surface 755 made level with (at the same height of) the position of the upper surface 701a of the build module.

In process step B-3 of FIG. 68, a second shield 595 is positioned above the upper surface 755 of the second thermofusable powder layer 754. The shield 595 is similar to the material and construction of the first shield 590 described above, though having different openings formed through the planar material to expose the thermofusable powder layer below to a different pattern laser light. The second shield 595 is placed above and substantially parallel to the upper surface 755 of the second thermofusable powder layer 754. To form a plurality of an annular wall portions onto the first or base layers 734 the thermofused first layer 775, the openings in the shield 595 is a substantially complete annular space 596 defined between the circular rims 598 and interior, central portions 597 that can be joined to the rim 598 by thin connectors 599, as shown in FIG. 70. The thin connectors are sufficiently narrow that they do not substantially interfere with the heating of the thermofusable powder material. The openings 596 are spaced apart in a selected pattern in the planar material, as shown in FIG. 70, such that when the shield 595 is placed directly above, or alternatively spaced a suitable distance above, the upper surface 755 of the second powder layer 754, the openings 596 register with the peripheries of the stabilized granular agglomerate that forms the base layers 734 in selectively thermofused first layer 755. It should be understood that the segment illustration shown in step B-3 of FIG. 68 can extend across the entire build module.

After positioning of the shield 595, laser light 721 is emitted from light-emitting elements 723 of an energy source 722 as illustrated in step B-4. The laser light energy passing through the openings 596 in the shield 595 strikes the exposed portions 757 of the upper surface 755 of the second thermofusable powder layer 754, to heat the thermofusable powder material beneath the exposed surface 757, which causes the thermal binder material within the thermofusable powder material to soften and/or melt sufficiently. The energy intensity and duration can be selected to provide sufficient softening and melting of the thermal binder material in the exposed surface portions 757, while avoiding complete liquifying of the thermal binder material. The shield 595 prevents or minimizes heating, and bonding or agglomeration, of the thermofusable powder material 754 in the shielded surface portions 758 and 759, and will remain an unbonded and unfused powder material. It should be understood that the segment illustration shown in step B-4 extends across the entire build module.

After the heat energy is stopped or removed, the shield 595 is removed from over the upper surface 755, revealing a selectively thermofused second layer 776, as shown in step B-5. As the exposed heated powder material cools, the thermofusable powder material beneath the exposed surface 757 has bonded together into stabilized granular agglomerate, forming the thermofused second layer portions 736 that form the first layer of the peripheral wall of the container article. Each of the patterned areas 736 of bound powder correspond to an area and thickness of the peripheral wall for a dosage form, such as peripheral wall 6 shown in FIG. 1, while the thermofusable powder material 754 in the shielded portions 758 and 759 remain unbonded and free-flowing. It should be understood that the segment illustration shown in step B-5 extends across the entire build module.

In some embodiments, the process of steps B-1 to B-5 of FIG. 68 are repeated in series, one or more additional times, to form a peripheral container wall consisting of two or more layers of the stabilized granular agglomerate, typically using the same thermofusable powder material, shield 595 and heat source.

The thermofusing of the annular walls layers completes a container body, such as peripheral wall 92 shown in FIG. 11. In some embodiments, the thermofusing process can be stopped and the thermofused container bodies removed from the build module and the removable build plate, and separated from any unbound powder material.

In some embodiments, any unbound thermofusable powder material that remains positioned between the outer surfaces of the formed container bodies, or within the cavity of the container bodies, can be evacuated, using the means described and illustrated herein, for example, at FIGS. 10-12 when forming separate-cavitied container bodies, or for example at FIG. 44 when forming a unitary, medicament-filled containers.

In the illustrated embodiment, a plurality of container bodies are being formed within an open print bed. However, the person of ordinary skill understands that the steps of depositing a layer of thermofusable powder material, positioning a shield over the upper surface of the powder layer, and directing heat energy through the one or more openings in the shield to selectively bond the thermofusable powder material into a stabilized granular agglomerate, can be performed within a depression or pocket of a packaging material, such as a blister.

In another embodiment, said means can comprise a heat source that passes heat energy into the layer of thermofusable powder material through the outer wall and/or base of a forming mold or blister package in which the dosage form is being formed in situ, which heats the thermofusable powder material only around the periphery of the layer of powder material, and thus limiting the penetration of heat energy into the interior portions of the powder layer. A non-limiting example of such targeting heat energy can include a conductive heat source. The rate and total amount of heat energy transferred through the outer wall and/or base of a forming mold or blister package can be controlled to effect a raising of the temperature of the thermofusable powder material in the peripheral portions adjacent to the outer wall and/or base to a bulk temperature at or above the glass transition temperature of the thermal binder, to softener and/or melt the thermal binder material only in such peripheral portions to bond the other particulate components into a bonded matrix. The interior portion of the layer of thermofusable powder material, spaced a distance away from the outer wall and/or base, may be unheated or be limitedly heated such that the bulk temperature in the interior portion of the layer of thermofusable powder material remains below the glass transition temperature of the thermal binder, such that the particles of thermal binder material and the other particulate other particulate components remain solid, unbound, and un-agglomerated.

Upon cutting off of the heat transfer through the outer wall and/or base, and/or extracting heat through the outer wall and/or base by cooling thereof, the bulk temperature drops below the glass transition temperature of the thermal binder, such that thermal binder material re-solidifies to form a stabilized granular agglomerate in the peripheral portions of the layer. After sufficient cooling of the layer to ambient temperatures, the thermal binder material hardens to form a stable granular agglomerate.

After the thermal binder has been heated to a temperature that softens and/or melts the thermal binder and binds the other particulate components, the molten thermal binder material is cooled. The time and cooling medium temperature are such as to solidify the melted or softened thermal binder. Typically, the cooling medium is a gas, for example, air, nitrogen, carbon dioxide, or other inert. In one embodiment, the target cooling medium temperature is about 25° C. to about 0° C., and the time of cooling is about 10 to about 60 seconds. Generally, the higher the cooling medium temperature during cooling, the longer the cooling time. In one embodiment the cooling takes place at room temperature (25° C.) for greater than 5 minutes.

In some embodiments, a means for heating the layer or layers of powder material to a staging temperature that is below, though typically close to, the glass transition temperature of the thermal binding material. At the staging temperature, the thermal binder material and the other particulate components remain solid and free-flowing. By raising the temperature of thermofusable powder material to the staging temperature, the intensity and duration of heat applied by the laser light heat source can be minimized when the heat source is directed at the pre-selected surface area of the layer of thermofusable powder material. As a result, the temperature of the thermofusable powder layer can more efficiently be raised only at pre-selected portions of the surface area to approach an activating temperature near, at or above the glass transition temperature of a thermal binder, while the portions that are not selected or targeted for heating remain at, or near to, the staging temperature, and below the glass transition temperature of the thermal binding material contained therein. Upon reaching the activation temperature, the activated thermal binder can begin to soften, melt, and cohesively bind to adjacent particulate components in the thermofusable powder material that remain solid, in order to form a bound matrix. In some embodiments, the bulk thermofusable powder material is stored at the staging temperature, and deposited into the layer of powder material at the staging temperature. In some embodiments, the bulk thermofusable powder material is heated to the staging temperature during its transfer from its storage to its depositing into the layer of powder material. In some embodiments, the thermofusable powder material is heated to the staging temperature as or after it has been formed into the layer of powder material, and before activating or targeting of the selected portions of the powder layer with heat energy.

The bound matrix formed by heating a thermofusable powder material is capable of rapid dissolution upon contact with an aqueous liquid, including rapid orodispersibility, under the same conditions and to the same extend as a bound matrix described herein that is formed by depositing and/or forming a layer of powder material and wetting with a binding liquid.

In another embodiment, rapidly-orodispersible dosage forms of the present invention can be characterized by their overall hardness and friability characteristics. In another embodiment, the hardness of the matrix can be the same (uniform) throughout the matrix. In another embodiment, hardness of the matrix can vary within the same matrix. In another embodiment, a container body can have a hardness that is within +/−10% of the hardness of the container body within the same dosage form. In another embodiment, the container body and the lidding body in the same dosage form have the same hardness. In some embodiments, the hardness of one portion of the dosage form can be greater than the hardness of another portion of the dosage form. In a non-limiting example, and in another embodiment, the one or more base layers of the dosage form can have a hardness that is greater than the layers comprising the peripheral wall and/or the upper portion of the dosage form, to provide additional protection against dropping the dosage form. In another embodiment, the hardness of the base portion of the dosage form can be at least 1.05-fold, at least 1.1-fold, at least 1.2-fold, at least 1.3-fold, at least 1.4-fold, at least 1.5-fold, at least 1.75-fold, at least 2-fold, at least 2.5-fold, at least 3-fold, at least 5-fold, at least 7-fold, or at least 10-fold higher than other portions of the dosage form.

In another embodiment, some embodiments, the dosage form has an overall hardness that gives the dosage form a shelf life of at least six months. In another embodiment, some embodiments, the dosage form has an overall hardness that gives the dosage form a shelf life of at least one year. In another embodiment, rapidly-orodispersible container and/or lidding bodies stored separately from each other have a shelf life of greater than one year.

In another embodiment, the overall hardness (as determined by a tablet breaking force assay according to USP<1217>) of rapidly-orodispersible dosage form, rapidly-orodispersible container, and/or rapidly-orodispersible lidding body can be in a range selected from the group consisting of: from at least about 1 kp, up to about 20 kp; from at least about 1 kp, up to about 10 kp; from at least about 1 kp, up to about 7 kp; from at least about 3 kp, up to about 9 kp; from at least about 1 kp, up to about 3 kp; from at least about 4.5 kp, up to about 6 kp; from at least about 2.5 kp, up to about 6.5 kp; from at least about 3 kp, up to about 6 kp; or from at least about 1 kp, up to about 5 kp. In another embodiment, the overall hardness of the rapidly-orodispersible dosage form, container body, and/or lidding body is at least 1 kp, or at least 2 kp, or at least 3 kp. In another embodiment, the overall hardness of the rapidly-orodispersible dosage form, container body, and/or lidding body is no more than 10 kp, or no more than 8 kp, or no more than 6 kp.

The friability of the rapidly-orodispersible dosage form, container body, or lidding body refers to the tendency of the bound-powder matrix to lose material from its outer edges and surfaces upon manipulation or handling. As the hardness of the object is increased, the friability is reduced. In another embodiment, the rapidly-orodispersible dosage form, container body, or lidding body can possess a friability of less than about 25%, and is preferably less than about 10%, as determined according to USP chapter <1216>.

An article of the present invention shall have sufficient integrity to allow for packaging, storage, and transportation of the article to a user, as well as sufficient integrity while opening of its packaging and administering to the user or third person. In some embodiments, an article comprising a container body and lidding body shall have a sufficient level of fixation or securement between the container body and the lidding body, whether by an adhesive securement or a mechanical securement, or a combination thereof, such that the article may be inverted without separation of the lidding body from the container body, or without loss or spillage of any contents contained within the article, such as a particulate material or medicament housed contained within the article. In some embodiments the strength of fixation between container body and lidding body is sufficient to sustain the suspended weight of the lidding body, container body, and/or any contents of the article without failure. In some embodiments, the fixation of the lidding body to the container body is sufficient to bear a tensile load greater than or equal to 0.005N, greater than or equal to 0.01N, greater than or equal to 0.02N, greater than or equal to 0.05N, or greater than or equal to 0.1N, without failure. In some embodiments, an article of the present invention tested for tablet hardness (i.e., tablet breaking force, USP<1217>) exhibits a hardness of greater than 0.5 kp, greater than 1.0 kp, greater than 1.5 kp, greater than 2.0 kp, greater than 3.0 kp, greater than 4.0 kp, greater than 5.0 kp, or greater than 10.0 kp. In some embodiments, an article of the present invention can sustain both the tensile loads and the compressive loads (breaking force) as described above, or elsewhere herein, alone or in combination with other features of the present invention.

In another embodiment, the porosity of the bound-powder matrix comprising the rapidly-orodispersible dosage form, container body, or lidding body can be in a range from at least about 10%, up to about 90%; or from at least about 30%, up to about 70%, of the overall volume of the matrix. In another embodiment, the bulk density of the bound-powder matrix (as determined by measurement and/or calculation) can be in a range from at least about 150 mg/mL, up to about 1300 mg/mL; or from at least about 400 (mg/mL), up to about 1000 (mg/mL).

In another embodiment, the dissolution time of the one or more medicaments is slower than, and independent of, the dispersion time of the rapidly-orodispersible dosage form itself when placed in an aqueous fluid. In another embodiment, rapid dissolution of the medicament(s) can be achieved, wherein not less than 75% by weight (or wherein at least 75% by weight) of the one or more medicaments contained within the rapidly-orodispersible dosage form dissolves in a time selected from the group consisting of: 20 minutes or less; 10 minutes or less; 5 minutes or less; 4 minutes or less; 3 minutes or less; 2 minutes or less; or 1 minute or less, when placed in an aqueous environment, such as, in a non-limiting example, within a subject's digestive tract. In another embodiment, not less than 95% by weight (or at least 95% by weight) of the one or more medicaments contained within the rapidly-orodispersible dosage form dissolves in a time selected from the group consisting of: 20 minutes or less; 10 minutes or less; 5 minutes or less; 4 minutes or less; 3 minutes or less; 2 minutes or less; or 1 minute or less, when placed in an aqueous environment.

In an alternative embodiment, controlled release of the medicaments can be achieved, in which only a small portion of the medicament(s) dissolves within a given time period. In a non-limiting example, and in another embodiment, not more than 50% by weight (or wherein less than 50% by weight), of the one or more medicaments contained within the rapidly-orodispersible dosage form dissolves in a time selected from the group consisting of: 20 minutes or less; 10 minutes or less; 5 minutes or less; 4 minutes or less; 3 minutes or less; 2 minutes or less; or 1 minute or less, when placed in an aqueous environment. In another embodiment, not more than 10% by weight, (or wherein less than 10% by weight), of the one or more medicaments contained within the rapidly-orodispersible dosage form dissolves in a time selected from the group consisting of: 20 minutes or less; 10 minutes or less; 5 minutes or less; 4 minutes or less; 3 minutes or less; 2 minutes or less; or 1 minute or less, when placed in an aqueous environment.

In another embodiment, the controlled dissolution of the one or more medicaments can alternatively be defined by the mass percent of the medicament(s) dissolved within an aqueous fluid in a specified time. In another embodiment, the mass percent of the one or more medicaments that are dissolved 10 minutes after placing a rapidly-orodispersible dosage form in the aqueous fluid can be a value selected from the group consisting of: less than 50% by weight; less than 45% by weight; less than 40% by weight; less than 35% by weight; less than 30% by weight; less than 25% by weight; less than 20% by weight; less than 15% by weight; less than 10% by weight; less than 5% by weight; and less than 1% by weight. In another embodiment, less than 40% by weight of the one or more medicaments is dissolved 10 minutes after placing the rapidly-orodispersible dosage form in an aqueous fluid. In another embodiment, less than 30% by weight of the one or more medicaments is dissolved 10 minutes after placing the rapidly-orodispersible dosage form in an aqueous fluid.

In another embodiment, the mass percent of the one or more medicaments that are dissolved 2 minutes after placing a rapidly-orodispersible dosage form in the aqueous fluid can be a value selected from the group consisting of: less than 20% by weight; less than 15% by weight; less than 10% by weight; less than 8% by weight; less than 6% by weight; less than 5% by weight; less than 4% by weight; less than 3% by weight; less than 2% by weight; and less than 1% by weight. In another embodiment, less than 8% by weight of the one or more medicaments is dissolved 2 minutes after placing the rapidly-orodispersible dosage form in an aqueous fluid. In another embodiment, less than 4% of the one or more medicaments is dissolved 2 minutes after placing the rapidly-orodispersible dosage form in an aqueous fluid.

In some embodiments, any of the dissolution times above may be achieved in aqueous environments characterized by a pH of 1.2 or 4.5 or 6.8, and tested within a USP paddle apparatus at 50 RPM or 75 RPM or 100 RPM and a volume of 900 mL or 950 mL or 1000 mL.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

EXAMPLES

The following working and prophetic examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Preparation of a Unitary Rapidly-Orodispersible Dosage Form Having a Medicament Contained within an Internal Cavity The following materials and process was used to prepare a three-dimensionally printed, unitary rapidly-orodispersible dosage form having a medicament contained within an internal cavity. A plurality of tablets were formed within a series of pre-formed, thermoformed blister depressions. The ingredients for the printing fluid and the powders used, as well as the build sequence, are indicated below:

TABLE 1

| Printing Fluid Component | % w/w |
|---|---|
| 25 mM Phosphate Buffered Solution | 72.0 |
| Polysorbate 20 | 1.90 |
| Isopropyl Alcohol | 12.3 |
| Glycerin | 3.80 |
| Povidone K29/32 | 10.00 |
| Total | 100 |

TABLE 2

| Powder 1 Component | % w/w |
|---|---|
| Mannitol 50C | 42.5 |
| Mannitol 160C | 42.5 |
| Avicel PH101 | 7.0 |
| Povidone K29/32 | 7.0 |
| Cab-O-Sil | 1.0 |
| Total | 100 |

TABLE 3

| Medicament Powder | % w/w |
|---|---|
| Compound A with Tastemask Coating | 100 |
| Total | 100 |

TABLE 4

| | | Build Sequence |
|---|---|---|
| Sequence # | Step | Conditions |
| 1 | Print 2 layers | Printing fluid, 1800 DPI, 17.2 mm Circle pattern |
| 2 | Dispense and level | Powder 1, ~175 mg |
| 3 | Print 2 layers | Printing fluid, 1800 DPI, 17.5 mm, 1.5 mm Ring pattern |
| 4 | Dispense and level | Powder 1, ~175 mg |
| 5 | Print 2 layers | Printing fluid, 1800 DPI, 17.8 mm, 1.5 mm Ring pattern |
| 6 | Dispense and level | Powder 1, ~175 mg |
| 7 | Print 2 layers | Printing fluid, 1800 DPI, 18.1 mm, 1.5 mm Ring pattern |
| 8 | Dispense and level | Powder 1, ~175 mg |
| 9 | Print 2 layers | Printing fluid, 1800 DPI, 18.4 mm, 1.5 mm Ring pattern |
| 10 | Dispense and level | Powder 1, ~175 mg |
| 11 | Print 2 layers | Printing fluid, 1800 DPI, 18.8 mm, 1.5 mm Ring pattern |
| 12 | | Vacuum loose Powder 1 from center |
| 13 | Dispense and level | Medicament Powder, 200 mg |
| 14 | Dispense and level | Powder 1, ~175 mg |
| 15 | Print 2 layers | Printing fluid, 1800 DPI, 18.8 mm, 1.5 mm Ring pattern |

TABLE 4-continued

Build Sequence

| Sequence # | Step | Conditions |
| --- | --- | --- |
| 16 | Dispense and level | Powder 1, ~175 mg |
| 17 | Tamp | 3.0 mm, Flat |
| 18 | Print 4 Layers | Printing fluid, 900 DPI, 19.2 mm, Circle pattern |

The formed tablet within the blister depression was then air dried. Tablet hardness ranged from 1.4 to 3.4 kp. Oral disintegration time of the tablet ranged from 6.8 to 27.0 seconds.

Example 2: Preparation of a Two-Piece Rapidly-Orodispersible Placebo Dosage Form Having a Solid Payload Material Contained within an Internal Cavity Three-dimensionally printed, rapidly-orodispersible dosage forms having a solid material contained within an internal cavity were prepared. A plurality of dosage forms were produced in an open body within a build module, using the procedures described in U.S. Pat. No. 8,888,480. Each dosage form was assembled from two pieces—a container body and a lidding body which were secured together by the application of the adhesive fluid. Container bodies were formed separately from lidding bodies. The powder material was the same Powder 1 used in Example 1. The components of the printing fluid and the adhesive fluid are indicated below:

TABLE 5

| Printing Fluid Component | % w/w |
| --- | --- |
| Water | 72.0 |
| Polysorbate 20 | 1.90 |
| Isopropyl Alcohol | 12.3 |
| Glycerin | 3.80 |
| Povidone K29/32 | 10.00 |
| Total | 100 |

TABLE 6

| Adhesive Fluid Component | % w/w |
| --- | --- |
| Water | 42.5 |
| Isopropyl Alcohol | 42.5 |
| Hydroxypropyl Cellulose | 15.0 |
| Total | 100 |

The plurality of container bodies were formed using a similar build sequence as described above in Example 1, with the formation of a solid base layer, followed by a plurality of incremental intermediate layers printed in a ring pattern to form the peripheral wall of the container body. The pattern of printing fluid applied to the uppermost layer of the peripheral wall was adjusted to form a pair of congruently-shaped slots into opposite sides of the peripheral wall's upper surface, substantially as illustrated in FIG. 35. Each lidding body was formed using a similar procedure to the base layer of the container body, except that a pair of rectangularly-shaped pins were formed to extend from opposite sides of an outer surface of the peripheral edge of the lidding body, also as shown in FIG. 35.

Once formed, lidding bodies and container bodies were dried in a convection oven at 60° C. and were separated from loose unprinted powder with vacuum and compressed air. The central cavities of each container body were partially filled with Powder 1 as a placebo material and leveled, until the depth of the powder material below the upper surface of the peripheral was approximately the same as the thickness of the lidding body. Instead of using Powder 1 as a placebo material, a medicament, such as the medicament in Example 1, can be used to fill the cavity. Lidding bodies were adhered to the container body using the adhesive fluid, with the lidding body pins in register with the slots formed into the container body, to produce the dosage form substantially as illustrated in FIG. 36. All of the dosage forms were dried overnight in ambient conditions.

The hardness of the dosage forms ranged from 3.6 to 7.5 kp and their disintegration time ranged from 3 to 17 seconds.

Example 3: Preparation of a Unitary Rapidly-Orodispersible Dosage Form Having a Solid Payload Contained within an Internal Cavity The following materials and process are used to prepare three-dimensionally printed, rapidly-orodispersible dosage forms having a solid payload contained within an internal cavity. The ingredients for the printing fluid and the powders are indicated below:

TABLE 7

| Printing Fluid Component | I-A | | I-B | | I-C | | I-D | | I-E | |
| --- | --- | --- | --- | --- | --- | --- | --- | --- | --- | --- |
| (% w/w) | Low | High | Low | High | Low | High | Low | High | Low | High |
| Water | 65 | 75 | | | 65 | 75 | 65 | 75 | 65 | 75 |
| 25mM Phosphate Buffered Solution | | | 65 | 75 | | | | | | |
| Polysorbate 20 | 1.5 | 2.5 | 1.5 | 2.5 | 1.5 | 2.5 | 1.5 | 2.5 | 1.5 | 2.5 |
| Isopropyl Alcohol | 10 | 15 | 10 | 15 | 10 | 15 | 10 | 15 | | |
| Ethanol | | | | | | | | | 10 | 15 |
| Glycerin | 3.5 | 4.5 | 3.5 | 4.5 | 3.5 | 4.5 | 3.5 | 4.5 | 3.5 | 4.5 |

TABLE 7-continued

| Printing Fluid Component (% w/w) | I-A Low | I-A High | I-B Low | I-B High | I-C Low | I-C High | I-D Low | I-D High | I-E Low | I-E High |
|---|---|---|---|---|---|---|---|---|---|---|
| Povidone K29/32 | 8.5 | 10.5 | 8.5 | 10.5 | | | 8.5 | 10.5 | 8.5 | 10.5 |
| Copovidone | | | | | 8.5 | 10.5 | | | | |
| Sucralose | | | | | | | | 5 | | |
| Total | 88.5 | 107.5 | 88.5 | 107.5 | 88.5 | 107.5 | 88.5 | 112.5 | 88.5 | 107.5 |

TABLE 8

| Powder 1 Component (% w/w) | II-A Low | II-A High | II-B Low | II-B High | II-C Low | II-C High | II-D Low | II-D High | II-E Low | II-E High |
|---|---|---|---|---|---|---|---|---|---|---|
| Mannitol | 80 | 90 | | | 60 | 80 | 60 | 80 | | |
| Lactose | | | 60 | 80 | | | | | 60 | 80 |
| Microcrystalline Cellulose | 5 | 10 | 10 | 20 | 10 | 20 | 5 | 15 | 5 | 15 |
| Povidone K29/32 | 5 | 10 | 10 | 20 | | | 5 | 15 | 5 | 15 |
| Copovidone | | | | | 5 | 25 | | | | |
| Starch | | | | | | | 5 | 15 | 5 | 15 |
| Colloidal Silica | | 2 | | 2 | | 2 | | 2 | | 2 |
| Total | 90 | 112 | 80 | 122 | 75 | 127 | 75 | 127 | 75 | 127 |

A predetermined mass or volume of Powder 1 is dosed into a preformed blister cavity and leveled to form an incremental layer having a substantially uniform thickness. Printing fluid is applied to the incremental layer as droplets according to a pre-determined shape pattern, saturation level, line spacing and printing fluid flow rate to bind the particles therein. A base is formed by applying printing fluid to substantially all of the surface area of one or more incremental layers to form a bound matrix. Peripheral walls are formed atop and bound to the base by applying printing fluid only to a perimeter portion of one or more incremental intermediate layers, while leaving a central portion of each intermediate layer unbound. Any of Printing Fluids I-A through I-E are used. Any of the Powder 1 II-A through II-E are used. Some dosage forms comprise a single Printing Fluid I-A through I-E and a single Powder 1 II-A through II-E.

The process is repeated until a container is formed having a base and a peripheral wall extending from the base. Loose, unbound Powder 1 within the container portion is removed by vacuum or compressed air. Medicament powder III-A through III-E are placed and leveled in the container shape using volumetric or gravimetric dosing means. Powder 1 and Printing Fluid are then applied to the shared surface formed by the Medicament Powder and upper surface of the peripheral wall, using a similar procedure as used to form the base, above, to enclose the Medicament Powder and build an upper matrix portion of the dosage form. The resulting unitary 3DP rapidly-orodispersible dosage form is dried by any suitable means to reduce the amount of solvent and moisture to a desired level.

TABLE 9

| Medicament Powder (% w/w) | II-A Low | II-A High | II-B Low | II-B High | II-C Low | II-C High | II-D Low | II-D High | II-E Low | II-E High |
|---|---|---|---|---|---|---|---|---|---|---|
| Compound A with Tastemask Coating | 80 | 100 | | | | | | | 40 | 50 |
| Compound B with Extended Release Coating | | | 80 | 100 | | | | | 40 | 50 |
| Compound C Granule with Solubility Enhancer | | | | | 80 | 100 | | | | |
| Compound D Granule with Permeability Enhancer | | | | | | | 80 | 100 | | |
| Microcrystalline Cellulose | 0 | 20 | 0 | 20 | 0 | 20 | 0 | 20 | 0 | 20 |
| Crospovidone | 0 | 10 | 0 | 10 | 0 | 10 | 0 | 10 | 0 | 10 |
| Sodium Starch Glycolate | 0 | 10 | 0 | 10 | 0 | 10 | 0 | 10 | 0 | 10 |
| Colloidal Silica | 0 | 2 | 0 | 2 | 0 | 2 | 0 | 2 | 0 | 2 |
| Total | 80 | 142 | 80 | 142 | 80 | 142 | 80 | 142 | 80 | 142 |

In an alternative to filling the central cavity with any of the Medicament Powders III-A through III-E, any solid material can instead be utilized, for example, any of the Powder 1 materials II-A through II-E.

Example 4: Preparation of a Two-Piece Rapidly-Orodispersible Dosage Form Having a Solid Payload Contained within an Internal Cavity The following materials and process are used to prepare three-dimensionally printed, rapidly-orodispersible dosage forms having a solid payload contained within an internal cavity. Any of the Printing Fluids I-A through I-E, Powder 1 materials II-A through II-E, or Medicament Powders III-A through III-E described in Example 3 above can be utilized.

A container body, comprising a base portion and a peripheral wall, can be formed using the procedures described in U.S. Pat. No. 8,888,480 and/or in Example 2 above. A lidding body is formed separately using similar procedures as for the container body, and comprising either an identical powder composition or a different powder composition relative to the container body. The lidding body is formed to have a complementary shape to the upper surface of the container, such that the central cavity of the container can be enclosed by the lidding body upon assembly.

The container body and lidding body are dried by any suitable means to reduce the amount of solvent and moisture to a desired level and are separated from loose unprinted powder with vacuum or compressed air. The dosage form is assembled by filling the central cavity of the container with any of the Medicament Powders III-A through III-E above, with any of the Powder 1 materials II-A through II-E, or other solid material. The lidding body is placed atop the filled container and adhered, fixed, or otherwise secured to the container body by mechanical locking, or application of a polymer solution or low-melting material as an adhesive. If polymer solution is used, the resulting two-piece 3DP rapidly-orodispersible dosage form is dried by any suitable means to reduce the amount of solvent and moisture to a desired level.

Example 5: Characterization of Dosage Forms

The following procedures are used to characterize the three-dimensionally printed rapidly-orodispersible dosage forms Surface Texture and Visual Inspection The dosage forms are inspected visually with or without the aid of a microscope. The surface texture is analyzed to determine if it is rough or smooth and whether the edges of indicia on the upper surface and the edges of the perimeter of the wafer are clean and sharp or rough and jagged.

Hardness

The dosage forms are analyzed for overall hardness as determined by a tablet breaking force assay according to USP<1217> (31st edition) using a VK 200 tablet hardness tester (Varian, US). The strength or hardness is measured by a fracture test, in which a dosage form is centered between the jaws of the tester and force is applied until the dosage form fractures. The load at fracture is returned in kilogram-force, or kiloponds (kp). A kilopond is a metric unit of force measurement with 1 kp being equivalent to 9.807 Newtons. A minimum number of 6 dosage forms are tested. The hardness of the dosage forms ranges from about 0.5 kp to about 3.0 kp.

Dispersion Time

The dosage forms are analyzed for dispersion time in aqueous fluid according to protocols set forth within USP<701>, using a basket-rack assembly to immerse one or more tablet into a liquid, preferably water. An uncoated or plain-coated tablet is placed into a receptacle or tube within the basket, and the basket immersed into the immersion liquid, which is maintained at 37+/−2° C. Tablets containing a delayed- or extended-release coating are immersed into a fluid that simulates physiological conditions within the stomach or intestines, depending on the desired release location.

The dispersion time for the dosage forms range from 7 seconds to 27 seconds.

Bulk Density

The bulk density of the matrix is determined by measuring the weight of the dosage form and dividing that value by the calculated volume of the dosage form. The volume is calculated by measuring the dosage form's dimensions and using the proper mathematical formula according to the shape of the dosage form. For example, for a frustoconical dosage form, the volume of which is calculated using the form $\pi*r^2*H$, wherein r is the average radius of the top and bottom surfaces of the dosage form and H is its height. Accordingly, a dosage form weighing 1.05 g, having a height of 0.537 cm and an average radius of 0.782 cm, has a volume of about 1.032 cm$^3$, and a bulk density of about 1.021 g/cm$^3$, which is equivalent to about 1021 mg/ml.

Dissolution of the API

Dissolution testing is conducted according to the Guidance for Industry (See Section 3.3.2; Waiver of In Vivo Bioavailability and Bioequivalence Studies for Immediate-Release Solid Oral Dosage Forms Based on a Biopharmaceutics Classification System. August 2000. Section Inc, p 7). The method of USP<711> was followed. Dissolution is performed using a USP Apparatus II (paddle) at 100 rpm using 900 mL of the following de-aerated dissolution media: simulated saliva (10 mM sodium phosphate, 15 mM sodium chloride, pH 6.5 buffer at 37° C. 1.7% of the Compound A was released after 2 minutes.

Because the instant application is a continuation application, to the extent any amendments, characterizations, or other assertions previously made (in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A rapidly-orodispersible dosage container form, comprising:
a porous, durable container body comprising a first bound-powder material comprising an interconnected matrix of a first ingestible powder material and a first ingestible binder material, the container body comprising a base and a peripheral wall extending from the base, the peripheral wall having an inner surface, an upper surface, and an external surface, and the container body having one or more empty cavities bounded by the base and the inner surface of the peripheral wall;
a porous, durable lidding body comprising a second bound-powder material comprising an interconnected matrix of a second ingestible powder material and second ingestible binder material, the porous lidding body having an undersurface configured to be positioned over the upper surface of the peripheral wall, the lidding body configured to cover the one or more empty cavities and form one or more interior cavities; and a means for securing the lidding body to the peripheral wall, wherein the first ingestible powder material and the second ingestible powder material comprise independently one or more pharmaceutical excipients selected from the group consisting of a solid binder material, a disintegration agent, a dispersant, a sweetener, a glidant, a flavoring agent, a surfactant, a humectant, a preservative, an antioxidant, a solvent, a diluent, and combinations thereof; and the first ingestible binder material and the second ingestible binder material are independently selected from the group consisting of a water-soluble synthetic polymer, polyvinyl pyrrolidone, lactitol, erythritol, pregelatinized starch, modified starch, hydroxypropylmethylcellulose, spray dried lactose, fructose, sucrose, dextrose, sorbitol, mannitol, and xylitol, and combinations thereof.

2. The dosage container form according to claim 1, wherein the one or more interior cavities formed when the porous lidding body covers the one or more empty cavities has a volume that is at least 5% of a volume of the dosage container form.

3. A filled-and-sealed dosage form comprising the rapidly-orodispersible dosage container form according to claim 2 and one or more particulate medicaments that are isolated within the one or more interior cavities, wherein the one or more particulate medicaments have a mass of at least 1 milligram, and up to 10 grams.

4. The filled-and-sealed dosage form according to claim 3, further comprising a dissolvable barrier material, coated onto at least a portion of an interior surface that forms a boundary for the one or more interior cavities.

5. The filled-and-sealed dosage form according to claim 4, wherein the dissolvable barrier material is disposed between the one or more particulate medicaments and the first bound-powder material.

6. The dosage container form according to claim 1, wherein the means for securing comprises an adhesive material applied to at least one of (i) a portion of either or both of the undersurface of the lidding body and the upper surface of the peripheral wall, and (ii) a portion of either or both of an inner surface of a perimeter wall of the lidding body and the external surface of the peripheral wall of the container body.

7. The dosage container form according to claim 6, wherein the adhesive material is selected from the group consisting of mannitol, sorbitol, xylitol, lactitol, erythritol, isomalt, povidone, copovidone, hydroxypropylcellulose, hydroxypropylmethylcellulose, carboxymethylcellulose, gelatin, casein, agar, guar gum, gellan gum, xanthan gum, locust bean gum, alginate, carrageenan, hydroxypropyl starch, pre-gelatinized starch, poloxamer, polyethylene glycol, polydextrose, polyvinyl alcohol, and combinations thereof.

8. The dosage container form according to claim 1, wherein the means for securing comprises a first mechanical securement on the upper surface of the peripheral wall and a second mechanical securement on the lidding body, wherein the mating of the first mechanical securement and the second mechanical securement with each other mechanically secures the lidding body to the container body.

9. The dosage container form according to claim 8 wherein the second mechanical securement is on the undersurface of the lidding body.

10. The dosage container form according to claim 8, wherein (i) the first mechanical securement comprises one or more valleys formed into the peripheral portion of the upper surface of the peripheral wall, the second mechanical securement comprises one or more peaks formed upon the peripheral portion of the undersurface of the lidding body, and the one or more peaks of the lidding body are in register with and secured to the one or more valleys of the container body; (ii) the lidding body has a perimeter wall extending from the peripheral portion of the undersurface, the perimeter wall having a bottom surface and an inner surface, wherein the inner surface of the perimeter wall of the lidding body is frictionally engaged with at least a portion of the external surface of the peripheral wall of the container body, or (iii) the dosage form has a planar bottom surface, defined by the base of the container body and the bottom surface of the perimeter wall of the lidding body.

11. The dosage container form according to claim 1, wherein the peripheral wall has a thickness of at least 1.0 mm, and up to 5.0 mm.

12. The dosage container form according to claim 11, wherein the peripheral wall has a substantially uniform thickness of at least 1.5 mm, and up to 3.0 mm.

13. The dosage container form according to claim 1 wherein the disintegration agent is selected from the group consisting of microcrystalline cellulose, crospovidone, croscarmellose, sodium starch glycolate, and a combination thereof.

14. The dosage container form according to claim 1 wherein the one or more pharmaceutical excipients is selected from the group consisting of a solid binder material, a disintegration agent, a dispersant, a sweetener, a glidant, a surfactant, a humectant, a preservative, and combinations thereof.

15. The dosage container form according to claim 14 wherein the dosage container form comprises a glidant comprising colloidal silicon dioxide, and a surfactant selected from the group consisting of polysorbate, a poloxamer, and a combination thereof.

16. The dosage container form according to claim 1 wherein the first ingestible binder material and the second ingestible binder material are independently selected from the group consisting of a polyvinyl pyrrolidone, lactitol, modified starch, hydroxypropylmethylcellulose, spray dried lactose, fructose, mannitol, and combinations thereof.

17. The dosage container form according to claim 1 wherein the dosage container form can disintegrate in a small amount of aqueous fluid in a subject's mouth of up to 10 ml, within 5 seconds.

* * * * *